(12) United States Patent
van de Ven et al.

(10) Patent No.: US 11,800,613 B2
(45) Date of Patent: *Oct. 24, 2023

(54) LIGHTING DEVICE INCLUDING SOLID STATE EMITTERS WITH ADJUSTABLE CONTROL

(71) Applicant: IDEAL INDUSTRIES LIGHTING LLC, Racine, WI (US)

(72) Inventors: Antony Paul van de Ven, Sai Kung (HK); Chin Wah Ho, Tsuen Wan (HK); Wai Kwan Chan, Tai Po (HK); Charles M. Swoboda, Cary, NC (US)

(73) Assignee: IDEAL Industries Lighting LLC, Racine, WI (US)

( * ) Notice: Subject to any disclaimer, the term of this patent is extended or adjusted under 35 U.S.C. 154(b) by 72 days.

This patent is subject to a terminal disclaimer.

(21) Appl. No.: 17/466,108

(22) Filed: Sep. 3, 2021

(65) Prior Publication Data
US 2021/0400781 A1 Dec. 23, 2021

Related U.S. Application Data

(63) Continuation of application No. 16/435,855, filed on Jun. 10, 2019, now Pat. No. 11,116,054, which is a
(Continued)

(51) Int. Cl.
*H05B 45/20* (2020.01)
*F21K 9/238* (2016.01)
(Continued)

(52) U.S. Cl.
CPC ............ *H05B 45/20* (2020.01); *F21K 9/235* (2016.08); *F21K 9/238* (2016.08); *F21K 9/60* (2016.08);
(Continued)

(58) Field of Classification Search
CPC . F21K 9/238; F21K 9/60; F21K 9/235; H05B 45/20; H05B 47/12; H05B 47/19
See application file for complete search history.

(56) References Cited

U.S. PATENT DOCUMENTS

| | | | |
|---|---|---|---|
| 3,517,180 | A | 6/1970 | Semotan |
| 3,536,905 | A | 10/1970 | Ruff et al. |

(Continued)

FOREIGN PATENT DOCUMENTS

| | | |
|---|---|---|
| CN | 101351067 A | 1/2009 |
| CN | 203851325 U | 9/2014 |

(Continued)

OTHER PUBLICATIONS

Author Unknown, "Marvell 88MB300 Bluetooth Microcontroller: Bluetooth 4.1 Low Energy (LE) Dual Mode System-on-Chip (SoC)," Internet of Things (IoT), 2014, Marvell Technology Group Ltd., 2 pages.

(Continued)

*Primary Examiner* — Dylan C White
(74) *Attorney, Agent, or Firm* — Withrow & Terranova, P.L.L.C.; Vincent K. Gustafson

(57) ABSTRACT

Lighting devices and methods utilize multiple independently controllable groups of solid state light emitters of different dominant wavelengths, with operation of the emitter groups being automatically adjusted by processor(s) to provide desired illumination. Operation of the emitter groups may be further affected by sensors and/or user input commands (e.g., sound patterns, gesture patterns, or signal transmission). Operation may be adjusted to compensate for presence, absence, intensity, and/or color point of ambient or incident light. Presence of five or more groups of solid state light emitters provide desirable luminous flux, color point, correlated color temperature (CCT), color rendering index (CRI), CRI R9, and luminous efficacy characteristics of (Continued)

aggregate emissions over a wide range of CCT values, and may permit adjustment of vividness (e.g., relative gamut) and/or melatonin suppression characteristics for a selected color point or CCT.

20 Claims, 46 Drawing Sheets

Related U.S. Application Data continuation of application No. 15/886,134, filed on Feb. 1, 2018, now Pat. No. 10,412,809, which is a continuation of application No. 15/179,658, filed on Jun. 10, 2016, now Pat. No. 9,900,957.

(60) Provisional application No. 62/174,474, filed on Jun. 11, 2015.

(51) Int. Cl.
| | |
|---|---|
| *F21K 9/60* | (2016.01) |
| *A61N 5/06* | (2006.01) |
| *H05B 47/115* | (2020.01) |
| *F21V 29/74* | (2015.01) |
| *F21V 5/04* | (2006.01) |
| *F21V 7/00* | (2006.01) |
| *F21V 19/00* | (2006.01) |
| *F21K 9/235* | (2016.01) |
| *H05B 47/11* | (2020.01) |
| *H05B 47/12* | (2020.01) |
| *H05B 47/16* | (2020.01) |
| *H05B 47/19* | (2020.01) |
| *H05B 47/105* | (2020.01) |
| *F21Y 101/00* | (2016.01) |
| *F21Y 105/00* | (2016.01) |

(52) U.S. Cl.
CPC .............. *F21V 5/04* (2013.01); *F21V 7/00* (2013.01); *F21V 19/003* (2013.01); *F21V 29/74* (2015.01); *H05B 47/115* (2020.01); *A61N 5/0618* (2013.01); *F21Y 2101/00* (2013.01); *F21Y 2105/00* (2013.01); *H05B 47/105* (2020.01); *H05B 47/11* (2020.01); *H05B 47/12* (2020.01); *H05B 47/16* (2020.01); *H05B 47/19* (2020.01)

(56) References Cited

U.S. PATENT DOCUMENTS

| | | |
|---|---|---|
| 4,125,775 A | 11/1978 | Chodak |
| 4,734,830 A | 3/1988 | Cristian et al. |
| 4,956,751 A | 9/1990 | Kano |
| 5,803,579 A | 9/1998 | Turnbull et al. |
| 6,150,774 A | 11/2000 | Mueller et al. |
| 6,234,648 B1 | 5/2001 | Börner et al. |
| 6,357,889 B1 | 3/2002 | Duggal et al. |
| 6,441,558 B1 | 8/2002 | Muthu et al. |
| 6,498,440 B2 | 12/2002 | Stam et al. |
| 6,577,073 B2 | 6/2003 | Shimizu et al. |
| 6,600,175 B1 | 7/2003 | Baretz et al. |
| 6,788,011 B2 | 9/2004 | Mueller et al. |
| 7,005,679 B2 | 2/2006 | Tarsa et al. |
| 7,026,756 B2 | 4/2006 | Shimizu et al. |
| 7,095,056 B2 | 8/2006 | Vitta et al. |
| 7,213,940 B1 | 5/2007 | Van De Ven et al. |
| 7,233,831 B2 | 6/2007 | Blackwell |
| 7,255,457 B2 | 8/2007 | Ducharme et al. |
| 7,257,551 B2 | 8/2007 | Oskorep et al. |
| 7,344,279 B2 | 3/2008 | Mueller et al. |
| 7,352,138 B2 | 4/2008 | Lys et al. |
| 7,354,172 B2 | 4/2008 | Chemel et al. |
| 7,358,679 B2 | 4/2008 | Lys et al. |
| 7,385,359 B2 | 6/2008 | Dowling et al. |
| 7,520,634 B2 | 4/2009 | Ducharme et al. |
| 7,564,180 B2 | 7/2009 | Brandes |
| 7,687,753 B2 | 3/2010 | Ashdown |
| 7,744,242 B2 | 6/2010 | Kramer |
| 7,768,192 B2 | 8/2010 | Van De Ven et al. |
| 7,781,953 B2 | 8/2010 | Su |
| 7,824,065 B2 | 11/2010 | Maxik |
| 7,828,460 B2 | 11/2010 | Van De Ven et al. |
| 7,828,463 B1 | 11/2010 | Willis |
| 7,845,823 B2 | 12/2010 | Mueller et al. |
| 7,918,581 B2 | 4/2011 | Van De Ven et al. |
| 7,999,491 B2 | 8/2011 | Peng et al. |
| 8,038,317 B2 * | 10/2011 | Van De Ven ............ F21K 9/62 |
| | | 362/545 |
| 8,201,966 B2 | 6/2012 | Hall et al. |
| 8,258,722 B2 | 9/2012 | Swoboda et al. |
| 8,362,707 B2 | 1/2013 | Draper et al. |
| 8,436,556 B2 | 5/2013 | Eisele et al. |
| 8,508,127 B2 | 8/2013 | Negley et al. |
| 8,593,074 B2 | 11/2013 | Hatley et al. |
| 8,686,641 B2 | 4/2014 | Maxik et al. |
| 8,796,951 B2 | 8/2014 | Feri et al. |
| 9,024,536 B2 | 5/2015 | Maxik et al. |
| 9,030,103 B2 | 5/2015 | Pickard |
| 9,039,746 B2 | 5/2015 | van de Ven et al. |
| 9,192,013 B1 | 11/2015 | van de Ven et al. |
| 9,241,384 B2 | 1/2016 | van de Ven et al. |
| 9,681,510 B2 | 6/2017 | van de Ven |
| 10,349,484 B1 | 7/2019 | Zhang et al. |
| 10,412,809 B2 * | 9/2019 | van de Ven ........... F21V 19/003 |
| 10,781,984 B2 | 9/2020 | Keller et al. |
| 11,116,054 B2 * | 9/2021 | van de Ven ............... F21V 5/04 |
| 2002/0145041 A1 | 10/2002 | Muthu et al. |
| 2003/0090210 A1 | 5/2003 | Bierman |
| 2004/0218387 A1 | 11/2004 | Gerlach |
| 2005/0236998 A1 | 10/2005 | Mueller et al. |
| 2006/0106437 A1 | 5/2006 | Czeisler et al. |
| 2006/0149607 A1 | 7/2006 | Sayers et al. |
| 2007/0223219 A1 | 9/2007 | Medendorp, Jr. et al. |
| 2008/0179611 A1 | 7/2008 | Chitnis et al. |
| 2008/0215279 A1 | 9/2008 | Salsbury et al. |
| 2009/0034258 A1 | 2/2009 | Tsai et al. |
| 2009/0050907 A1 | 2/2009 | Yuan et al. |
| 2009/0079846 A1 | 3/2009 | Chou |
| 2009/0184616 A1 | 7/2009 | Van De Ven et al. |
| 2009/0296384 A1 | 12/2009 | Van De Ven et al. |
| 2010/0084996 A1 | 4/2010 | Van De Sluis et al. |
| 2010/0127283 A1 | 5/2010 | van de Ven et al. |
| 2010/0254129 A1 | 10/2010 | Le Toquin et al. |
| 2010/0277907 A1 | 11/2010 | Phipps et al. |
| 2010/0301773 A1 | 12/2010 | Chemel et al. |
| 2011/0084614 A1 | 4/2011 | Eisele et al. |
| 2011/0175510 A1 | 7/2011 | Rains, Jr. et al. |
| 2011/0282468 A1 | 11/2011 | Ashdown |
| 2012/0038291 A1 | 2/2012 | Hasnain |
| 2012/0306355 A1 | 12/2012 | Siebel, II |
| 2012/0306375 A1 | 12/2012 | van de Ven |
| 2012/0320626 A1 | 12/2012 | Quilici et al. |
| 2013/0063042 A1 | 3/2013 | Bora et al. |
| 2013/0114241 A1 | 5/2013 | van de Ven et al. |
| 2013/0271991 A1 | 10/2013 | Hussell et al. |
| 2014/0028219 A1 | 1/2014 | Chen et al. |
| 2014/0042910 A1 | 2/2014 | Chan |
| 2014/0052220 A1 | 2/2014 | Pedersen |
| 2014/0070724 A1 | 3/2014 | Gould et al. |
| 2014/0103833 A1 | 4/2014 | Ho et al. |
| 2014/0152188 A1 | 6/2014 | Bora et al. |
| 2014/0166447 A1 | 6/2014 | Thea et al. |
| 2014/0228914 A1 | 8/2014 | van de Ven et al. |
| 2014/0232288 A1 | 8/2014 | Brandes et al. |
| 2014/0292206 A1 | 10/2014 | Lashina et al. |
| 2014/0306620 A1 | 10/2014 | Maxik et al. |
| 2015/0002030 A1 | 1/2015 | McRae |
| 2015/0008827 A1 | 1/2015 | Carrigan et al. |
| 2015/0021465 A1 | 1/2015 | Gettings et al. |
| 2015/0161137 A1 | 6/2015 | Lashina et al. |
| 2015/0195855 A1 | 7/2015 | Liu |

(56) References Cited

U.S. PATENT DOCUMENTS

| | | |
|---|---|---|
| 2015/0216016 A1 | 7/2015 | Reed |
| 2015/0226392 A1 | 8/2015 | Gould et al. |
| 2015/0257243 A1 | 9/2015 | Saffari et al. |
| 2015/0264779 A1 | 9/2015 | Olsen et al. |
| 2015/0312990 A1 | 10/2015 | van de Ven et al. |
| 2015/0334789 A1 | 11/2015 | van de Ven et al. |
| 2015/0351191 A1 | 12/2015 | Pope et al. |
| 2016/0025273 A1 | 1/2016 | van de Ven et al. |
| 2016/0218254 A1 | 7/2016 | Jacobson et al. |
| 2016/0227618 A1 | 8/2016 | Meerbeek et al. |
| 2016/0241765 A1 | 8/2016 | Walters et al. |
| 2016/0273717 A1 | 9/2016 | Krames et al. |
| 2016/0273723 A1 | 9/2016 | Van Gheluwe et al. |
| 2016/0286616 A1 | 9/2016 | van de Ven |
| 2016/0366746 A1* | 12/2016 | van de Ven ............ H05B 45/20 |
| 2018/0160504 A1 | 6/2018 | van de Ven et al. |
| 2018/0246270 A1 | 8/2018 | Di Trapani et al. |
| 2018/0252374 A1 | 9/2018 | Keller et al. |
| 2018/0259140 A1 | 9/2018 | Keller et al. |
| 2019/0209858 A1 | 7/2019 | Slaughter et al. |
| 2019/0297704 A1 | 9/2019 | van de Ven et al. |
| 2019/0340306 A1 | 11/2019 | Harrison et al. |
| 2021/0400781 A1* | 12/2021 | van de Ven ........... F21V 19/003 |

FOREIGN PATENT DOCUMENTS

| | | |
|---|---|---|
| CN | 104244539 A | 12/2014 |
| CN | 105874270 A | 8/2016 |
| EP | 2918901 A1 | 9/2015 |
| FR | 3024898 A1 | 2/2016 |
| JP | 2008264430 A | 11/2008 |
| JP | 2009152213 A | 7/2009 |
| JP | 2016051608 A | 4/2016 |
| WO | 0034709 A1 | 6/2000 |
| WO | 2007114614 A1 | 10/2007 |
| WO | 2009041171 A1 | 4/2009 |
| WO | 2013085978 A2 | 6/2013 |
| WO | 2014165692 A1 | 10/2014 |
| WO | 2015049146 A1 | 4/2015 |

OTHER PUBLICATIONS

Author Unknown, "RN4020: Bluetooth® Low Energy Module," Advance Information, Mar. 25, 2014, Microchip Technology Inc., DS50002279A-p. 1 to DS50002279A-p. 26.
Duffy, Jeanne F. et al., "Effect of Light on Human Circadian Physiology," Sleep Medicine Clinic, vol. 4, Issue 2, Jun. 2009, Elsevier Inc., pp. 165-177.
Negley, Gerry, et al., "Essentials of designing efficient luminaires with LEDs," LEDs Magazine, Issue 18, Jan./Feb. 2008, Pennwell Corporation, pp. 17-22.
Rea, Mark S., et al., "Circadian Light," Journal of Circadian Rhythms, vol. 8, Issue 2, 2010, http://www.icircadianrhythms.com/content/8/1/2, pp. 1-10.
Rea, M.S., et al., "White lighting for residential applications," Lighting Research and Technology, vol. 45, Issue 3, 2013, The Chartered Institution of Building Services Engineers, pp. 331-344.
Van De Ven, Antony, et al., "Warm White illumination with high CRI and high efficacy by combining 455nm excited yellowish phosphor LEDs and red AlInGaP LEDs," The First International Conference on White LEDs and Solid State Lighting, Nov. 28, 2007, LED Lighting Fixtures, Inc., 8 pages.
Walker, Rick, "Lighting using Smart Mesh," CSR Confidential, Aug. 2013, Cambridge Silicon Radio Limited, 25 pages.
Non-Final Office Action for U.S. Appl. No. 14/669,739, dated Apr. 13, 2016, 13 pages.
Final Office Action for U.S. Appl. No. 14/669,739, dated Sep. 9, 2016, 16 pages.
Macadam, David, L., "Visual Sensitivities to Color Differences in Daylight," Journal of the Optical Society of America, vol. 32, Issue 5, May 1942, Optical Society of America, pp. 247-274.
Advisory Action and AFCP 2.0 Decision for U.S. Appl. No. 14/669,739, dated Jan. 19, 2017, 3 pages.
Notice of Allowance for U.S. Appl. No. 14/669,739, dated Feb. 28, 2017, 9 pages.
Non-Final Office Action for U.S. Appl. No. 15/179,658, dated Mar. 10, 2017, 15 pages.
Notice of Allowance for U.S. Appl. No. 15/179,658, dated Sep. 15, 2017, 9 pages.
Invitation to Pay Additional Fees and Partial International Search for International Patent Application No. PCT/IB2016/053454, dated Sep. 15, 2016, 8 pages.
International Preliminary Report on Patentability for International Patent Application No. PCT/IB2016/053454, dated Dec. 21, 2017, 13 pages.
International Search Report and Written Opinion for International Patent Application No. PCT/IB2016/053454, dated Jan. 19, 2017, 19 pages.
Cree, "Cree® J Series™ 2835 LEDs," Product Family Data Sheet: CLJ-DS8 REV 0D, Cree, Inc., Available online at: <<http://www.cree.com/led-components/media/documents/data-sheet-JSeries-2835.pdf>>, 2017, 30 pages.
Figueiro, M. G., et al., "Light at Night and Measures of Alertness and Performance: Implications for Shift Workers," Biological Research for Nursing, vol. 18, Issue 1, Feb. 19, 2015, pp. 90-100.
Jacobson, J., "CoeLux: The $40,000 Artificial Skylight Everyone Will Want," CE Pro, Available online at: <<https://www.cepro.com/article/coelux_the_40000_fake_skylight_everyone_will_want>>, Mar. 11, 2016, 9 pages.
Lumileds, "DS146 LUXEON 3535L Color Line," Product Datasheet, Lumileds Holding B.V., Available online at: <<https://www.lumileds.com/uploads/565/DS146-pdf>>, 2018, 18 pages.
Author Unknown, "The IES TM-30-15 Method," Lighting Passport, Available online at: <<https://www.lightingpassport.com/ies-tm30-15-method.html>>, Jan. 15, 2016, 6 pages.
Rea, M. S., et al., "A model of phototransduction by the human circadian system," Brain Research Reviews, vol. 50, Issue 2, Dec. 15, 2005, pp. 213-228.
Rea, M. S., et al., "Circadian light," Journal of Circadian Rhythms, vol. 8, No. 2, Feb. 13, 2010, 11 pages.
Sahin, L., et al., "Alerting effects of short-wavelength (blue) and long-wavelength (red) lights in the afternoon," Physiology & Behavior, vols. 116-117, May 27, 2013, pp. 1-7.
Seoul Semiconductor, "STB0A12D—Mid-Power LED—3528 Series Product Data Sheet," Seoul Semiconductor Co., Ltd., Revision 1.0, Available online at: <<http://www.seoulsemicon.com/upload2/3528_STB0A12D_Spec_Rev1.0.pdf>>, Jul. 21, 2017, 19 pages.
Seoul Semiconductor, "STG0A2PD—Mid-Power LED—3528 Series Product Data Sheet," Seoul Semiconductor Co., Ltd., Revision 1.0, Available online at: <<http://www.seoulsemicon.com/upload2/3528_STG0A2PD_Spec_Rev1.0.pdf>>, Jul. 21, 2017, 19 pages.
Non-Final Office Action for U.S. Appl. No. 15/886,134, dated Jun. 5, 2018, 14 pages.
Notice of Allowance and Examiner-Initiated Interview Summary for U.S. Appl. No. 15/886,134, dated Jan. 24, 2019, 11 pages.
Examination Report for European Patent Application No. 16735937.1, dated Apr. 11, 2019, 9 pages.
First Office Action for Chinese Patent Application No. 2016800474679, dated May 13, 2019, 26 pages.
Notice of Allowance for U.S. Appl. No. 15/972,176, dated Jun. 19, 2019, 8 pages.
International Search Report and Written Opinion for International Patent Application No. PCT/US2019/016592, dated Apr. 17, 2019, 16 pages.
Notice of Allowance for U.S. Appl. No. 15/972,178, dated Jun. 17, 2019, 9 pages.
Houser, K. W., et al., "Review of measures for light-source color rendition and considerations for a two-measure system for characterizing color rendition," Optics Express, vol. 21, Issue 8, Apr. 2013, Optical Society of America, 19 pages.
Non-Final Office Action for U.S. Appl. No. 16/435,855, dated Feb. 10, 2021, 7 pages.
Notice of Allowance for U.S. Appl. No. 16/435,855, dated May 13, 2021, 8 pages.

(56) References Cited

OTHER PUBLICATIONS

Examination Report for European Patent Application No. 16735937.1, dated Oct. 7, 2019, 6 pages.
Examination Report for European Patent Application No. 16735937.1, dated Jul. 29, 2020, 5 pages.
Examination Report for European Patent Application No. 19705900.9, dated Sep. 29, 2021, 7 pages.
Decision to Grant a Patent for Japanese Patent Application No. 2017-564510, dated Nov. 19, 2019, 4 pages.
Notice of Allowance for U.S. Appl. No. 16/657,254, dated May 8, 2020, 8 pages.
Non-Final Office Action for U.S. Appl. No. 16/990,230, dated Apr. 1, 2021, 8 pages.
Notice of Allowance for U.S. Appl. No. 16/990,230, dated Sep. 9, 2021, 7 pages.
International Preliminary Report on Patentability for International Patent Application No. PCT/US2019/016592, dated Aug. 20, 2020, 9 pages.
Office Action for Canadian Patent Application No. 3089271, dated Oct. 8, 2021, 4 pages.
Intention to Grant for European Patent Application No. 16735937.1, dated Jan. 10, 2022, 130 pages.
First Office Action for Chinese Patent Application No. 2019800122175, dated Dec. 29, 2021, 12 pages.
Second Office Action for Chinese Patent Application No. 2019800122175, dated Sep. 23, 2022, 13 pages.
Third Office Action for Chinese Patent Application No. 2019800122175, dated Mar. 16, 2023, 8 pages.
Decision of Rejection for Chinese Patent Application No. 2019800122175, dated Jun. 10, 2023, 6 pages.

* cited by examiner

| Daylight Sources | Color Temperature |
|---|---|
| Overcast Sky | 7000 |
| Noon Sun / Clear Summer Sky | 5000 to 7000 |
| Noon Sun / Clear Winter Sky | 5500 to 6000 |
| Noon Sunlight (Date Dependent) | 4900 to 5800 |
| Average Noon Sunlight (Northern Hemisphere) | 5400 |
| Sunlight at 30-Degree Altitude | 4500 |
| Sunlight at 20-Degree Altitude | 4000 |
| Sunlight at 10-Degree Altitude | 3500 |
| Sunrise and Sunset | 3000 |

| WL | Mel |
|---|---|
| 380 | 0.45 |
| 420 | 0.95 |
| 450 | 1 |
| 460 | 0.75 |
| 500 | 0.5 |
| 525 | 0.4 |
| 550 | 0.1 |
| 570 | 0 |

| Time of Day | Dawn to mid-morning | Mid-day | Afternoon | Mid-afternoon to evening | Late evening to bedtime | Midnight to dawn |
|---|---|---|---|---|---|---|
| Ambient light | Increasing intensity, horizontal | Very high intensity, vertical | Very high intensity, mostly vertical | Decreasing intensity | Low to none | Low to none |
| Desired aptitude | Waking up, becoming alert | Alert | Alert | Alert to relaxed | Relaxed, sleepy | Sleeping; melatonin active; night vision |
| Possible artificial light level | High > 100 | High >100 | High >100 | Medium ~25 | Low < 10 | Very low < 1 |
| Possible artificial light CCT | High (cool) >6500K | High (cool) 3500 to 5000K | High (cool) 4000K to 5000K | Medium (neutral) 3500K to 4500K | Low (warm) 2000K to 3000K | Very low < 1500K |

*FIG. 8*

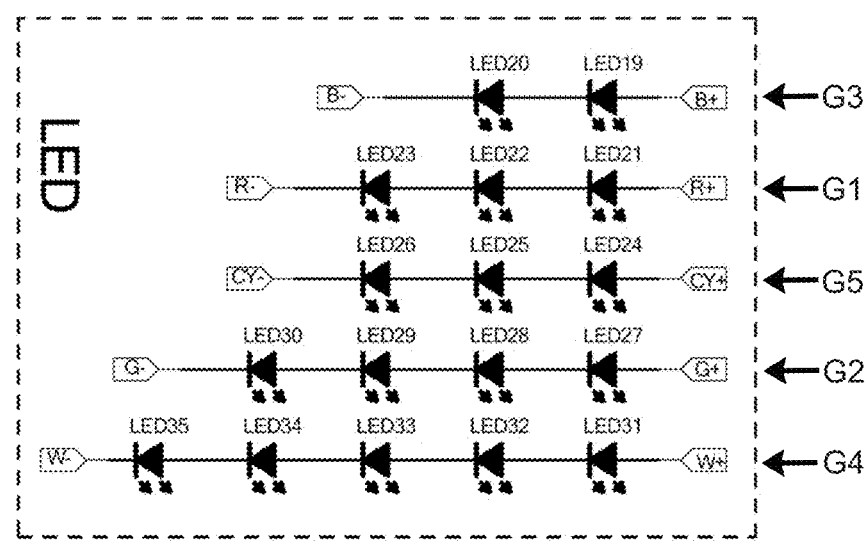

*FIG. 4A*

| Light Source | CCT | CRI | Melatonin mw / 100Lumens | Notes |
|---|---|---|---|---|
| 60W Incandescent | 2725K | 100 | 54 | Full brightness (25 when dimmed) |
| TrueWhite® LED CR6 | 2725K | 93 | 46 | Full brightness (27 when dimmed to 2000K) |
| Warm White EasyWhite® LED | 2900K | 85 | 53 | |
| Metal Halide | 3000K | 87 | 72 | |
| Tri-phosphor Fluorescent | 3400K | 82 | 66 | |
| Standard Fluorescent | 4000K | 75 | 80 | |
| Cool White EasyWhite® LED | 4000K | 75 | 90 | |
| Sun on a white wall | 5000K | 99 | 120 | |
| Daylight Fluorescent | 5200K | 75 | 125 | |
| Blue Sky | 9000K | 98 | 200 | Very high total light |

| Event | Status | Action | Time | CCT | Brightness |
|---|---|---|---|---|---|
| Apply Power | Clock is not set | turn on light | NA | 3000 | 800 |
| | Clock is set | turn on light | Sunrise | 5000 | 600 |
| | | | Sunrise + 1h | 6500 | 1000 |
| | | | 9:00 am | 5000 | 1000 |
| | | | 12:00 pm | 6000 | 1000 |
| | | | 3:00 pm | 4500 | 1000 |
| | | | 6:00 pm | 4000 | 800 |
| | | | 7:00 pm | 3500 | 750 |
| | | | 8:00 pm | 2800 | 700 |
| | | | 9:00 pm | 2500 | 650 |
| | | | 10:00 pm | 2500 | 500 |
| | | | 11:00 pm | 2300 | 250 |
| | | | 12:00 am | 1900 | 100 |
| | | | 1:00 am | 1200 | 50 |
| | | | 5:00 am | 1200 | 50 |
| Occupancy | As above, but auto turn off after 15 min. | Person moves | | | |
| Sleep Command | | Activate sleep function | | based on time of day (see above) | reduce by 80% (min. 50), then turn off after 20 min. |

*FIG. 10A*

| Event | Status | Action | Time | CCT | Brightness |
|---|---|---|---|---|---|
| *Clap Commands* | | | | | |
| Clap | Light on | Dim with decay | NA | reduce CCT to match half brightness | halve brightness |
| Double clap | Light on | Dim light to 0 with decay | NA | no change | brightness = 0, t = 3 sec |
| Clap | Brightness = 0 | use Apply Power event | use Apply Power event | use Apply Power event | use Apply Power event |
| Double clap | Brightness = 0 | restore previous setting | restore previous setting | restore previous setting | restore previous setting |
| | | | | | |
| *Voice Commands* | | | | | |
| Lights on | | use apply power event | | | |
| Lights off | | lights off | | | |
| lights dim | | halve brightness | | | |
| lights cool | | increase CCT to next CCT | | | |
| lights warm | | decrease CCT to lower CCT | | | |
| lights dance | | select (next) colorful mode - music linked | | | |

*FIG. 10B*

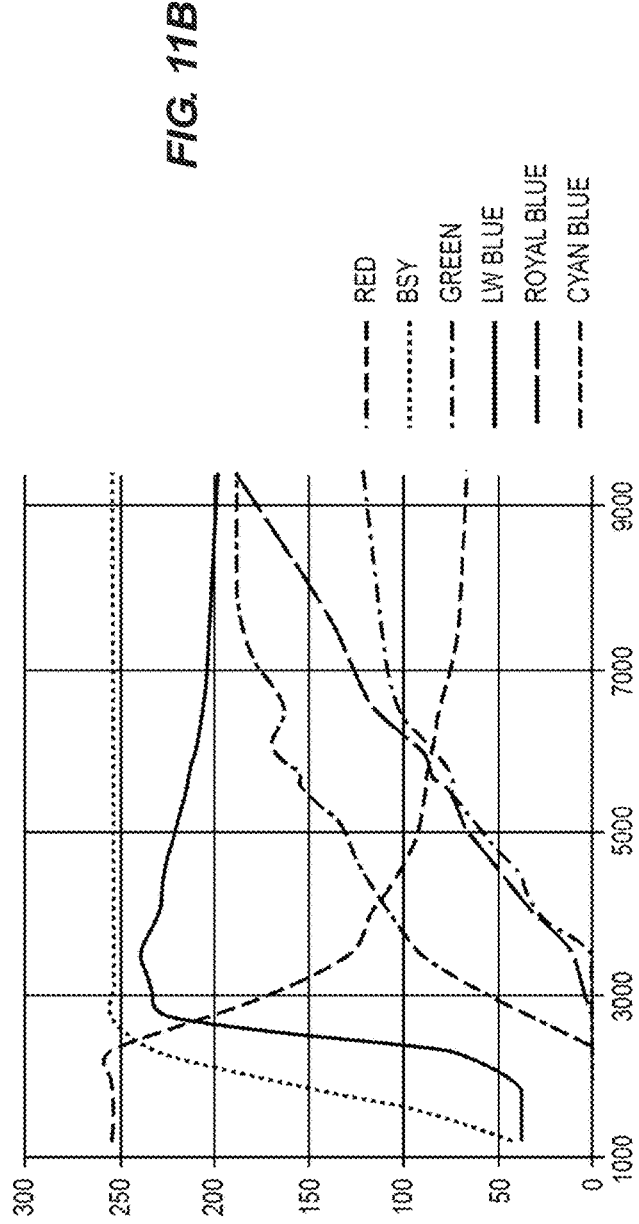

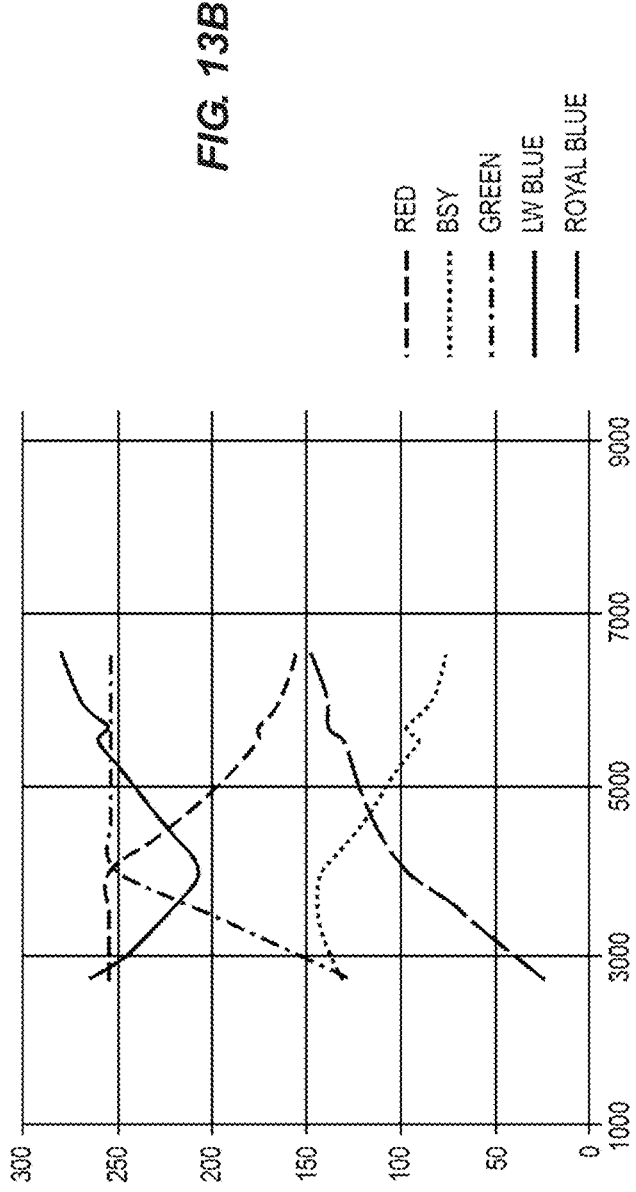

| Dull | 1200 | 1662 | 1900 | 2301 | 2732 | 3045 | 3465 | 3985 | 4503 | 5027 | 5504 | 5666 | 6200 | 6532 | 7505 | 9307 |
|---|---|---|---|---|---|---|---|---|---|---|---|---|---|---|---|---|
| R | | | | | | 144 | 102 | 63 | 38 | 17 | 0 | 0 | 0 | 0 | 0 | 0 |
| BSY | | | | | | 255 | 255 | 255 | 255 | 255 | 255 | 255 | 255 | 255 | 255 | 255 |
| G | | | | | | 0 | 0 | 0 | 0 | 0 | 0 | 1 | 16 | 31 | 55 | 70 |
| LwB | | | | | | | | | | | | | | | | |
| Roy Blue | | | | | | 29 | 45 | 61 | 78 | 91 | 101 | 108 | 119 | 138 | 170 | 215 |
| Bright set | | | | | | 243 | 253 | 264 | 270 | 277 | 281 | 280 | 272 | 263 | 251 | 243 |
| LPW | | | | | | 74 | 73 | 73 | 72 | 71 | 70 | 69 | 69 | 67 | 65 | 63 |
| CRI | | | | | | 90 | 86 | 82 | 76 | 74 | 71 | 72 | 73 | 74 | 75 | 77 |
| Qg | | | | | | 107 | 104 | 100 | 97 | 95 | 93 | 92 | 92 | 92 | 93 | 94 |
| Max Lum | | | | | | 838 | 805 | 773 | 755 | 737 | 725 | 728 | 751 | 775 | 814 | 840 |
| gai 2 | | | | | | 63% | 72% | 77% | 82% | 83% | 82% | 84% | 85% | 88% | 91% | 96% |
| CCB 2 | | | | | | 87 | 85 | 81 | 77 | 73 | 70 | 70 | 71 | 72 | 74 | 74 |

| CCT Preset | 1200 | 1600 | 1900 | 2300 | 2700 | 3000 | 3500 | 4000 | 4500 | 5000 | 5500 | 5700 | 6000 | 6500 | 7500 | 9300 |
|---|---|---|---|---|---|---|---|---|---|---|---|---|---|---|---|---|
| Red | 35 | 36 | 37 | 68 | 151 | 129 | 127 | 109 | 95 | 82 | 76 | 70 | 69 | 66 | 51 | 49 |
| Green | 0 | 0 | 0 | 0 | 25 | 27 | 63 | 73 | 78 | 81 | 90 | 83 | 82 | 99 | 98 | 100 |
| LW Blue | 0 | 0 | 0 | 3 | 35 | 57 | 36 | 51 | 67 | 80 | 94 | 91 | 97 | 102 | 92 | 104 |
| White | 9 | 22 | 35 | 99 | 247 | 253 | 254 | 252 | 251 | 253 | 246 | 254 | 254 | 241 | 249 | 244 |
| Royal Blue | 0 | 0 | 0 | 0 | 4 | 5 | 35 | 46 | 57 | 67 | 73 | 81 | 91 | 97 | 122 | 151 |
| Lumens | 51 | 75 | 100 | 250 | 650 | 650 | 700 | 700 | 700 | 700 | 700 | 700 | 700 | 700 | 700 | 700 |
| CRI | 75 | 80 | 86 | 92 | 90 | 92 | 90 | 92 | 93 | 94 | 95 | 95 | 94 | 95 | 96 | 95 |
| CQS | 19 | 73 | 83 | 90 | 94 | 95 | 94 | 95 | 95 | 95 | 95 | 95 | 95 | 95 | 93 | 92 |
| Qg | 394 | 156 | 122 | 108 | 106 | 104 | 108 | 107 | 105 | 105 | 104 | 104 | 105 | 104 | 103 | 104 |
| GAI | 13% | 28% | 32% | 39% | 53% | 62% | 75% | 84% | 91% | 94% | 97% | 98% | 102% | 102% | 104% | 109% |
| LER | 274 | 305 | 322 | 337 | 335 | 332 | 331 | 326 | 318 | 313 | 308 | 306 | 299 | 297 | 292 | 277 |
| R9 | 7 | 63 | 78 | 83 | 93 | 92 | 83 | 81 | 81 | 87 | 84 | 88 | 82 | 81 | 96 | 85 |

*FIG. 19*

| LED(s) | Steps | CCx | CCy | nm (dom) | nm (peak) | nm (cent) | CCT | FWHM | Rf W/ step | Lumen /step | Rf W | Rf% | L | L% | LER |
|---|---|---|---|---|---|---|---|---|---|---|---|---|---|---|---|
| Red | 255 | 0.6887 | 0.3111 | 618 | 628 | 625 | 749 | 20 | 0.004 | 0.8 | 0.485 | 18.4% | 215.2 | 15.4% | 222 |
| BSY | 255 | 0.3987 | 0.4673 | 569 | 556 | 570 | 4117 | 124 | 0.007 | 2.8 | 1.791 | 33.9% | 711.7 | 50.9% | 397 |
| Green | 255 | 0.1788 | 0.7195 | 528 | 520 | 526 | 7699 | 36 | 0.003 | 1.4 | 0.7 | 13.8% | 360.0 | 25.7% | 495 |
| LW Blue | 255 | 0.1137 | 0.1156 | 477 | 472 | 477 | - | 26 | 0.003 | 0.3 | 0.7 | 14.0% | 76.3 | 5.5% | 103 |
| Royal Blue | 255 | 0.1529 | 0.0244 | 454 | 448 | 451 | - | 22 | 0.004 | 0.1 | 1.058 | 20.0% | 34.9 | 2.5% | 33 |
| Sum (all 255) | 1275 | 0.3053 | 0.2910 | 464 | 448 | 538 | 7516 | 83 | | | 5.285 | 100% | 1398 | 100% | 265 |
| | | | | | | duv | -0.0135 | | | | | | | | |

*FIG. 21A*

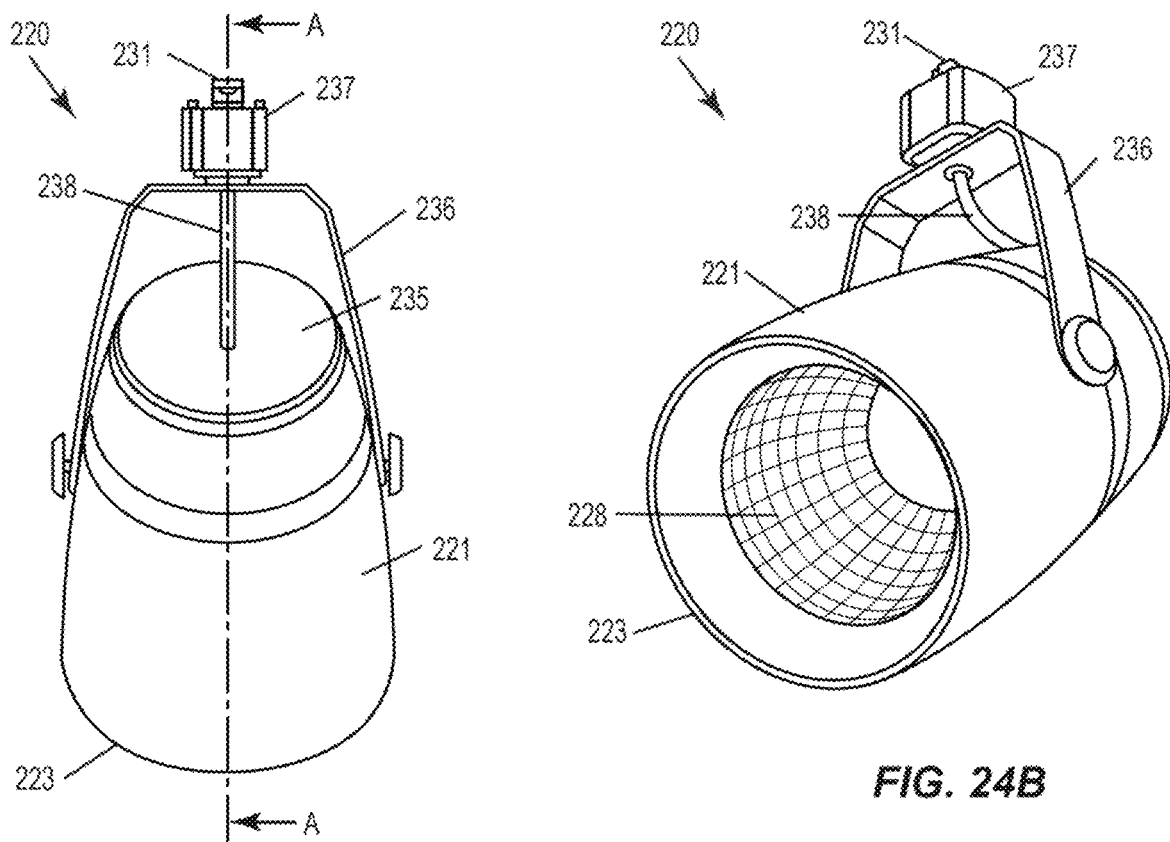
FIG. 24A
FIG. 24B
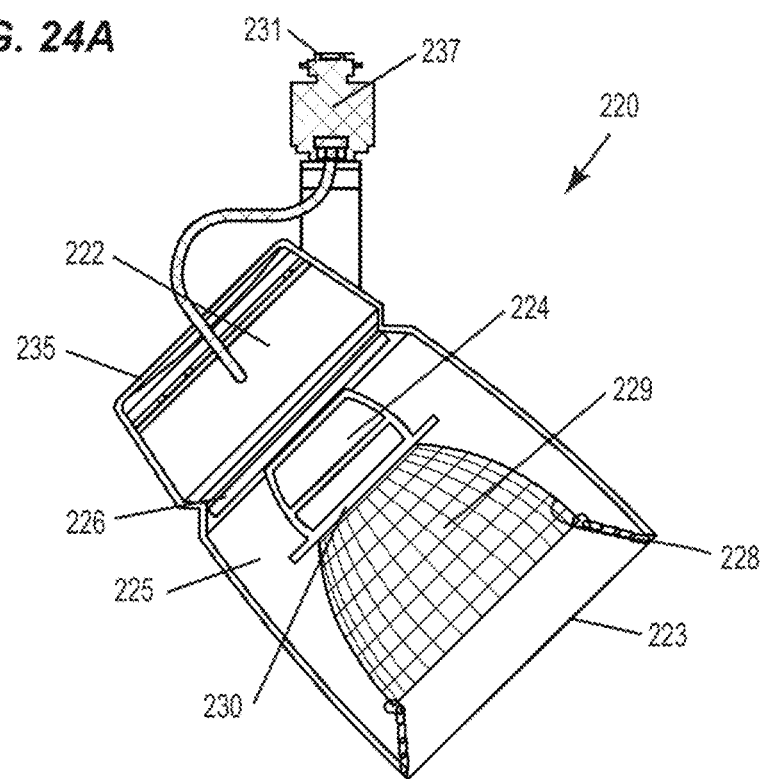
FIG. 24C

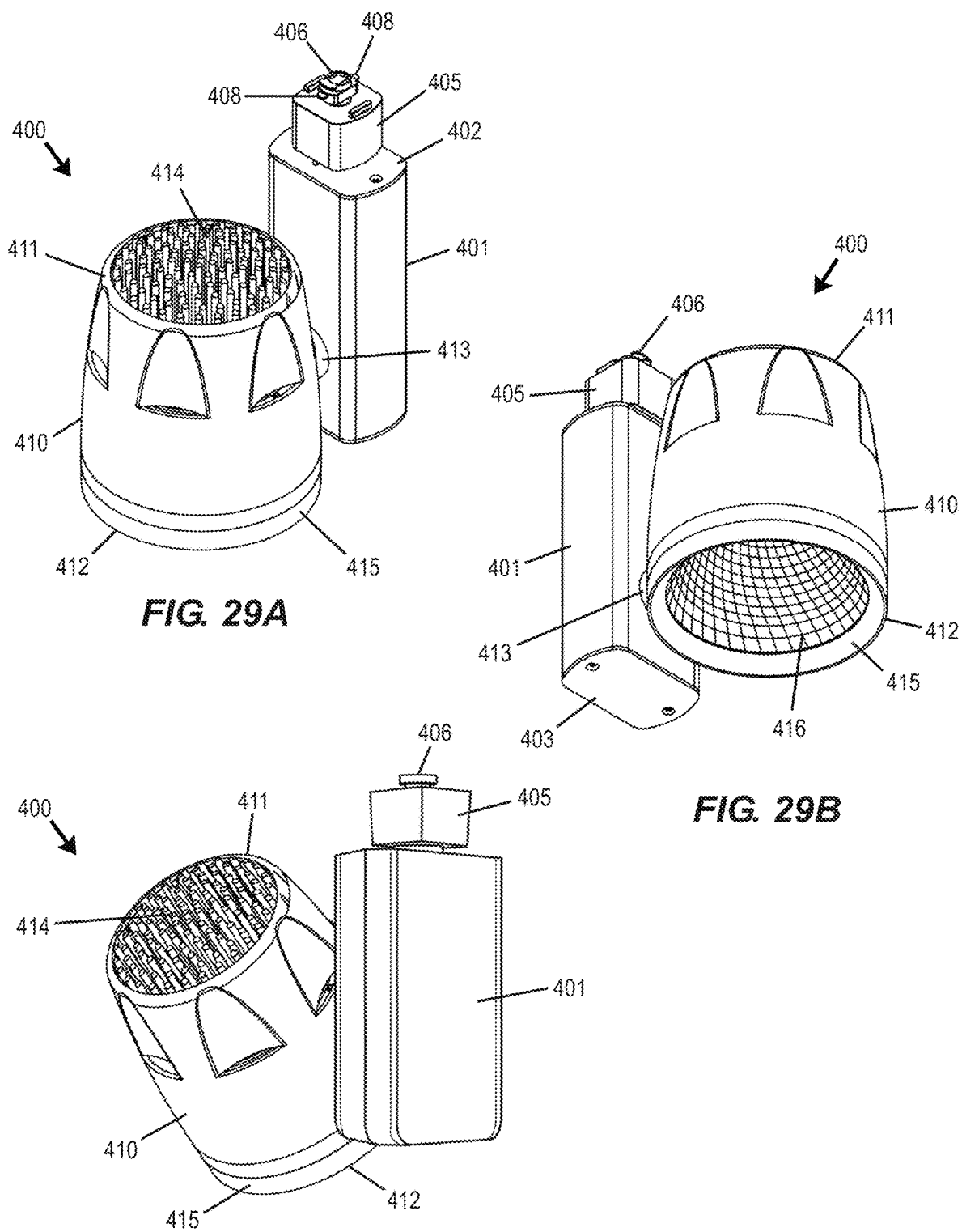

LIGHTING DEVICE INCLUDING SOLID STATE EMITTERS WITH ADJUSTABLE CONTROL

CROSS-REFERENCE TO RELATED APPLICATIONS

This application is a continuation of U.S. patent application Ser. No. 16/435,855 filed on Jun. 10, 2019, which is a continuation of U.S. patent application Ser. No. 15/886,134 filed on Feb. 1, 2018 and issued as U.S. Pat. No. 10,412,809 on Sep. 10, 2019, which is a continuation of U.S. patent application Ser. No. 15/179,658, filed on Jun. 10, 2016 and subsequently issued as U.S. Pat. No. 9,900,957 on Feb. 20, 2018, which claims priority to U.S. Provisional Patent Application No. 62/174,474 filed on Jun. 11, 2015, wherein the disclosure of the foregoing applications, publication, and patent are hereby incorporated herein by reference in their entirety.

TECHNICAL FIELD

Subject matter herein relates to lighting devices, including devices with emitters or groups of solid state light emitters being controllable to provide desired effects, and relates to associated methods of making and using such devices.

BACKGROUND

Combining light sources of different spectra permit lighting devices to emit a light spectrum of almost any desired energy content. For example, red light can be combined with unsaturated green light to yield a light spectrum that renders colors similar to daylight or similar to incandescence depending on the amount of accompanying blue light. Using red, green, and blue light sources, colors from such sources can be combined in any proportion to yield any aggregate color within the gamut of colors.

Color is the visual effect that is caused by the spectral composition of the light emitted, transmitted, or reflected by objects. Human vision is primarily related to color and brightness (contrast) of the light source, and (if reflected light is present) the spectrum that is reflected from an object being illuminated.

As a heated object becomes incandescent, it first glows reddish, then yellowish, then white, and finally bluish. Thus, apparent colors of incandescing materials are directly related to their actual temperatures (in Kelvin (K)). Practical materials that incandesce are said to have correlated color temperature (CCT) values that are directly related to color temperatures of blackbody sources. CCT is measured in Kelvin (K) and has been defined (e.g., by the Illuminating Engineering Society of North America (IESNA)) as "the absolute temperature of a blackbody whose chromaticity most nearly resembles that of the light source." Light having a CCT below 3200K is yellowish white in character and is generally considered to be warm white light, whereas light having a CCT between 3200K and 4000K is generally considered to be neutral white light, and light having a CCT above 4000K is bluish white in character and generally considered to be cool white light.

Aspects relating to the present disclosure may be better understood with reference to the 1931 CIE (Commission International de l'Eclairage) Chromaticity Diagram, which maps out human color perception in terms of two CIE parameters x and y. The 1931 CIE Chromaticity Diagram is reproduced at FIG. 1. The spectral colors are distributed around the edge of the outlined space, which includes all of the hues perceived by the human eye. The boundary line represents maximum saturation for the spectral colors. The chromaticity coordinates (i.e., color points) that lie along the blackbody locus ("BBL") obey Planck's equation: $E(\lambda)=A \lambda^{-5}/(e^{B/T}-1)$, where E is the emission intensity, $\lambda$ is the emission wavelength, T the color temperature of the blackbody, and A and B are constants.

Quality artificial lighting generally attempts to emulate the characteristics of natural light. Natural light sources include daylight with a relatively high CCT (e.g., ~5000K) and incandescent lamps with a lower CCT (e.g., ~2800K).

Solid state light emitters such as LEDs typically emit narrow wavelength bands. Such emitters include or can be used in combination with lumiphoric materials (also known as lumiphors, with examples including phosphors, scintillators, and lumiphoric inks) that absorb a portion of emissions having a first peak wavelength emitted by the emitter and re-emit light having a second peak wavelength that differs from the first peak wavelength.

Light perceived as white or near-white may be generated by a combination of red, green, and blue ("RGB") emitters, or, alternatively, by combined emissions of a blue LED and a lumiphor such as a yellow phosphor (e.g., YAG:Ce or Ce:YAG). In the latter case, a portion of the blue LED emissions passes through the phosphor, while another portion of the blue emissions is downconverted to yellow, and the blue and yellow light in combination are perceived as white.

Depending on the combination of LEDs and/or lumiphors used, aggregate emissions of a solid state device may be under-saturated with certain colors of the spectrum or over-saturated with certain colors.

Color reproduction is commonly measured using Color Rendering Index (CRI) or average Color Rendering Index (CRI Ra). To calculate CRI, the color appearance of 14 reflective samples is simulated when illuminated by a reference radiator (illuminant) and the test source. The general or average color rendering index CRI Ra is a modified average utilizing the first eight indices, all of which are pastel colored with low to moderate chromatic saturation. (R9 is one of six saturated test colors not used in calculating CRI, with R9 embodying a large red content.) CRI and CRI Ra are used to determine how closely an artificial light source matches the color rendering of a natural light source at the same CCT. Daylight has a high CRI Ra (approximately 100), with incandescent bulbs also being relatively close (CRI Ra greater than 95), and fluorescent lighting being less accurate (with typical CRI Ra values of approximately 70-80).

CRI Ra (or CRI) alone is not a satisfactory measure of the benefit of a light source, since it confers little ability to predict color discrimination (i.e., to perceive subtle difference in hue) or color preference. There appears to be a natural human attraction to brighter color. Daylight provides a spectrum of light that allows the human eye to perceive bright and vivid colors, which allows objects to be distinguished even with subtle color shade differences. Accordingly, it is generally recognized that daylight and blackbody sources are superior to many artificial light sources for emphasizing and distinguishing color. The ability of human vision to differentiate color is different under CCT conditions providing the same CRI Ra. Such differentiation is proportional to the gamut of the illuminating light.

Gamut area of a light source can be calculated as the area enclosed within a polygon defined by the chromaticities in CIE 1976 u'v' color space of the eight color chips used to calculate CRI Ra when illuminated by a test light source. Gamut area index (GAI) is a convenient way of characterizing in chromaticity space how saturated the illumination makes objects appear—with a larger GAI making object colors appear more saturated. GAI is a relative number whereby an imaginary equal-energy spectrum (wherein radiant power is equal at all wavelengths) is scored as 100. GAI for a test source is determined by comparing color space area of the light being tested to the color space area produced by the imaginary or theoretical equal-energy spectrum (EES) source. Unlike CRI Ra (or CRI), which has a maximum value of 100, GAI can exceed 100, meaning that some sources saturate colors more than an equal-energy source serves to saturate color.

It is found that typical blackbody-like light sources and typical daylight-like light sources have different gamut areas. Low CCT sources (e.g., incandescent emitters) have a GAI of approximately 50% (i.e., about half the gamut area of the EES source). Sources with higher CCT values have a larger GAI. For example, a very bluish light with a CCT of 10000K may have a GAI of 140%.

Another way of characterizing how saturated an illuminant makes objects appear is relative gamut area, or "Qg" (also referred to as "Color Quality Scale Qg" or "CQS Qg"), which is the area formed by (a*, b*) coordinates of the 15 test-color samples in CIELAB normalized by the gamut area of a reference illuminant at the same CCT and multiplied by 100. In a manner similar to GAI, Qg values can exceed 100; however, Qg values are scaled for consistency relative to CCT. Because of chromatic adaptation, and because CCT is selected to set the overall color tone of an environment as part of the lighting design process, variable-reference measures such as Qg may be especially relevant to applied lighting design. If the relative gamut is greater than that of the reference, and if illuminance is lower than that provided by daylight, then an increase in preference and discrimination might be expected relative to the reference at that same CCT. Conversely, if the relative gamut is smaller than that of the reference, then a decrease in preference and discrimination might be expected relative to the reference at the same CCT.

It is believed that, in at least certain contexts, some consumers may prefer light sources with significantly enhanced vividness. It may be challenging to provide enhanced vividness in combination with high luminous efficacy, and further in combination with reasonably high color rendering index values.

It is important that lighting be of appropriate intensity for the task at hand and also have appropriate color rendering characteristics. For most daytime tasks, light sources (whether artificial or natural) should have high intensity and high color rendering. Conversely, for sleeping, light should have very low levels. The color differentiation of night vision is very low.

Light affects human circadian rhythms. Human physiology responds non-visually to the presence or absence of certain wavelengths. For example, blue light is known to suppress melatonin, and ultraviolet rays are known to damage the skin. The intensity of light and the spectral content of light have a strong effect on the human circadian rhythms. These circadian rhythms are ideally synchronized with the natural light.

Circadian rhythm disorders may be associated with change in nocturnal activity (e.g., nighttime shift workers), change in longitude (e.g., jet lag), and/or seasonal change in light duration (e.g., seasonal affective disorder, with symptoms including depression). In 2007, the World Health Organization named late night shift work as a probable cancer-causing agent. Melatonin is an anti-oxidant and suppressant of tumor development; accordingly, interference with melatonin levels may increase the likelihood of developing cancer. Methods involving stimuli with artificial light sources to modify the phase and amplitude of a human circadian cycle (e.g., for cycle resetting) have been developed, such as disclosed in U.S. Patent Application Publication No. 2006/0106437A1 to Czeisler et al.

Artificial light sometimes includes too much blue light in the evening, which suppresses melatonin and hinders restful sleep. Exposure to artificial light during the night may inhibit a person from falling to sleep or returning to sleep, and may also cause a temporary loss of night vision. It is principally blue light (e.g., including blue light at a peak wavelength value between 460 to 480 nm, with some activity from about 360 nm to about 600 nm), that suppresses melatonin and synchronizes the circadian clock, proportional to the light intensity and length of exposure. As shown in FIG. 2, the action spectrum for melatonin suppression (with six individual data points represented as black squares) shows short-wavelength sensitivity that is very different from the known spectral sensitivity of the scotopic response curve (represented with a solid line) and photopic response curve (represented with a dashed line).

Natural light varies with respect to intensity and/or CCT depending on season, latitude, altitude, time of day, and weather conditions. Natural light also varies each day with respect to intensity and CCT. The changing CCT of sunlight over the course of a day is mainly a result of scattering of light, rather than changes in black-body radiation. Ignoring variations due to weather conditions, natural light intensity typically is low at sunrise, increases through mid-morning to a high level at mid-day, and then decreases in mid-afternoon to evening to a low level at sunset. CCT also varies in a predicable manner. During sunrise and sunset, CCT tends to be around 2,000K; an intermediate CCT value of around 3,500K is exhibited shortly after sunrise or before sunset (when daylight is redder and softer compared to when the Sun is higher in the sky); and a CCT of around 5,400K is exhibited around noontime. Color temperatures for various daylight sources are tabulated in FIG. 3. Low (or warm) CCT values are consistent with reduced blue content, while higher (or cool) CCT values are consistent with increased blue content.

Generally, a light that is dim and exhibits a low (warm) CCT promotes restfulness (e.g., such as may be desirable in the evening and night before sleep), and a light that is bright and exhibits a high (cool) CCT promotes alertness (such as may be desirable in the morning and during the day). A light having a very low intensity and a very low CCT would least interfere with a person returning to sleep after being awakened in the middle of the night.

Color changing lights are known in the art. One example of a color changing light bulb is the Philips "Hue" bulb (Koninklijke Philips N. V., Eindhoven, the Netherlands), which is understood to include an array of red LEDs, blue LEDs, and blue shifted green LEDs (each including a blue LED arranged to stimulate emissions of a green phosphor to provide very saturated green color). Such bulbs permit different colors, CCTs, and/or intensities of light to be selected by a user via a computer or portable electronic device.

Despite the availability of color changing lamps, such lamps have limitations that inhibit their utility. It can be difficult for users to program and/or operate lighting devices to obtain desired illumination conditions that take into account temporal variations in natural light. Avoiding potential interference with circadian rhythms without unduly sacrificing perceived light quality is another concern. It can also be difficult to provide vivid illumination in combination with high color rendering at a desired color point. Still another concern includes maintaining high luminous efficacy over a variety of illumination conditions. Additional concerns include ease of control by one or more users. It can also be difficult for users to program lighting devices to obtain desired illumination conditions that take into account variations in natural light that may be attributable to multiple factors such as the season, latitude, time of day, and weather conditions.

The art continues to seek improved lighting devices and methods that address limitations of conventional lighting devices and methods.

SUMMARY

The present disclosure relates to lighting devices and lighting methods utilizing multiple independently controllable groups of solid state light emitters of different dominant wavelengths, with operation of the groups of solid state light emitters being automatically adjusted by at least one processor to provide desired illumination, and (in at least certain embodiments) with operation of the groups of solid state light emitters subject to being further affected by sensors and/or user input commands (e.g., user-generated sound patterns, user-generated gesture patterns, or user-initiated signal transmission (wired or wireless)). In certain embodiments, a lighting device may be adjusted to compensate for presence, absence, intensity, and/or color point of ambient or incident light. Presence of at least five groups of solid state light emitters may provide desirable luminous flux, color point, correlated color temperature (CCT), color rendering index (CRI), CRI R9, and luminous efficacy characteristics of aggregate emissions over a wide range of CCT values, and may also permit adjustment of vividness (e.g., Qg) and/or melatonin suppression characteristics for a selected color point or CCT of aggregate emissions. A lighting device including a first transceiver arranged to communicate with a digital communication device or a digital computing device and including a second transceiver arranged to communicate with other lighting devices is also provided. Methods facilitating control of a lighting device are additionally provided.

In one aspect, a solid state lighting device includes a plurality of groups of solid state light emitters, at least one sensor, a memory, at least one detector, and at least one processor. Each group of solid state light emitters is arranged to generate emissions comprising a dominant wavelength that differs from a dominant wavelength of emissions generated by each other group of solid state light emitters. Each group of solid state light emitters is independently controllable, and emissions generated by each group of solid state light emitters are arranged to be combined to produce aggregate emissions of the lighting device. The at least one sensor is arranged to receive or provide at least one signal indicative of an environmental condition. The memory is arranged to store at least one operating instruction set. The at least one detector is arranged to detect one or more of (i) multiple different user-generated sound patterns indicative of user commands, (ii) multiple different user-generated gesture patterns indicative of user commands, and (iii) at least one user-initiated signal (e.g., wired or wireless), and produce at least one detector output signal responsive to such detection. The at least one processor is arranged to utilize the at least one operating instruction set to automatically adjust at different hours of a calendar day (a) luminous flux of the aggregate emissions and (b) at least one of correlated color temperature and color point of the aggregate emissions, responsive to at least one of (i) time and (ii) the at least one signal indicative of an environmental condition. The at least one processor is further arranged to suspend or alter automatic adjustment of (a) luminous flux of the aggregate emissions and (b) at least one of correlated color temperature and color point of the aggregate emissions, responsive to the at least one detector output signal. In certain embodiments, at least five groups of solid state light emitters are provided. In certain embodiments, the at least one processor is arranged to adjust, responsive to the at least one detector output signal and for a selected color point or correlated color temperature of the aggregated emissions, at least one of (c) melatonin suppressing milliwatts per hundred lumens of the aggregate emissions and (d) relative gamut of the aggregate emissions. In certain embodiments, the at least one sensor arranged to receive or provide at least one signal indicative of an environmental condition is arranged to sense one or more of: humidity, air pressure, ambient sound, gas concentration, presence or absence of gas, particulate concentration, presence or absence of particulates, temperature, cloud cover, outdoor ambient temperature, outdoor ambient light level, outdoor CCT, presence of precipitation, type of precipitation, UV index, solar radiation index, moon phase, moonlight light level, presence of aurora, and chill factor. In certain embodiments, the at least one sensor comprises an ambient light sensor, an image sensor, a temperature sensor, a barometric pressure sensor, a humidity sensor, a weather information receiver, a gas detector, and a particulate detector.

In another aspect, a solid state lighting device comprises: a plurality of groups of solid state light emitters, wherein each group of solid state light emitters is arranged to generate emissions comprising a dominant wavelength that differs from a dominant wavelength of emissions generated by each other group of solid state light emitters, each group of solid state light emitters is independently controllable, wherein emissions generated by each group of solid state light emitters are arranged to be combined to produce aggregate emissions of the lighting device, and wherein the plurality of groups includes at least five groups of solid state light emitters; at least one sensor arranged to receive or provide at least one signal indicative of an environmental condition; a memory storing at least one operating instruction set; and at least one processor arranged to utilize the at least one operating instruction set to automatically adjust at different hours of a calendar day (a) luminous flux of the aggregate emissions and (b) at least one of correlated color temperature and color point of the aggregate emissions, responsive to at least one of (i) time and (ii) the at least one signal indicative of an environmental condition; wherein the aggregate emissions generated by the lighting device comprise at least two of the following characteristics (A) to (D): (A) a CRI value of at least 90 and a Qg value of at least 100 over a correlated color temperature range spanning at least from 2700K to 9000K; (B) a CRI R9 value of at least 80 over a correlated color temperature range spanning at least from 2700K to 9000K; (C) a luminous flux value of at least 600 over a correlated color temperature range spanning at least from 2700K to 9000K; and (D) a luminous efficacy of radiation value of at least 300 over a correlated color temperature range spanning at least from 2700K to 5700K.

In certain embodiments, a solid state lighting device comprises: a plurality of groups of solid state light emitters, wherein each group of solid state light emitters is arranged to generate emissions comprising a dominant wavelength that differs from a dominant wavelength of emissions generated by each other group of solid state light emitters, each group of solid state light emitters is independently controllable, emissions generated by each group of solid state light emitters are arranged to be combined to produce aggregate emissions of the lighting device, and the plurality of groups includes at least five groups of solid state light emitters; a memory storing at least one operating instruction set; and at least one processor arranged to utilize the at least one operating instruction set to automatically adjust (a) luminous flux of the aggregate emissions and (b) at least one of correlated color temperature and color point of the aggregate emissions; and a first wireless transceiver arranged to receive at least one signal from a digital communication device or a digital computing device; wherein the at least one processor is arranged to adjust, responsive to the received at least one signal and for a selected color point or correlated color temperature of the aggregated emissions, at least one of (c) melatonin suppressing milliwatts per hundred lumens of the aggregate emissions and (d) relative gamut of the aggregate emissions.

In another aspect, a solid state lighting device comprises: a plurality of groups of solid state light emitters, wherein each group of solid state light emitters is arranged to generate emissions comprising a dominant wavelength that differs from a dominant wavelength of emissions generated by each other group of solid state light emitters, each group of solid state light emitters is independently controllable, and emissions generated by each group of solid state light emitters are arranged to be combined to produce aggregate emissions of the lighting device; a first wireless transceiver arranged to communicate with a digital communication device or a digital computing device; a second wireless transceiver arranged to communicate with at least one other solid state lighting device; a memory arranged to store at least one operating instruction set; and at least one processor arranged to utilize the at least one operating instruction set to automatically adjust at different hours of a calendar day (a) luminous flux of the aggregate emissions and (b) at least one of correlated color temperature and color point of the aggregate emissions; wherein the first wireless transceiver is arranged to receive at least one first signal from a digital communication device or a digital computing device to select or modify the at least one operating instruction set; wherein the second wireless transceiver is arranged to transmit at least one second signal to the at least one other solid state lighting device indicative of or including a selected or modified at least one instruction set that was selected or modified responsive to the at least one first signal.

In another aspect, a solid state lighting device comprises: a plurality of groups of solid state light emitters, wherein each group of solid state light emitters is arranged to generate emissions comprising a dominant wavelength that differs from a dominant wavelength of emissions generated by each other group of solid state light emitters, each group of solid state light emitters is independently controllable, and emissions generated by each group of solid state light emitters are arranged to be combined to produce aggregate emissions of the lighting device; at least one sensor arranged to receive or provide at least one signal indicative of an environmental condition; a memory storing at least one operating instruction set; at least one processor arranged to utilize the at least one operating instruction set to automatically adjust (a) luminous flux of the aggregate emissions and (b) at least one of correlated color temperature and color point of the aggregate emissions, responsive to the at least one signal indicative of an environmental condition; and a body structure, wherein the plurality of groups of solid state light emitters, the memory, and the at least one processor are arranged in or on the body structure.

In another aspect, a solid state lighting device comprises: a body structure, a reprogrammable memory, at least one processor, a plurality of solid state light emitters, and a communication interface, wherein: emissions generated by the solid state light emitters are arranged to be combined to produce aggregate emissions of the lighting device; the memory is arranged to store a plurality of selectable algorithms each including different instructions for controlling operation of the plurality of solid state light emitters; the at least one processor is in electrical communication with the memory and is arranged to execute steps of at least one algorithm of the plurality of selectable algorithms; the communication interface is arranged to receive an additional algorithm including instructions for controlling operation of the plurality of solid state light emitters; and the memory is arranged to store the additional algorithm received from the communication interface to permit the at least one processor to execute steps of the additional algorithm for controlling operation of the lighting device. In certain embodiments, the communication interface comprises a wireless receiver or a wireless transceiver, and the wireless receiver or the wireless transceiver is arranged to receive the additional algorithm wirelessly from a digital communication device or a digital computing device.

In another aspect, a method facilitates control of a lighting device that comprises a memory and a plurality of groups of solid state light emitters, wherein each group of solid state light emitters is arranged to generate emissions comprising a dominant wavelength that differs from a dominant wavelength of emissions generated by each other group of solid state light emitters, each group of solid state light emitters is independently controllable, and emissions generated by each group of solid state light emitters are arranged to be combined to produce aggregate emissions of the lighting device, the method comprising: detecting usage of the lighting device; storing, in the memory of the lighting device, information regarding detected usage of the lighting device, wherein the stored information includes information indicative of color point and luminous flux of aggregate emissions with respect to time; analyzing the stored information to identify one or more temporal patterns of usage of the lighting device; generating a proposed operating instruction set responsive to the identification of one or more temporal patterns of usage; and adjusting operation of the plurality of groups of solid state light emitters utilizing the proposed operating instruction set.

In another aspect, a method facilitates control of a lighting device that comprises a body structure, a memory, a processor, and a plurality of solid state light emitters, wherein the memory, the processor, and the plurality of solid state light emitters are arranged in or on the body structure; the memory is arranged to store a plurality of selectable algorithms arranged to enable different control of operation the plurality of solid state light emitters; the processor is arranged to execute steps of at least one algorithm of the plurality of selectable algorithms; and emissions generated by the solid state light emitters are arranged to be combined to produce aggregate emissions of the lighting device, the method comprising: downloading or retrieving from a communication network an additional selectable algorithm arranged to enable control of operation of the plurality of solid state light emitters; and saving the additional selectable algorithm in the memory of the lighting device while maintaining in the memory at least one other selectable algorithm.

In certain embodiments, a light bulb or light fixture may include at least one lighting device as disclosed herein.

In certain embodiments, a lighting system may include multiple lighting devices as disclosed herein. In certain embodiments, multiple lighting devices as disclosed herein may be arranged to communicate wirelessly with one another.

In another aspect, the invention relates to a method comprising illuminating an object, a space, or an environment, utilizing a solid state lighting device as described herein.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Other aspects, features, and embodiments of the invention will be more fully apparent from the ensuing disclosure and appended claims.

BRIEF DESCRIPTION OF THE DRAWINGS

FIG. 4A is a schematic illustrating five groups (strings) of light emitting diodes (LEDs) separately arranged to emit short wavelength blue, red, long wavelength blue (or cyan), green, and white (or blue-shifted yellow) light.

FIG. 8 is a table identifying, for different times of day, ambient light, desired aptitude, and possible artificial light intensity levels and CCT values that may promote wellness when used with lighting devices and systems according to at least certain embodiments of the disclosure.

FIGS. 10A-10B embody a table identifying event name, system status, action, time, CCT, and brightness settings for an algorithm including instructions for operating a lighting device or lighting system according to one embodiment of the disclosure.

FIG. 11A is a table identifying emitter control step (within a range of from 0 to 255), brightness setting, luminous efficacy, CRI, relative gamut area (Qg), maximum lumens, gamut area index (GAI), and color quality scale (CQS) values for a lighting device including five groups of LEDs (red, blue-shifted yellow (white), green, long wavelength blue or cyan, and short wavelength blue) operated at sixteen different CCT values according to a "High CRI" setting or instruction set.

FIG. 11B is an overlay plot of control step versus CCT for each of the five groups of LEDs of FIG. 11A.

FIG. 13A is a table identifying emitter control step (within a range of from 0 to 255), brightness setting, luminous efficacy, CRI, Qg, maximum lumens, GAI, and CQS values for a lighting device including five groups of LEDs (red, blue-shifted yellow (white), green, long wavelength blue or cyan, and short wavelength blue) operated at ten different CCT values according to a "Very Vibrant" setting or instruction set.

FIG. 13B is an overlay plot of control step versus CCT for each of the five groups of LEDs of FIG. 13A.

FIG. 19 is a table identifying emitter control step (within a range of from 0 to 255), aggregate lumens, color rendering index (CRI), color quality scale (CQS), relative gamut area (Qg), gamut area index (GAI), luminous efficacy of radiation (LER), and CRI R9 for a lighting device according to one embodiment of the disclosure including five groups of LEDs operated at sixteen different CCT values according to an instruction set arranged to simultaneously achieve high CRI (at least 90) and high Qg (exceeding 100) for multiple CCT values spanning from 2300K to 9300K. Aggregate lumens in a range of from 650-700 lumens were obtained from 2700K to 9300K.

FIG. 21A is a table providing control step (in a range of from 0-255), x color coordinate, y color coordinate, dominant wavelength, peak wavelength, center wavelength, CCT, full width-half maximum, radiant flux (Watts) per control step, lumens per control step, radiant flux (Watts), percent radiant flux, lumens, percent lumens, and luminous efficacy of radiation for a five groups of LEDs (red, blue-shifted yellow, green, long wavelength blue or cyan, and short wavelength blue) of a lighting device with each group operated at maximum current.

FIG. 24A is a rear elevation view of a lighting device according to one embodiment of the disclosure embodied in a substantially cylindrical track light fixture intended to be supported by a wall- or ceiling-mounted track and including multiple (e.g., five or more) separately controllable groups of LEDs.

FIG. 24B is a front perspective view of the lighting device of FIG. 24A.

FIG. 24C is a cross-sectional view of the lighting device of FIGS. 24A-24B.

FIG. 29A is an upper perspective view of a lighting device according to one embodiment of the disclosure embodied in a track light fixture intended to be supported by a wall- or ceiling-mounted track and arranged in a first position.

FIG. 29B is a lower perspective view of the lighting device of FIG. 29A in the first position.

FIG. 29C is a rear perspective view of the lighting device of FIGS. 29A and 29B in a second position, with a generally cylindrical light housing pivoted relative to a driver box.

DETAILED DESCRIPTION

Figure 1:
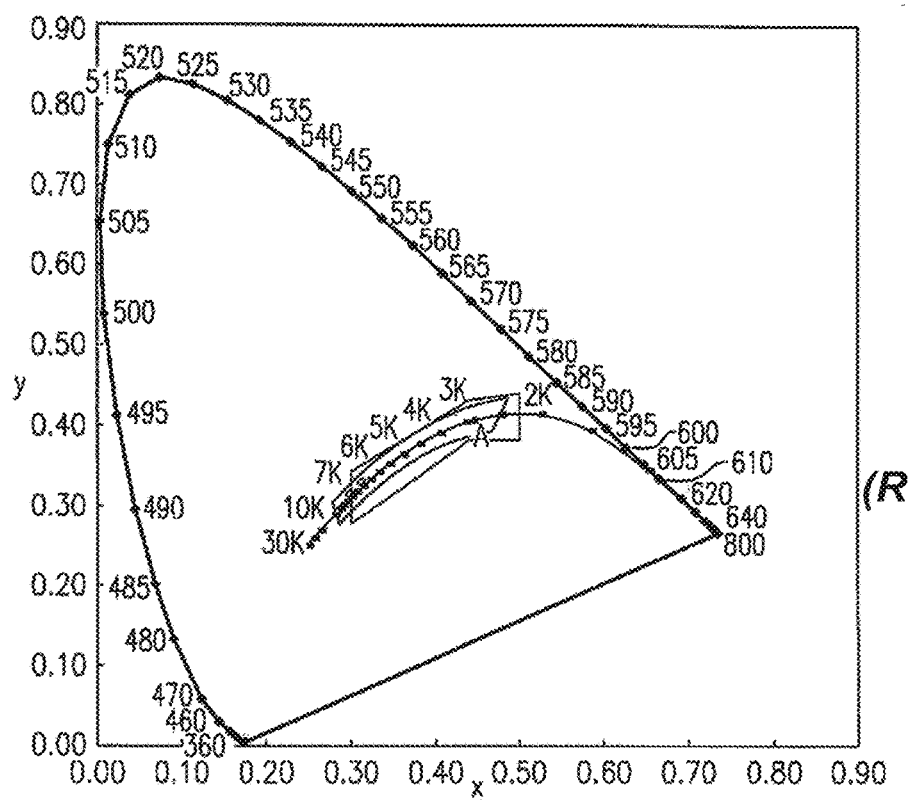
FIG. 1 is a 1931 CIE Chromaticity Diagram including representation of the blackbody locus, and further illustrating an approximately white area bounding the blackbody locus.

As noted previously, the present disclosure relates to lighting devices and lighting methods utilizing multiple independently controllable groups of solid state light emitters of different dominant wavelengths, with operation of the groups of solid state light emitters being automatically adjusted by at least one processor to provide desired illumination, and (in at least certain embodiments) with operation of the groups of solid state light emitters subject to being further affected by sensors or user input commands (e.g., user-generated sound patterns, user-generated gesture patterns, or user-initiated signal transmission). Presence of at least five groups of solid state light emitters may provide desirable relative gamut area (Qg(, color rendering index (CRI), CRI R9, and luminous efficacy characteristics over a wide range of correlated color temperature (CCT) values, and may also permit adjustment of vividness (e.g., Qg) and/or melatonin suppression characteristics for a selected color point or CCT of aggregate emissions. Further provided is a lighting device including a first transceiver arranged to communicate with a digital communication device or a digital computing device and including a second transceiver arranged to communicate with other lighting devices. Additionally provided is a lighting device including a reprogrammable memory arranged to store multiple selectable algorithms each including different instructions useable by at least one processor for controlling operation of multiple solid state light emitters of the lighting device, wherein a communication interface is arranged to receive an additional algorithm for storage by the memory to permit the at least one processor to execute steps of the additional algorithm for controlling operation of the lighting device. Still further provided is a method for facilitating control of a lighting device including detecting usage of the device, storing information regarding the detected usage, automatically analyzing the stored information to identify temporal patterns of usage, and generating and using a modified set of operating instructions.

In certain embodiments, enhanced efficacy can be obtained by producing more light in useful areas of the visible spectrum. In certain embodiments, more vivid and colorful representation of surfaces and objects may be obtained. It has been found that enhanced color saturation renders objects more attractive to a majority of viewers. In certain embodiments, enhanced color contrast may be obtained, conferring improved discernibility between colors and legibility of objects. In certain embodiments, aggregate emissions may be controlled to provide CRI values in a range of from 50 to 100 (or subranges thereof), and/or Qg values in a range of from 50 to 150 (or subranges thereof).

Further disclosed herein are lighting devices and lighting systems arranged to receive or determine information indicative of geospatial or geographic location (and optionally additional information such as time, time zone, and/or date) and automatically adjust one or more light output parameters based at least in part on such information to operate one or more electrically activated emitters differently on different days of a year. At least one signal indicative of or permitting derivation of geospatial position may be obtained or provided by at least one element selected from (a) a user input element, (b) a signal receiver, and (c) at least one sensor.

More specific aspects of the invention will be described after terms are defined and general concepts are introduced.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

Unless otherwise defined, terms used herein should be construed to have the same meaning as commonly understood by one of ordinary skill in the art to which this invention belongs. It will be further understood that terms used herein should be interpreted as having a meaning that is consistent with their meaning in the context of this specification and the relevant art, and should not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

Relative terms such as "below" or "above" or "upper" or "lower" or "horizontal" or "vertical" may be used herein to describe a relationship of one element, layer, or region to another element, layer, or region as illustrated in the figures. It will be understood that these terms and those discussed above are intended to encompass different orientations of the device in addition to the orientation depicted in the figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. Unless the absence of one or more elements is specifically recited, the terms "comprising," "including," and "having" as used herein should be interpreted as open-ended terms that do not preclude the presence of one or more elements. As used herein, the phrase "arranged to" should be interpreted as synonymous with the phrase "configured to" and generally contemplates an intentional arrangement to achieve a stated purpose, result, or interaction.

The terms "solid state light emitter" or "solid state light emitter" (which may be qualified as being "electrically activated") may include a LED, laser diode, organic light-emitting diode, and/or other semiconductor device which includes one or more semiconductor layers, which may include silicon, silicon carbide, gallium nitride and/or other semiconductor materials, a substrate which may include sapphire, silicon, silicon carbide and/or other microelectronic substrates, and one or more contact layers which may include metal and/or other conductive materials.

The term "dominant wavelength" as used herein refers to the dominant wavelength at a reference condition used to classify LED die or individual lamps, and in general it is different from the dominant wavelength that would be measured under luminaire operating conditions of any particular embodiment.

Solid state light emitting devices according to embodiments of the present disclosure may include, but are not limited to, III-V nitride based LED chips or laser chips fabricated on a silicon, silicon carbide, sapphire, or III-V nitride growth substrate, including (for example) devices manufactured and sold by Cree, Inc. of Durham, N.C. Solid state light emitters may be used individually or in groups to emit one or more beams to stimulate emissions of one or more lumiphoric materials (e.g., phosphors, scintillators, lumiphoric inks, quantum dots, day glow tapes, etc.) to generate light at one or more peak wavelength(s), or of at least one desired perceived color (including combinations of colors that may be perceived as white). Lumiphoric materials may be provided in the form of particles, films, or sheets. Quantum dot materials of various colors are commercially available from QD Vision, Inc. (Lexington, Mass., USA), Nanosys Inc. (Milpitas, Calif., USA), and Nanoco Technologies Ltd. (Manchester, United Kingdom), among others.

Inclusion of lumiphoric (also called "luminescent") materials in lighting devices as described herein may be accomplished by any suitable means, including the following: direct coating on solid state light emitters, dispersal in encapsulant materials arranged to cover solid state light emitters, coating on lumiphor support elements (e.g., by powder coating, inkjet printing, or the like), incorporation into diffusers or lenses, and the like. Examples of lumiphoric materials are disclosed, for example, in U.S. Pat. No. 6,600,175 and in U.S. Patent Application Publication Nos. 2009/0184616 and 2012/0306355, and methods for coating light emitting elements with phosphors are disclosed in U.S. Patent Application Publication No. 2008/0179611, with the foregoing publications being incorporated by reference. Examples of phosphors that may be used according to certain embodiments include, without limitation, cerium (III)-doped yttrium aluminum garnet (Ce:YAG or YAG:Ce); yttrium aluminum oxide doped with cerium yttrium aluminum garnet (NYAG); lutetium aluminum garnet (LuAG), green aluminate (GAL, including but not limited to GAL535); $(Sr,Ba,Ca)_2$-$xSiO_4$:$Eu_x$ (BOSE, including both BOSE yellow and BOSE green varieties, including for example $(Ba,Sr)_2SiO_4$:$Eu^{2+}$); and CASN ($CaAlSiN_3$:$Eu^{2+}$).

The expressions "lighting device" and "light emitting device" as used herein are not limited, except that such elements are capable of emitting light. That is, a lighting device can be a device which illuminates an area or volume, e.g., a structure, a swimming pool or spa, a room, a warehouse, an indicator, a road, a parking lot, or a vehicle, signage, (e.g., road signs or a billboard), a ship, a toy, a mirror, a vessel, an electronic device, a boat, an aircraft, a stadium, a computer, a remote audio device, a remote video device, a cell phone, a tree, a window, a LCD display, a cave, a tunnel, a yard, a lamppost, or a device or array of devices that illuminate an enclosure, or a device that is used for edge or back-lighting (e.g., a backlight poster, signage, LCD displays), light bulbs, bulb replacements (e.g., for replacing AC incandescent lights, low voltage lights, fluorescent lights, etc.), outdoor lighting, street lighting, security lighting, exterior residential lighting (wall mounts, post/column mounts), ceiling fixtures/wall sconces, under cabinet lighting, lamps (floor and/or table and/or desk), landscape lighting, track lighting, task lighting, specialty lighting, ceiling fan lighting, archival/art display lighting, high vibration/ impact lighting-work lights, etc., mirrors/vanity lighting, or any other light emitting devices. An illuminated area may include at least one of the foregoing items. In certain embodiments, lighting devices as disclosed herein may be self-ballasted. In certain embodiments, a light emitting device may be embodied in a light bulb or a light fixture. In certain embodiments, a "lighting system" may include one lighting device or multiple lighting devices. In preferred embodiments, a "solid state lighting device" is devoid of any incandescent light emitting element. In certain embodiments, lighting devices or light emitting apparatuses as disclosed herein may be self-ballasted. In certain embodiments, a light emitting apparatus may be embodied in a light fixture.

Methods include illuminating an object, a space, an area, or an environment, utilizing one or more lighting devices or lighting systems as disclosed herein. Subject matter herein also relates in certain embodiments to an illuminated enclosure (the volume of which can be illuminated uniformly or non-uniformly), comprising an enclosed space and at least one lighting device or light emitting apparatus as disclosed herein, wherein at least one lighting device or light emitting apparatus illuminates at least a portion of the enclosure (uniformly or non-uniformly).

Subject matter herein further relates to an illuminated area comprising at least one item selected from among the group consisting of a structure, a swimming pool or spa, a room, a warehouse, an indicator, a road, a parking lot, a vehicle, signage (e.g., road signs), a billboard, a ship, a toy, a mirror, a vessel, an electronic device, a boat, an aircraft, a stadium, a computer, a remote audio device, a remote video device, a cell phone, a tree, a window, a LCD display, a cave, a tunnel, a yard, a lamppost, etc., having mounted therein or thereon at least one lighting device or light emitting apparatus as described herein. Methods include illuminating an object, a space, or an environment, utilizing one or more lighting devices or light emitting apparatuses as disclosed herein. In certain embodiments, a lighting apparatus as disclosed herein includes multiple groups of solid state light emitters (e.g., LEDs, with one or more LEDs optionally arranged to stimulate emissions of one or more lumiphors) arranged in an array (e.g., a two-dimensional array).

In certain embodiments, control of one or more solid state light emitter groups or sets may be responsive to a control signal (optionally including at least one sensor arranged to sense electrical, optical, and/or thermal properties and/or environmental conditions), a timer or clock signal, and/or at least one user input. One or more control signals may be provided to at least one current supply circuit. In various embodiments, current to different circuits or circuit portions may be pre-set, user-defined, or responsive to one or more inputs or other control parameters.

Various substrates may be used as mounting elements on which, in which, or over which multiple solid state light emitters (e.g., emitter chips) may be arranged or supported (e.g., mounted). Examples of suitable substrates include printed circuit boards (including but not limited to metal core printed circuit boards, flexible circuit boards, dielectric laminates, and the like) having electrical traces arranged on one or multiple surfaces thereof. A substrate, mounting plate, or other support element may include a printed circuit board (PCB), a metal core printed circuit board (MCPCB), a flexible printed circuit board, a dielectric laminate (e.g., FR-4 boards as known in the art) or any suitable substrate for mounting LED chips and/or LED packages.

In certain embodiments, one or more LED components can include one or more "chip-on-board" (COB) LED chips and/or packaged LED chips that can be electrically coupled or connected in series or parallel with one another and mounted on a portion of a substrate. In certain embodiments, COB LED chips can be mounted directly on portions of substrate without the need for additional packaging.

Certain embodiments may involve use of solid state light emitter packages. A solid state light emitter package may include at least one solid state light emitter chip (more preferably multiple solid state light emitter chips) that is enclosed with packaging elements to provide environmental protection, mechanical protection, color selection, and/or light focusing utility, as well as electrical leads, contacts, and/or traces enabling electrical connection to an external circuit. One or more emitter chips may be arranged to stimulate one or more lumiphoric materials, which may be coated on, arranged over, or otherwise disposed in light receiving relationship to one or more solid state light emitters. At least one lumiphoric material may be arranged to receive emissions of at least some emitters of a plurality of solid state light emitters and responsively emit lumiphor emissions. A lens and/or encapsulant material, optionally including lumiphoric material, may be disposed over solid state light emitters, lumiphoric materials, and/or lumiphor-containing layers in a solid state light emitter package.

In certain embodiments, a solid state lighting device (e.g., package) may include a reflector cup defining a cavity, at least one solid state light emitter arranged within the cavity, and encapsulant material arranged within the cavity. In certain embodiments, at least one solid state light emitter may be arranged over a substrate and at least partially surrounded by a boundary wall (optionally embodying at least one dispensed dam material laterally spaced from the emitter(s)), with an encapsulant material arranged over the emitter(s) and in contact with the at least one boundary wall.

Disclosed herein are lighting devices and lighting systems with adjustable operation of multiple independently controllable groups of solid state light emitters (e.g., LEDs) of different dominant wavelengths, wherein operation of the groups of solid state light emitters is automatically adjusted by at least one processor of a lighting device to provide desired illumination. In at least certain embodiments, operation of the groups of solid state light emitters is subject to being further affected by various sensors and/or user input commands. Operation of solid state light emitters or groups thereof may be altered to adjust one or (preferably) multiple light output parameters of aggregate emissions. Examples of light output parameters that may be adjusted include: color point of aggregate emissions, CCT of aggregate emissions, spectral content of aggregate emissions, brightness or luminous flux of emissions, and operating time. In certain embodiments, a lighting device includes multiple independently controllable emitters (or groups of solid state light emitters) having different color points. By altering proportion of current to different emitters or emitter groups having different color points, operation of a lighting device may be adjusted to adjust multiple lighting output parameters, including production of aggregate emissions having a wide range of different colors points and/or CCT values. In certain embodiments, spectral content of aggregate emissions at a particular color point or CCT may be adjusted to alter saturation/vividness (e.g., Qg) and/or melatonin suppression characteristics.

Multiple Independently Controllable Groups of Solid State Light Emitters

It is well known to adjust proportions of light output by three differently colored light sources (e.g., red, green, and blue) to permit adjustment of color point or CCT as well as aggregate flux (brightness). Once a desired color point or CCT of aggregate emissions is attained, however, the only parameter that can be adjusted is aggregate flux (brightness) without causing the color point to shift.

In certain embodiments, lighting devices as disclosed herein may include at least five groups of solid state light emitters, wherein each group is arranged to generate emissions comprising a dominant wavelength that differs from a dominant wavelength of emissions generated by each other group, each group is independently controllable, and emissions generated by each group are arranged to be combined to produce aggregate emissions of the lighting device. In certain embodiments, at least five groups of solid state light emitters separately include red, green, short wavelength blue, long wavelength blue (or cyan), and blue-shifted yellow (also referred to as "white") emitters. In certain embodiments, at least five groups of solid state light emitters include: a first group comprising at least one solid state light emitter arranged to generate emissions including a peak wavelength in a range of from 591 nm to 650 nm, a second group comprising at least one solid state light emitter arranged to generate emissions including a peak wavelength in a range of from 506 nm to 560 nm, a third group comprising at least one solid state light emitter arranged to generate emissions including a peak wavelength in a range of from 390 nm to 460 nm, a fourth group comprising at least one solid state light emitter arranged to generate emissions including a peak wavelength in a range of from 461 nm to 505 nm, and a fifth group comprising at least one solid state light emitter arranged to generate emissions including a peak wavelength in a range of from 430 nm to 480 nm and further arranged to stimulate emissions of a yellow- or green-emitting lumiphoric material arranged to generate emissions including a peak wavelength in a range of from 530 nm to 590 nm.

As compared to devices that consist of only red, green, and blue emitters, the addition of BSY (or "white") emitters permit more lumens to be generated at higher luminous efficacy for aggregate color points in the general vicinity of the white region of a chromaticity diagram. Shifting lumens from the red, green, and blue emitters to a BSY emitter also permits the red, green, and blue emitters to be used to a greater extent for tuning of light output parameters such as vividness (e.g., relative gamut) and/or melatonin suppression effects.

Additionally, as compared to devices that consist of only a red, a green, and a blue emitter, providing both a short wavelength blue and a long wavelength blue (or cyan) solid state light emitter permits tunability to control melatonin suppression effects, to control vividness, and/or enhance CRI. In certain embodiments, a short wavelength blue solid state light emitter is arranged to generate emissions including a peak wavelength in a range of from 390 nm to 460 nm (with the 390 nm lower boundary optionally being replaced with 400 nm, 410 nm, 420 nm, 430 nm or 440 nm in certain embodiments), and a long wavelength blue solid state light emitter is arranged to generate emissions including a peak wavelength in a range of from 461 nm to 505 nm (or in a subrange of from 470 nm to 489 nm, or in a subrange of from 470 nm to 480 nm, or in a subrange of from 472 to 475 nm, or another subrange specified herein). A greater amount of lumens may be provided by a short wavelength blue if desired to increase vividness, whereas a greater amount of lumens may be provided by a longer wavelength blue if desired to increase melatonin suppression effects.

In certain embodiments, vividness (e.g., relative gamut) and/or melatonin suppression effects may be altered without dramatically changing color point and/or luminous flux— thereby permitting vibrancy of color of illuminated surfaces and objects to be adjusted, but in a manner whereby a viewer is not alerted (e.g., through perceptible change in color point or intensity) to the adjustment. Adjusting operation of a lighting device to alter relative gamut may permit selective illumination of a space, an object, or a surface with enhanced vividness light.

In certain embodiments, increased saturation or vividness (including but not limited to increased Qg) can be achieved or enhanced with the use of long wavelength red LEDs. To consider the effect of red solid state light emitter wavelengths on Qg, various "BSY+R" devices (each including a blue LED arranged to stimulate a yellow or yellow-green phosphor, in combination with a supplemental red LED) were constructed. Six BSY+R devices each included a 450 nm dominant wavelength blue LED arranged to stimulate a 2:1 green:yellow mixture of LuAG/NYAG phosphors with addition of a LED of a different dominant wavelength (namely, 605 nm, 610 nm, 615 nm, 623 nm, 628 nm, and 633 nm). Such devices were compared to a baseline 90 CRI Cree EZW XTE device embodying blue LEDs arranged to pump a mixture of yellow and red phosphors. Chromaticity, gamut area, color rendering, and luminous efficacy characteristics of the six different types of BSY/G+R LED lighting devices were compared to the baseline BS(Y+R) LED lighting device. Each device had a CCT near 3050K, and had a color point near the BBL (e.g., Duv of no greater than +/−0.00051). The baseline BS(Y+R) device exhibited a blue peak wavelength of 455 nm and a red peak wavelength of 618 nm. Each BSY/G+R device exhibited a blue peak wavelength of 446 nm or 447 nm, and red peak wavelengths of 612 nm, 619 nm, 623 nm, 627 nm, 642 nm, and 643 nm (corresponding to dominant red wavelengths of 605 nm, 610 nm, 615, nm, 623 nm, a mix of 628 nm/633 nm, and 633 nm, respectively). Observations included: Qg increased with increasing red peak wavelength; CRI Ra was maximized near a red peak wavelength of 619 nm and declined significantly for longer red peak wavelengths; and CRI R9 was maximized near a red peak wavelength of 623 nm, and then declined significantly for longer red peak wavelengths.

In certain embodiments, a plurality of groups of solid state light emitters includes at least a sixth group of solid state light emitters.

In certain embodiments, at least six groups of solid state light emitters include the following: a first group comprising at least one solid state light emitter arranged to generate emissions including a peak wavelength in a range of from 591 nm to 617 nm, a second group comprising at least one solid state light emitter arranged to generate emissions including a peak wavelength in a range of from 506 nm to 560 nm, a third group comprising at least one solid state light emitter arranged to generate emissions including a peak wavelength in a range of from 390 nm to 460 nm, a fourth group comprising at least one solid state light emitter arranged to generate emissions including a peak wavelength in a range of from 461 nm to 505 nm, a fifth group comprising at least one solid state light emitter arranged to generate emissions including a peak wavelength in a range of from 430 nm to 480 nm and further arranged to stimulate emissions of a yellow- or green-emitting lumiphoric material arranged to generate emissions including a peak wavelength in a range of from 530 nm to 590 nm, and a sixth group comprising at least one solid state light emitter arranged to generate emissions including a peak wavelength in a range of from 618 nm to 650 nm. The foregoing six groups of solid state light emitters includes groups that may be described as (1) short wavelength red, (2) green/yellow, (3) short wavelength blue, (4) long wavelength blue (or cyan), (5) blue-shifted yellow (also referred to as 'white'), and (6) long wavelength red. Generally, solid-state light sources (e.g., LEDs) having different dominant wavelengths in the red range generally decline in luminous efficacy with increasing dominant wavelength, such that significantly more current may be required to generate the same number of red lumens from a red LED having a long dominant wavelength in the red range than from a red LED having a shorter dominant wavelength. Thus, providing both a long wavelength red and a short wavelength red permits a greater amount of long wavelength red light to be provided when increased vividness is required (but at the expense of luminous efficacy), and permits a greater amount of short wavelength red light to be provided when increased saturation (vividness) is not required and thereby avoid a reduction of luminous efficacy.

In certain embodiments, additional tuning of aggregate light output characteristics may be provided with addition of an independently controllable green emitter group. In certain embodiments, at least six groups of solid state light emitters include: a first group comprising at least one solid state light emitter arranged to generate emissions including a peak wavelength in a range of from 591 nm to 650 nm, a second group comprising at least one solid state light emitter arranged to generate emissions including a peak wavelength in a range of from 506 nm to 560 nm, a third group comprising at least one solid state light emitter arranged to generate emissions including a peak wavelength in a range of from 390 nm to 460 nm, a fourth group comprising at least one solid state light emitter arranged to generate emissions including a peak wavelength in a range of from 461 nm to 505 nm, a fifth group comprising at least one solid state light emitter arranged to generate emissions including a peak wavelength in a range of from 430 nm to 480 nm and further arranged to stimulate emissions of a yellow- or green-emitting lumiphoric material arranged to generate emissions including a peak wavelength in a range of from 530 nm to 590 nm, and a sixth group comprising at least one solid state light emitter arranged to generate emissions including a peak wavelength in a range of from 510 nm to 544 nm (e.g., such as may include a blue solid state light emitter arranged to stimulate emissions of a lumiphoric material to produce a green output), wherein at least one of a peak wavelength and a full width-half maximum intensity of emissions differs between the at least one solid state light emitter of the sixth group and the at least one solid state light emitter of the second group. The foregoing six groups of solid state light emitters includes groups that may be described as (1) red, (2) green/yellow, (3) short wavelength blue, (4) long wavelength blue (or cyan), (5) blue-shifted yellow (also referred to as 'white'), and (6) green. If a lumiphor converted solid state light emitter is used for the sixth group, then a saturated green color is preferably provided by increasing the amount of lumiphoric material to ensure the output of primarily phosphor-converted emissions). In certain embodiments, the sixth group may include a green LED devoid of a lumiphoric material; however, lumiphor-converted emissions may be preferred to promote enhanced luminous efficacy. Providing a sixth separately controllable group of emitters including a green emitter (e.g., having a peak wavelength in a range of from 510 nm to 544 nm) that differs from a peak wavelength of the second group permits enhance tunability of various saturation or vividness characteristics of aggregate emissions (e.g., GAI, Qg, or the like).

In certain embodiments, increased saturation (including but not limited to increased Qg) can be achieved or enhanced with the use of relatively narrow spectral output green lumiphors. Such increased saturation may be instead of or in addition to a long wavelength LED as described previously herein. In certain embodiments, a relatively narrow spectrum yellow or green lumiphor may include a peak wavelength preferably in a range of from 510 nm to 570 nm (or from 510 nm to 544 nm) and a full width-half maximum (FWHM) intensity value of less than 90 nm, of less than 80 nm, of less than 75 nm, of less than 70 nm, or of less than 65 nm. In certain embodiments, a narrow spectrum green lumiphor is preferred. One example of a narrow spectral output green lumiphor is BOSE (BG201B) phosphor having a peak wavelength of about 526 nm and a FWHM intensity value of about 68, relative to a FWHM intensity value of approximately 100 for GAL535 (a LuAG-type green phosphor). Another example of a narrow spectral output green lumiphor includes green quantum dots, which are tiny particles or nanocrystals of light-emitting semiconductor materials.

In certain embodiments wherein a lighting device includes a plurality of separately controllable groups of solid state light emitters, each group includes at least one solid state light emitter. In certain embodiments, each group includes at least two solid state light emitters having substantially the same peak wavelength. For example, FIG. 4A shows five groups of LEDs G1 to G5, indicated as R (red), G (green), B (short wavelength blue), W (white), and CY (cyan, or alternatively long wavelength blue), respectively. In certain embodiments, each group includes multiple solid state light emitters having a substantially identical peak wavelength (e.g., within ±1%) and/or substantially identical full width-half maximum spectral output (e.g., within ±8%, ±5%, ±3%, ±2%, or ±1%). In certain embodiments, intra-group variation of peak wavelength at an operating temperature of 85° C. is within a range of less than about ±4 nm, or within a range of less than about ±3 nm, or within a range of less than about ±2 nm, or within a range of less than about ±1 nm. In certain embodiments, different groups may include different numbers of solid state light emitters, or different groups may include the same number of solid state light emitters.

In certain embodiments, a plurality of groups of solid state light emitters is arranged in a two-dimensional array, such as (but not limited to) with each emitter arranged on a single substrate or support surface, or with each emitter arranged on multiple substantially coplanar substrates or support surfaces. In other embodiments, subsets of a plurality of group of emitters may be arranged on different substrates or support surfaces that are non-coplanar relative to one another. In certain embodiments, when a plurality of groups of solid state light emitters is supported by multiple different substrates or support surfaces (which may or may not be coplanar), each different substrate or support surface preferably includes solid state light emitters of at least two, at least three, at least four, at least five, or at least six different peak wavelengths. If multiple substrates or support surfaces are present, then by providing multiple solid state light emitters having different peak wavelengths on multiple different substrates or support surfaces, spatial differences in color uniformity may be reduced. In certain embodiments, a lighting device includes multiple substrates or support surfaces and a plurality of groups of solid state light emitters wherein different groups of solid state light emitters have peak wavelengths that differ between the respective groups, and each substrate or support surface includes at least one solid state light emitter of each group of the plurality of groups of solid state light emitters. In certain embodiments, a substrate or support surface can be provided in a small or large form factor in any desired shape (e.g., square, rectangular round, non-square, non-round, symmetrical and/or asymmetrical).

Figure 4B:
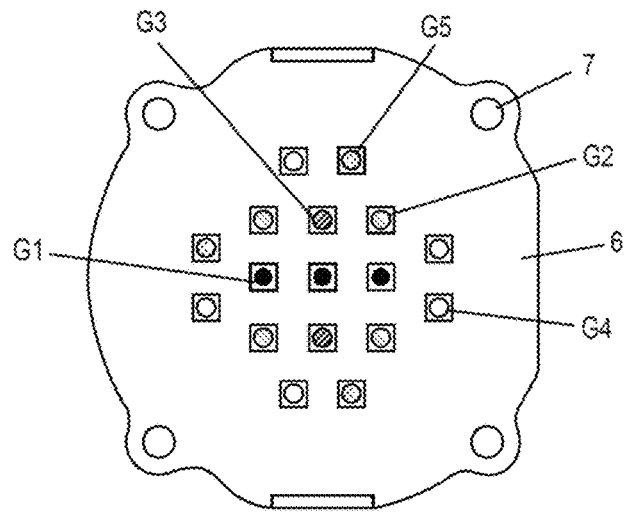
FIG. 4B illustrates a LED module including five groups of LEDs arranged in a two-dimensional array and mounted to a substrate, wherein the groups of LEDs are separately arranged to emit short wavelength blue, red, long wavelength blue (or cyan), green, and white (or blue-shifted yellow) light.

FIG. 4B shows five groups of LEDs G1-G5, with the five groups G1-G5 embodying red, green, short wavelength blue, white, and long wavelength blue (or cyan) LEDs, respectively. LEDs of the various groups G1-G5 are interspersed with one another to promote light mixing and are mounted in a two-dimensional array on a single substrate 6. The substrate 6 may embody a printed circuit board coated with a diffusively reflective material, and may include mounting holes 7. The first LED group G1 includes three red LEDs arranged in a linear pattern, the second LED group G2 includes four green LEDs arranged in a square pattern around the red LEDs, the third LED group G3 includes two short wavelength blue LEDs arranged between respective green LEDs, the fourth LED group G4 includes five white LEDs peripherally arranged around the red, green, and short wavelength blue LEDs, and the fifth LED group G5 includes three long wavelength blue LEDs interspersed among the white LEDs and peripherally arranged around the red, green, and short wavelength blue LEDs.

Figure 2:
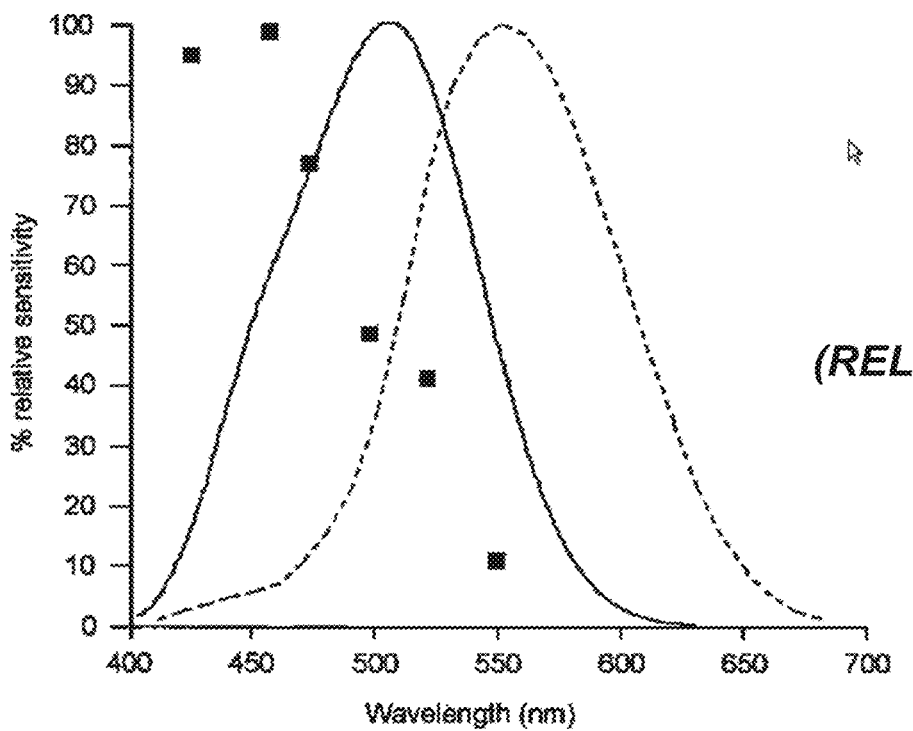
FIG. 2 is a line chart showing superimposed plots of the visible light portion of the melatonin action spectrum (at left), the scotopic response curve (at center), and the photopic response curve (at right), depicting % relative sensitivity as a function of wavelength.
Figures 3, 5A, 5B:
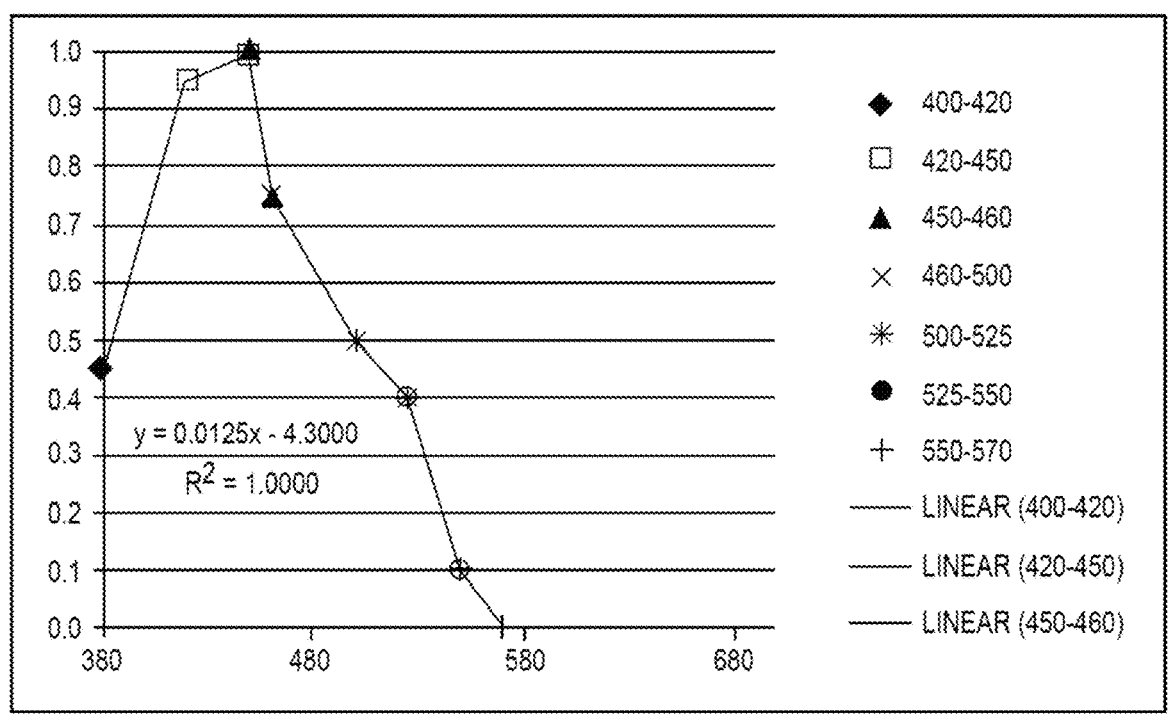
FIG. 3 is a table providing CCT values for various daylight sources.
FIG. 5A is a table including values for the melatonin action spectrum (relative units) and corresponding wavelengths.
FIG. 5B is a line chart for melatonin action spectrum showing the values depicted in FIG. 5A.

In certain embodiments, a plurality of groups of solid state light emitters may be used to affect melatonin suppression effects. As noted previously, FIG. 2 includes six data points along the visible light portion of the melatonin action spectrum (a/k/a the melatonin affecting region). By integrating the amount of light (milliwatts) within the melatonin action spectrum and dividing such value by the number of photopic lumens, a relative measure of melatonin suppression effects of a particular light source can be obtained. A scaled relative measure denoted "melatonin suppressing milliwatts per hundred lumens" may be obtained by dividing the photopic lumens by 100. The term "melatonin suppressing milliwatts per hundred lumens" or the abbreviations "msm/100 l" or "Mel mW/100 lumens" consistent with the foregoing calculation method are used elsewhere in this application and the accompanying figures. FIG. 5A is a table including values for the melatonin action spectrum (relative units) and corresponding wavelengths, while FIG. 5B is a line chart for melatonin action spectrum showing the values depicted in FIG. 5A.

Figures 6, 7:
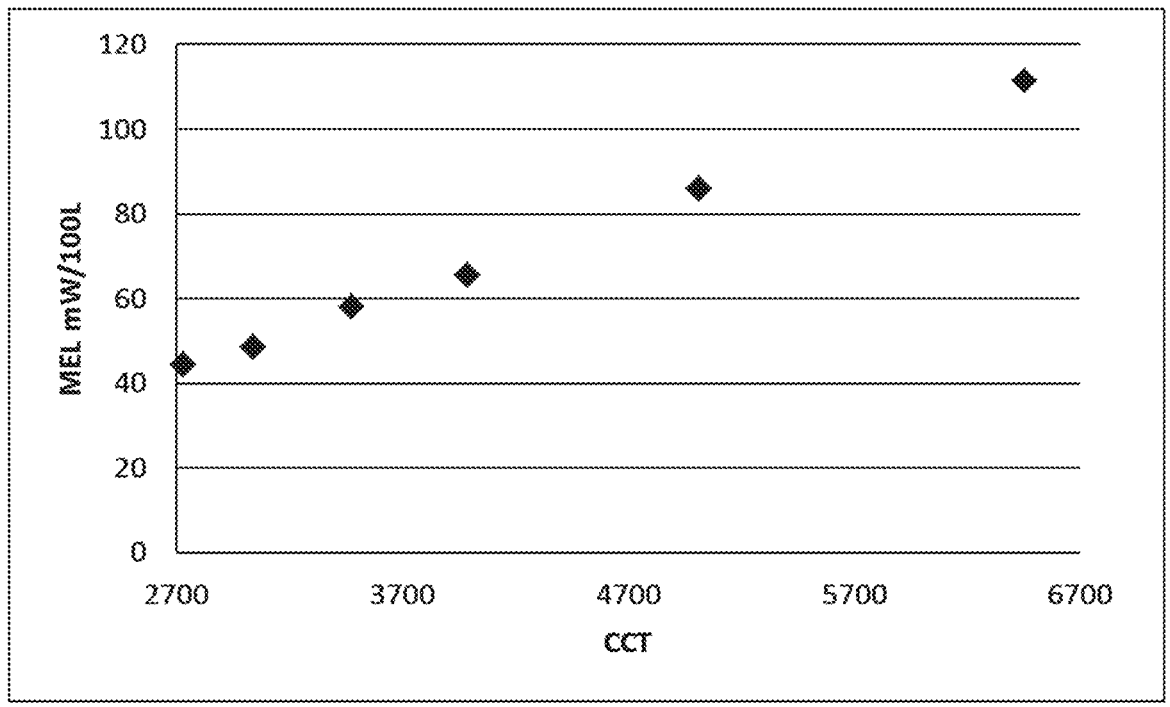
FIG. 6 is a table including correlated color temperature (CCT), color rendering index (CRI), and melatonin suppressing milliwatts per 100 lumens values for various light sources.
FIG. 7 is a plot of melatonin suppressing milliwatts per 100 lumens versus CCT obtained by modeling a solid state light source including a blue LED arranged to stimulate emissions of a yellow lumiphor in combination with a red LED, showing increasing milliwatts per 100 lumens with increasing CCT.
Figures 12A, 12B:
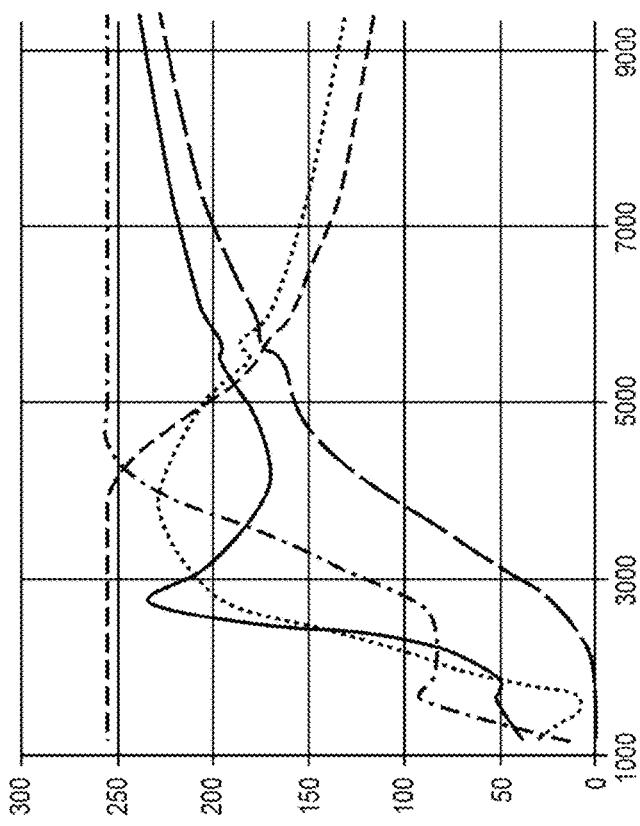
FIG. 12A is a table identifying emitter control step (within a range of from 0 to 255), brightness setting, luminous efficacy, CRI, Qg, maximum lumens, GAI, and CQS values for a lighting device including five groups of LEDs (red, blue-shifted yellow (white), green, long wavelength blue or cyan, and short wavelength blue) operated at sixteen different CCT values according to a "Vibrant" setting or instruction set.
FIG. 12B is an overlay plot of control step versus CCT for each of the five groups of LEDs of FIG. 12A.

FIG. 6 is a table including CCT, CRI, and msm/100 l values for various light sources. As shown in FIG. 6, an incandescent lamp provides a very high CRI value (~100) at full brightness, provides a relatively low msm/100 l value (~54) at such condition, but provides a much lower msm/100 l value (~25) when dimmed significantly. A Cree True-White® LED CR6 (including a blue LED arranged to stimulate emission of a yellow phosphor in combination with a red LED) performs similarly to an incandescent lamp, providing a CRI value (~93) and msm/100 l value (~46) at full brightness, with a reduced msm/100 l value (~27) when dimmed significantly. Generally increasing msm/100 l values (provided in parentheses) are obtained from lighting apparatuses of the following types: metal halide (72), tri-phosphor fluorescent (66), standard fluorescent (80), Cree cool white EasyWhite® LED including a blue LED arranged to stimulate emissions of both yellow and red phosphors (90), sun on a white wall (120), daylight fluorescent (125), and blue sky (200). FIG. 6 is a plot of melatonin suppressing milliwatts per 100 lumens versus CCT obtained by modeling a solid state light source including a blue LED arranged to stimulate emissions of a yellow lumiphor in combination with a red LED, showing increasing milliwatts per 100 lumens with increasing CCT. As is apparent from FIGS. 6 and 7, msm/100 l values generally increase with increasing CCT, which is as to be expected, since increasing CCT corresponds to increased blue content, and the melatonin response spectrum has a peak value in the long wavelength portion (460-480 nm) of the blue range. Although FIG. 6 demonstrates that msm/100 l values may be altered by substituting light sources having different CCT values, individual light sources referenced in FIG. 6 are generally not capable of permitting adjustment of msm/100 l values at a substantially constant CCT value.

In contrast to the lighting sources referenced in FIG. 6 or a conventional RGB light source, lighting devices according to various embodiments herein including more than three (e.g., preferably at least five, or at least six) groups of solid state light emitters arranged to emit light of different peak wavelengths permit adjustment of msm/100 l values at a substantially constant color point or CCT value. In certain embodiments, a lighting device may provide adjustable CCT output, and further provide adjustable msm/100 l at different CCT values.

Consistent with the preceding discussion, in certain embodiments, at least one processor of a lighting device is arranged to adjust, responsive to the at least one detector output signal and for a selected color point or CCT of the aggregated emissions, at least one of (i) melatonin suppressing milliwatts per hundred lumens of the aggregate emissions and (ii) relative gamut of the aggregate emissions. In certain embodiments, such adjustments may be performed while maintaining aggregate emissions at or near a target color point or CCT value (and/or at or near a desired luminous flux), preferably while maintaining aggregate emissions above a desired threshold. In certain embodiments, at least one processor of a lighting device is configured (e.g., responsive to a user command or steps of an instruction set or algorithm) to perform at least one of the following adjustments (i) and (ii) while maintaining at least one (or more preferably both) of the following conditions (iii) and (iv): (i) adjust melatonin suppressing milliwatts per hundred lumens of the aggregate emissions by at least 10% (or at least 20%), and (ii) adjust relative gamut of the aggregate emissions by at least 8% (or at least 15%), (iii) maintain aggregate emission of the lighting device within four MacAdam ellipses of a target CCT value, and (iv) maintain aggregate emissions of the lighting device at or above a color rendering index (CRI) value of at least 70. In certain embodiments, the target CCT value is selected from the range of from 2700K to 9000K.

Further details regarding adjustment of melatonin suppression effects are disclosed in U.S. Pat. No. 9,039,746, which is hereby incorporated by reference herein.

Temporal Alteration of Light Output Parameters

In certain embodiments, a lighting device includes multiple independently controllable emitters (or groups of solid state light emitters) having different color points, thereby permitting adjustment of various light output parameters. Examples of light output parameters that may be adjusted include: color point of aggregate emissions, CCT of aggregate emissions, spectral content of aggregate emissions, brightness or luminous flux of emissions, and operating time.

In certain embodiments, a lighting device may be arranged to utilize at least one operating instruction set or algorithm to automatically adjust one or more light output parameters at different hours of a calendar day. In certain embodiments, a lighting device knows the time of day and sets light output parameters (e.g., CCT and brightness) appropriately. In certain embodiments, such automatic adjustment may be responsive to time and/or to at least one signal indicative of an environmental condition. In certain embodiments, such automatic adjustment may be suspended or altered responsive to at least one user input signal, which may be received by at least one detector associated with a lighting device. In certain embodiments, an operating instruction set or algorithm may be automatically updated taking into account one or more temporal patterns of usage, which may be correlated to environmental condition information accumulated by and stored in memory of a lighting device.

In certain embodiments, an operating instruction set or algorithm to be executed by at least one processor of a lighting device permits automatic adjustment of one or more light output parameters at different hours of a calendar day, and is configured to promote wellness by providing output that promotes alertness in morning to afternoon hours, that promotes alertness and relaxation in mid-afternoon to evening hours, that promotes relaxation and sleepiness in late evening to bedtime hours, and that does not interfere with sleeping and/or does not interfere with night vision from midnight to dawn hours. FIG. 8 is a table identifying, for different times of day, ambient light, desired aptitude, and possible artificial light intensity levels and CCT values that may promote wellness when used with lighting devices and systems according to one embodiment of the disclosure. It is known that exposure to light of high intensity and high CCT promotes alertness; accordingly, a lighting device may output high intensity emissions of a CCT in excess of 6000K from dawn to mid-morning to promote wakefulness. As the day progresses, the illumination tends to match the outdoor light. A somewhat lower CCT (in a range of from 3500K to 5000K, or from 4000K to 5000K) with sustained high intensity may be output from mid-day through the afternoon to promote alertness. Progressing into the evening, a lighting device may output emissions of lower intensity and a lower (warmer) CCT (e.g., from 2000K to 3000K) with reduced blue spectral content to avoid melatonin suppression, and thereby promote relaxation prior to bedtime. In the middle of the night to dawn, a lighting device may output emissions of very low intensity and with a very low CCT (e.g., below 1500K) to avoid interference with sleep and avoid loss of night vision in case a person's sleep is interrupted. The preceding variation in intensity and CCT is controlled using at least one operating instruction set or algorithm stored in memory of a lighting device.

Figure 9:
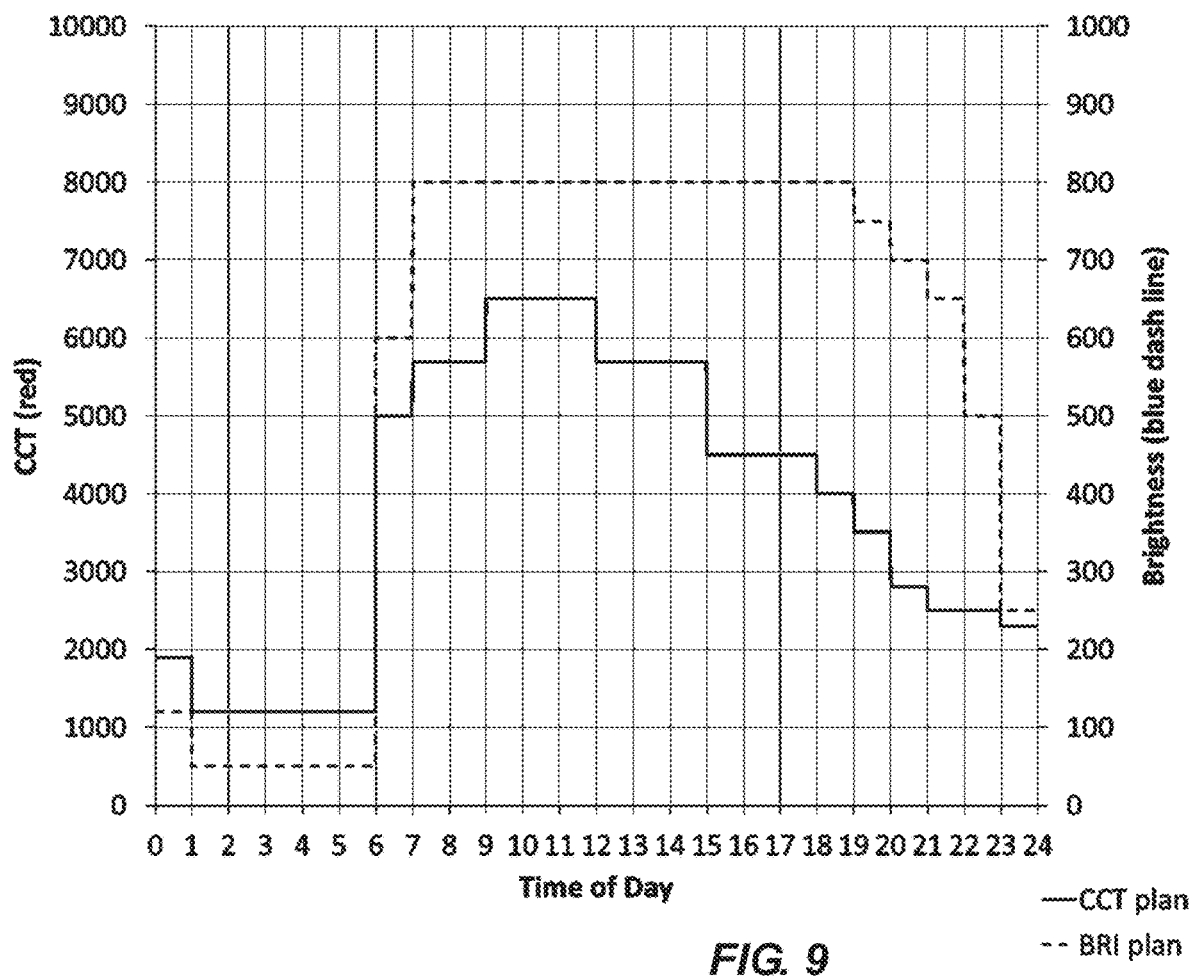
FIG. 9 is an overlay plot of possible CCT values and luminous flux (brightness) values as a function of time of day that may promote wellness when used with lighting devices and systems according to at least certain embodiments of the disclosure.

FIG. 9 is an overlay plot of possible CCT values and luminous flux (brightness) values as a function of time of day that may promote wellness when used with lighting devices and systems according to at least certain embodiments of the disclosure.

In certain embodiments, at least one operating instruction set or algorithm may be altered or programmed by a user, such as by using one or more user input elements. For example, a user that is required to work during evening hours and to sleep during daytime hours may seek to alter or create an operating instruction set or algorithm to output emissions having a high intensity and a high CCT during evening hours to promote alertness while the user is working, with a transition to lower intensity and lower CCT to a time allotted for the user to sleep. In certain embodiments, a user may simply shift a schedule contained in a predefined operating instruction set by a selected number of hours, based on a selected wake-up time, a selected time to bed, and/or a selected period for work or other activity requiring alertness.

Utilization of Sensors

In certain embodiments, a lighting device or lighting system includes at least one sensor arranged to receive or provide at least one signal indicative of one or more environmental conditions, and operation of the lighting device may be responsive to a signal received from at least one sensor. In certain embodiments, at least one environmental condition may include any one or more of: humidity, air pressure, ambient sound, gas concentration, presence or absence of gas, particulate concentration, presence or absence of particulates, temperature, cloud cover, outdoor ambient temperature, outdoor ambient light level, outdoor CCT, presence of precipitation, type of precipitation, UV index, solar radiation index, moon phase, moonlight light level, presence of aurora, and chill factor. In certain embodiments, at least one sensor arranged to receive or provide at least one signal indicative of an environmental condition may include one or more of: an ambient light sensor, an image sensor, a temperature sensor, a barometric pressure sensor, a humidity sensor, a weather information receiver, a gas detector, and a particulate detector.

In certain embodiments, a lighting device may utilize an output signal received from at least one sensor to compensate for presence, absence, intensity, and/or color point of natural ambient light.

In certain embodiments, a lighting device or lighting system includes, or is arranged in at least intermittent communication with, a light sensor arranged to receive ambient light (e.g., daylight) or other incident light. In certain embodiments, a light sensor may analyze or otherwise examine the spectral content of received light. In certain embodiments, such analysis or examination may include determining "naturalness" of received light (e.g., whether the received light embodies or includes spectral content consistent with daylight, or whether the received light is representative of artificial light). In certain embodiments, one or more sensors and/or detectors may be arranged in or on a body structure of a lighting device that additionally contains multiple separately controllable groups of solid state light emitters, and that preferably also contains a memory and at least one processor. In certain embodiments, a lighting device may additionally or alternatively be arranged to communicate with one or more remote sensors (or other remote input elements). Remote sensor(s) and/or remote input element(s) may be configured to communicate with one or more lighting devices via wired or wireless (e.g., RF, ultrasound, infrared, modulated light) means. In certain embodiments, signals from one or more remote sensors may be communicated to a lighting device via one or more wide area or local area networks. In certain embodiments, a remote sensor may include a remote weather station or remote information outlet, and a lighting device may be configured to receive environmental information from the weather station or information outlet via the Internet, a cellular network, or another wired and/or wireless network.

If provided, an ambient light sensor may take on different configurations. In a first configuration, an ambient light sensor may be separate from emitters of a lighting device and associated with control circuitry to facilitate monitoring of the ambient light characteristic. An ambient light sensor may be a specially configured light sensor or another LED that is configured to generate a current indicative of the ambient light characteristic in response to being exposed to the ambient light. If a plurality of LEDs are driven with pulses of current, then an ambient light characteristic may be monitored between any two pulses of current. Alternatively, one or more main LEDs may be used by control circuitry to monitor the ambient light characteristic, such as by monitoring ambient light between any two pulses of LED drive current.

In certain embodiments, a lighting device or lighting system may include an image sensor arranged to periodically capture one or more images of a surface or environment proximate to a lighting device or arranged to be illuminated by the lighting device, whereby usage of one or more captured images may be used to affect operation of the lighting device.

In certain embodiments, a lighting device or lighting system may include a sound sensor (e.g., a microphone) arranged to receive one or more sounds, such as in a space arranged to be illuminated by a lighting device.

If provided, an occupancy sensor (e.g., based on received electromagnetic radiation, light, sound, vibration, heat, or the like) may be used to determine a condition indicating presence or absence of at least one person in an illuminated space. In certain embodiments, detection of a condition indicating that an illuminated space is not occupied may be used to terminate or alter operation of a lighting device. In certain embodiments, a passive infrared sensor may be used for occupancy sensing.

The intensity and spectral output of the light emitted by electrically activated emitters (e.g., LEDs) may be affected by temperature. In certain embodiments, a temperature sensor associated with a lighting device may be used to sense temperature of one or more emitters, and current to the emitters may be controlled based on the sensed temperature in an effort to compensate for temperature effects.

In certain embodiments, one or more temperature sensors may be arranged on a lighting device or arranged remotely from a lighting device, and arranged to sense ambient temperature of an environment arranged to be illuminated by the lighting device. Ambient temperature apart from a lighting device may provide an indication as to the brightness and/or color point of artificial light that may be appropriate for a given time period. For example, a low temperature within an enclosed space subject to being periodically occupied by people may provide an indication of occupancy of the space. If a low temperature is sensed, then that may provide any indication that the space is not occupied.

Utilization of Detectors

As noted previously, automatic adjustment of one or more light output characteristics within a calendar day may be suspended or altered responsive to at least one user input signal (e.g., user commands), which may be received by at least one detector associated with a lighting device. In certain embodiments, a detector may produce at least one output signal, and operation of the lighting device may be suspended or altered responsive to the at least one output signal. In certain embodiments, one or more sensors as mentioned herein may be used as a detector, and conversely one or more detectors as mentioned herein may be used as a sensor.

In certain embodiments, a detector may be arranged to detect at least one user-initiated (e.g., wired or wireless) signal. Such a signal may be indicative of a user command. In certain embodiments, a detector may include a radio frequency (RF) receiver or transceiver (e.g., Bluetooth, ZigBee, WiFi, or the like), a modulated light receiver, an infrared receiver, or a sound receiver. In certain embodiments, a detector may be arranged to receive a signal (e.g., a wired or wireless signal) from a digital communication device or a digital computing device, such as a mobile phone, a personal computer, or the like. In certain embodiments, a detector may be arranged to receive a wireless signal from a dedicated remote controller or wireless communication hub. In certain embodiments, a detector may be arranged in or on a body structure of a lighting device.

In certain embodiments, a detector may be arranged to detect multiple different user-generated gesture patterns indicative of user commands. For example, a detector may include an image sensor including a field of view arranged to image a user. Upon receipt of specific gesture patterns (e.g., arm waving in a back and forth motion, a circular motion, a spreading motion, a contracting motion, etc.), the image sensor may compare such patterns against a predefined or user-defined gesture pattern set to determine if a match is identified, and responsively generate a detector output signal indicative of at least one user command.

In certain embodiments, a detector may be arranged to detect multiple different user-generated sound patterns indicative of user commands. For example, a detector may include a microphone arranged to receive clapping noises, snapping noises, vocalizations, and/or other user-generated sound patterns. Upon receipt of specific sound patterns (e.g., patterns of one or multiple claps within a specified time period, or specific words, or other sounds), received sounds may be processed (e.g., filtered, processed by a voice recognition, or the like) and compared against a predefined or user-defined sound pattern set to determine if a match is identified, and responsively generate a detector output signal indicative of at least one user command.

In certain embodiments, reception by a processor of a detector output signal indicative of a user command will cause the processor to alter at least one light output parameter. In certain embodiments, a lighting device may include memory arranged to store a log of received detector output signals, and such log may be retrieved by a user or automatically transmitted to a user, such as may be useful for troubleshooting and/or enhancing accuracy of user input signal recognition. In certain embodiments, reception by a processor of a detector output signal indicative of a user command may also cause the lighting device to initiate one or more actions to acknowledge receipt and/or content of the input signal, such as generating one or more sounds, initiating one or more flashes, blinks, or different colored light patterns.

Examples of light output parameters that may be altered upon detection of a user input signal include, but are not limited to the following: activating a lighting device, deactivating a lighting device, increasing or decreasing CCT, dimming a lighting device without CCT decay, dimming a lighting device with CCT decay, initiation or cessation of an enhanced vividness (or reduced vividness) mode, initiation or cessation of a color changing cycle, initiation or cessation of a music-linked color changing mode, and selection of one or more previously defined operating modes.

FIGS. 10A-10B embody a table identifying event name, system status, action, time, CCT, and brightness settings for an algorithm including instructions for operating a lighting device or lighting system according to one embodiment of the disclosure, wherein certain events enable light output parameters that may be altered upon detection of a user input signal. In the leftmost column of FIG. 10A, the first event is Apply Power. If the clock of the lighting device has not yet been set, then upon receipt of a signal (e.g., wall switch signal) applying power to the lighting device, solid state light emitters are turned on (i.e., the light is turned on) to attain a CCT of 3000K and a brightness level of 800 lumens. Once the clock is set, then the Apply Power function will automatically turn on the lighting device at sunrise at a CCT of 3000 and a brightness of 600. Operation of the lighting device will be automatically altered at different times of the day as shown in FIG. 10A (to generally increase CCT and brightness until a peak at 12:00 PM (noon), followed by a general reduction of CCT and brightness to minimum values at 1:00 AM) unless such automatic operation is altered by a signal received from at least one sensor or by a detected signal indicative of a user input command. For example, the second event in the leftmost column of FIG. 10A is Occupancy, which is substantially identical to the Apply Power event except that the light will automatically turn off after 15 minutes if no movement is detected in the vicinity of an occupancy sensor. However, if movement is detected thereafter, then the light will turn on automatically and resume operation according to the schedule of the Apply Power event. The third event in the leftmost column of FIG. 10A is the Sleep Command, which will cause the lighting device to reduce CCT (based on time of day), to reduce brightness by 80% (to a minimum value of 50), and then to turn off the light after a predetermined time (e.g., 20 minutes).

Although stepwise variation in light output parameters from hour to hour is depicted in FIG. 10A, it is to be appreciated that in certain embodiments variation in light output parameters may be more frequent, such as even on a substantially continuous basis.

FIG. 10B outlines various different clap command events and voice command events. The first clap command event in the leftmost column of FIG. 10B is the Clap command, in which detection of a single clap when the light is on will cause the light to dim with a decay, thereby reducing CCT to match CCT value at half the current brightness indicated in the Apply Power table, and reducing brightness by 50%. The second clap command event in the leftmost column of FIG. 10B is the Double Clap command, in which detection of a double clap when the light is on will cause the light to dim to 0 without a decay, thereby reducing brightness to 0 within 3 seconds. The third clap command event in the leftmost column of FIG. 10B is the Clap command, in which detection of a single clap when the light is off will cause the light to use the Apply Power event settings for brightness and CCT corresponding to the current time. The fourth clap command event in the leftmost column of FIG. 10B is the Double Clap command, in which detection of a double clap when the light is off will cause the light to be activated with brightness and power restored to the previous setting in use prior to deactivation.

The first voice command event in the leftmost column of FIG. 10B is the Lights On command, in which detection of a vocalization signal (e.g., speaking the words "Lights On") will cause the light to apply to use the Apply Power event settings for brightness and CCT corresponding to the current time. The second voice command event in the leftmost column of FIG. 10B is the Lights Off command, in which detection of a vocalization signal (e.g., speaking the words "Lights Off") will cause the light to turn off. The third voice command event in the leftmost column of FIG. 10B is the Lights Dim command, in which detection of a vocalization signal (e.g., speaking the words "Lights Dim") will cause the light to dim to half the brightness level in use at the time of receipt of the command. The fourth voice command event in the leftmost column of FIG. 10B is the Lights Cool command, in which detection of a vocalization signal (e.g., speaking the words "Lights Cool") will cause the light to increase CCT to a next higher CCT value set in memory of the lighting device. The fifth voice command event in the leftmost column of FIG. 10B is the Lights Warm command, in which detection of a vocalization signal (e.g., speaking the words "Lights Warm") will cause the light to decrease CCT to a next lower CCT value set in memory of the lighting device. The sixth voice command event in the leftmost column of FIG. 10B is the Lights Dance command, in which detection of a vocalization signal (e.g., speaking the words "Lights Dance") will cause the light to select (or select a next) colorful mode in which operation of the lighting device will follow an ongoing sound (e.g., music) signal received by the lighting device. The preceding commands represent only a few potential actions that could be implemented by a lighting device or lighting system according to embodiments of the present disclosure.

Operation in Different Color Rendering/Vividness Modes and Different CCTs

Figures 14A, 14B:
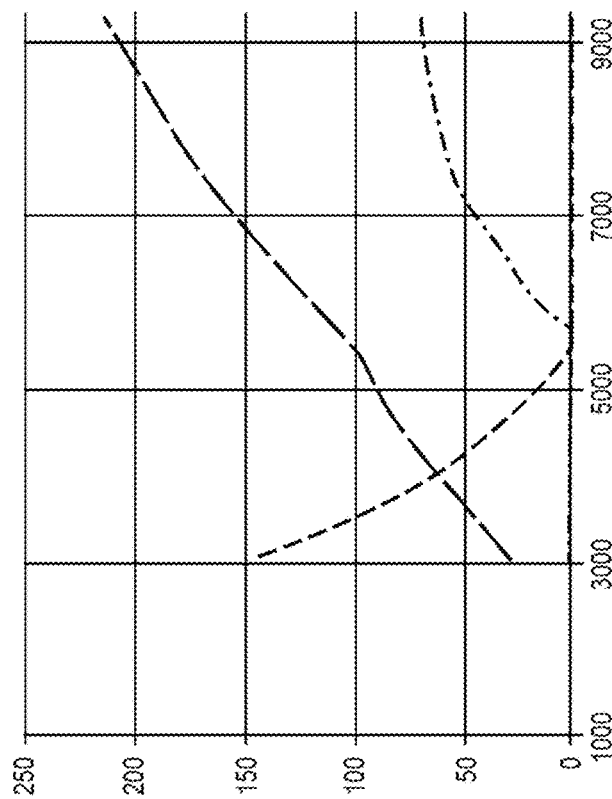
FIG. 14A is a table identifying emitter control step (within a range of from 0 to 255), brightness setting, luminous efficacy, CRI, Qg, maximum lumens, GAI, and CQS values for a lighting device including five groups of LEDs (red, blue-shifted yellow (white), green, long wavelength blue or cyan, and short wavelength blue) operated at eleven different CCT values according to a "Dull" or "Less Vibrant" setting or instruction set.
FIG. 14B is an overlay plot of control step versus CCT for each of the five groups of LEDs of FIG. 14A.

In certain embodiments, a lighting device or lighting system as disclosed herein may be operated in different modes configured to provide different color rendering or vividness/saturation of the aggregate light. Tables and corresponding plots for four different modes (identified as "High CRI," "Vibrant," "Very Vibrant," and "Dull") of operation of a lighting device including five groups of LEDs (red, blue-shifted yellow, green, long wavelength blue or cyan, and short wavelength blue) operated at multiple different CCT values are provided in FIGS. 11A-11B, FIGS. 12A-12B, FIGS. 13A-13B, and FIGS. 14A-14B, respectively. The tables of FIGS. 11A, 12A, 13A, and 14A each provide emitter control step (within a range of from 0 to 255), brightness setting, luminous efficacy, CRI, Qg, maximum lumens, GAI, and CQS for the lighting device. FIG. 11A (High CRI) and FIG. 12A (Vibrant) include data for sixteen different CCT values ranging from 1200K to 9412K, whereas FIG. 13A (Very Vibrant) includes data for ten different CCT values ranging from 2732K to 6525K, and FIG. 14A (Dull) includes data for eleven different CCT values ranging from 3045K to 9307K. As shown in FIGS. 11A-11B (High CRI), all five groups of solid state light emitters were operated at for all CCT values at or about 4000K. As shown in FIGS. 12A-12B and FIGS. 13A-13B (Vibrant and Very Vibrant), long wavelength blue emitters were not used at any CCT values, whereas FIGS. 14A-14B show that long wavelength blue emitters were not used at all, and green emitters were only used at very elevated CCT values.

Communication with and Between Lighting Devices

Figure 15:
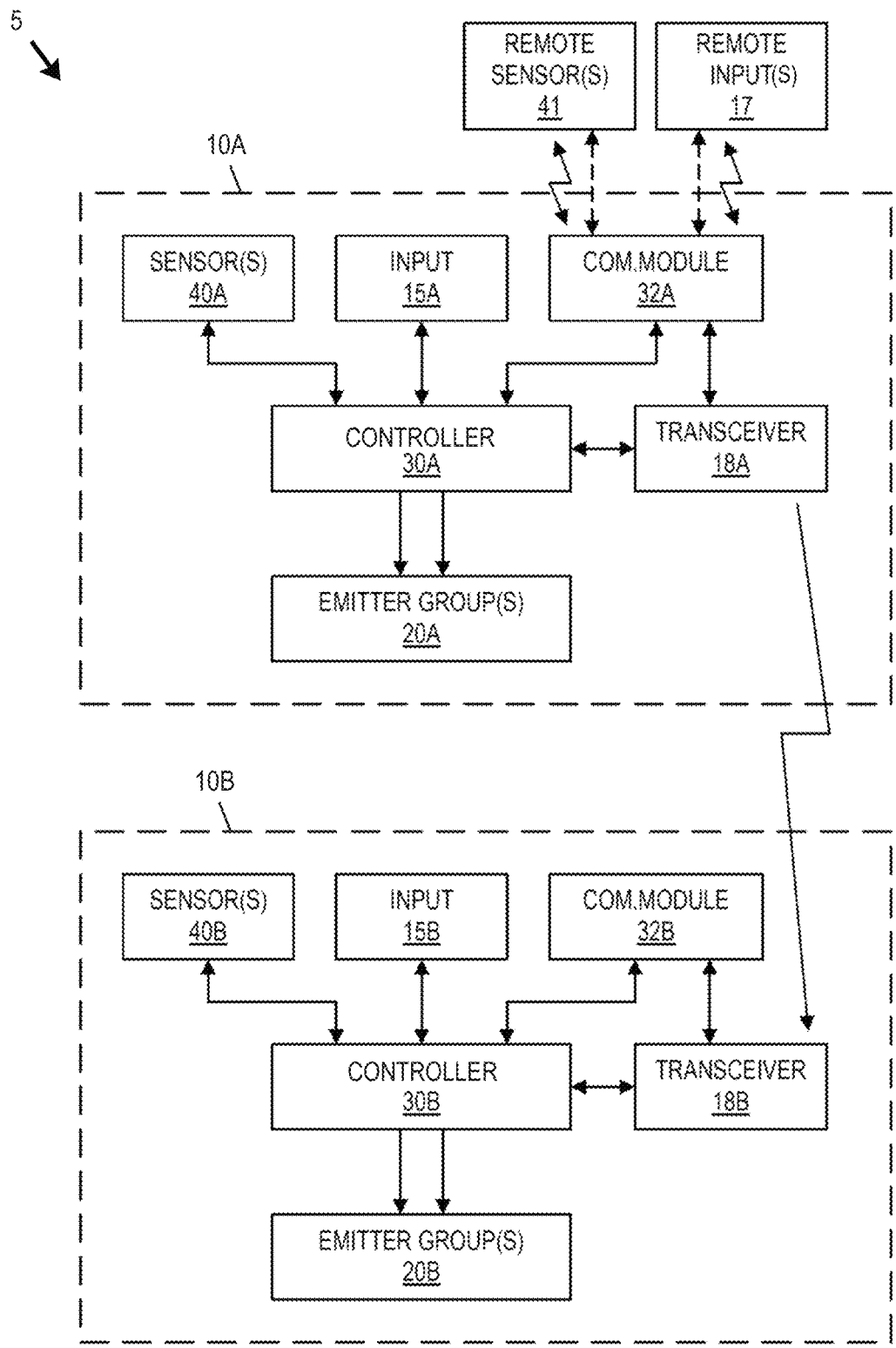
FIG. 15 is a block diagram of a lighting system according to one embodiment of the disclosure in which at least one lighting device is configured to bidirectionally communicate with at least one other lighting device as well as to communicate with a digital communication device or a digital computing device.

In certain embodiments, lighting devices may be arranged to communicate with other lighting devices and also with one or more sensors and user input elements (e.g., a digital communication device or a digital computing device), wherein multiple lighting devices in combination may work together as a lighting system. FIG. 15 is a block diagram of a lighting system 5 according to one embodiment of the disclosure in which at least one lighting device is configured to bidirectionally communicate with at least one other lighting device as well as to communicate with a digital communication device or a digital computing device. The first lighting device 10A includes a controller module 30A, one or more sensors 40A, a user input element 15A, a communication module 32A, a transceiver 18A, and one or more emitter groups 20A. The second lighting device 10B includes a controller module 30B, one or more sensors 40B, a user input element 15B, a communication module 32B, a transceiver 18B, and one or more emitter groups 20B. In certain embodiments, one or more remote sensors 41 and one or more remote input elements 17 may be arranged in at least intermittent communication with one or more of the lighting devices 10A, 10B.

Within each lighting device 10A, 10B, the respective emitter groups 20A, 20B preferably include multiple groups of electrically activated emitters, with different groups preferably arranged to output color points that differ between groups. By altering proportion of current to different emitters having different color points, a lighting device may be adjusted to produce aggregate emissions of a range of different color points and/or CCTs, as well as different spectral content at selected color points or CCTs. The controller module 30A, 30B of each lighting device 10A, 10B is arranged to drive emitters of emitter group(s) 20A, 20B of the respective lighting device 10A, 10B. In certain embodiments, the controller module 30A, 30B provides the primary intelligence for the respective lighting device 10A, 10B, and may include or be associated with driver circuits capable of driving emitters of the emitter groups 20A, 20B, in a desired fashion. Each controller module 30A, 30B may be embodied in a single, integrated module or divided into two or more sub-modules as desired. Each controller module 30A, 30B preferably includes at least one processor (e.g., microprocessor) and a memory.

When a controller module 30A, 30B provides the primary intelligence for its respective lighting device 10A, 10B, the communication module 32A, 32B may act as an intelligent communication interface to facilitate communications between the controller module 30A, 30B and one or more remote sensors 41 and/or one or more remote input elements 17. The remote sensor(s) 41 and/or remote input element(s) 17 may be configured to communicate with one or more lighting devices 10A, 10B in a wired or wireless fashion.

Alternatively, each controller module 30A, 30B may be primarily configured to drive emitters of its respective emitter group(s) 20A, 20B based on instructions from the respective communication module 32A, 32B. In such an embodiment, the primary intelligence of each lighting device 10A, 10B may be provided in the respective communication module 32A, 32B, which may embody an overall control module with wired or wireless communication capability. Each communication module 32A, 32B may include or have associated therewith at least one transceiver 18A, 18B, wherein each transceiver 18A, 18B may be optionally replaced with separate transmitter and receiver components. Each communication module 32A, 32B may facilitate the sharing of intelligence and signals among the various lighting devices 10A, 10B and other entities.

In certain embodiments, the functions of the controller module 30A, 30B and a transceiver 18A, 18B may be integrated in a single module (e.g., a Bluetooth microcontroller).

In certain embodiments, each communication module 32A, 32B may be implemented on a printed circuit board (PCB) that is separate from a circuit board associated with the respective controller module 30A, 30B. In certain embodiments, communication between a communication module 32A, 32B and a corresponding controller module 30A, 30B may be made via cables according to a desired communication interface, optionally including one or more interface plugs. In certain embodiments, each lighting device 10A, 10B may include a body structure, and the controller module 30A, 30B, communication module 32A, 32B, and emitter group(s) 20A, 20B of the respective lighting device 10A, 10B may be arranged in or on the body structure.

In certain embodiments, each lighting device 10A, 10B may include one transceiver arranged to permit communication between lighting devices 10A, 10B, and may include another transceiver arranged to permit communication between a lighting device 10A, 10B and a remote input element 17 preferably in the form of a digital computing device or a digital communication device.

Device Embodiments Controlling at Least Five LED Groups

Figure 16:
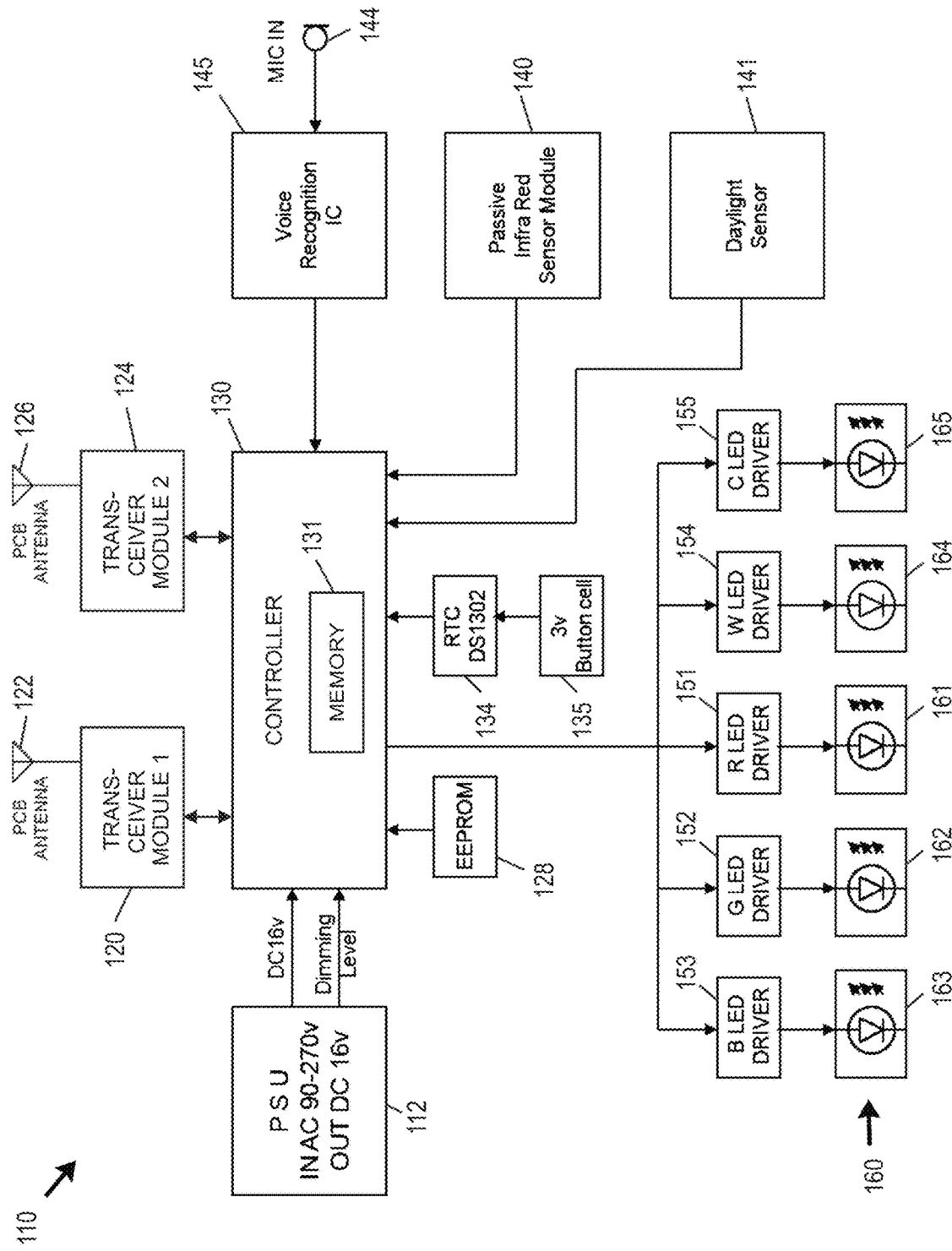
FIG. 16 is a block diagram identifying interconnections between various elements of a lighting device that is arranged to independently control five different groups of LEDs according to one embodiment of the disclosure.

FIG. 16 is a block diagram identifying interconnections between various elements of a lighting device 110 that is arranged to independently control five different groups of LEDs 161-165 according to one embodiment of the disclosure. The lighting device 110 includes a controller 130 (preferably embodied in a microcontroller or other microprocessor) that preferably includes an associated reprogrammable memory 131 that may be used to store one or multiple algorithms or other emitter operating instruction sets. The controller 130 may also have associated therewith an external memory 128 such as an EEPROM. A real time clock 134 (e.g., timekeeping chip) with an associated battery 135 may contain a real-time clock/calendar and communicate with the controller 130. A power supply unit 112 provides AC-DC power conversion utility. First and second transceivers 120, 124 each having an antenna 122, 126 may be arranged to separately communicate with (i) a digital communication device or a digital computing device, and (ii) another lighting device, respectively. A microphone 144 and associated voice recognition integrated circuit 145 may be used to receive user-generated sound patterns and determine whether such patterns are indicative of user commands. The microphone 144 may additionally be used to receive music signals as a basis for operating the lighting device 110 in a music-linked color changing mode. A passive infrared sensor module 140 may be used to detect motion and thereby occupancy in an area proximate to the lighting device 110. A daylight sensor 141 may be used to receive ambient or incident light, and operation of the lighting device 110 may be controlled responsive to a signal received from the daylight sensor 141 such as to compensate for presence, absence, intensity, and/or color point of ambient or incident light. The controller 130 is arranged to send signals to five LED driver modules 151-155 that are configured to generate a constant voltage and varying current signals for driving five LED groups 161-165.

In operation, the lighting device 110 is configured to receive or provide at least one signal indicative of an environmental condition via the daylight sensor 141. The memory 131 stores at least one algorithm or operating instruction set. Various user commands may be received via the first transceiver module 120 or the microphone 144. The controller 130 is configured to use at least one operating instruction set to automatically adjust luminous flux and/or color point (or CCT) of the aggregate emissions at different hours of a calendar day, in response to time and/or a signal received from or provided by the daylight sensor 141. Such adjustment is performed by controlling the LED driver modules 151-155 connected to the LED groups 161-165 that in certain embodiments collectively form a LED array 160. The controller 130 is configured to suspend or alter automatic adjustment of (a) luminous flux of the aggregate emissions and (b) at least one of CCT and color point of the aggregate emissions, responsive to detection of a user command. In certain embodiments, the controller 130 may be further configured to adjust at least one of (i) melatonin suppressing milliwatts per hundred lumens of the aggregate emissions and (ii) relative gamut of the aggregate emissions, for a selected color point or CCT of the aggregated emissions of the lighting device 110.

Figure 17:
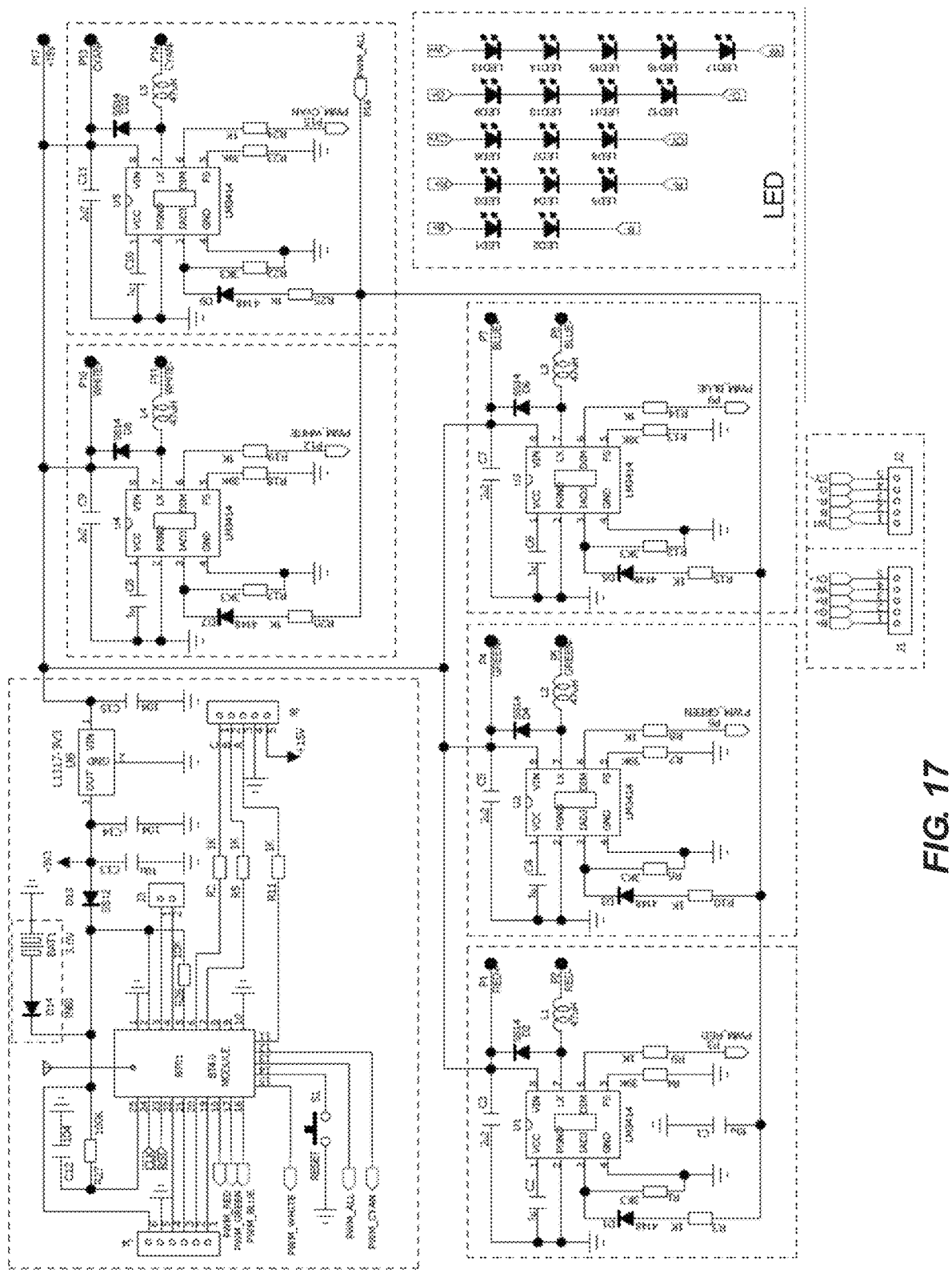
FIG. 17 is a circuit diagram for various elements of a lighting device arranged to independently control five different groups of LEDs according to one embodiment of the disclosure, with the circuit diagram including a processing/communication module and five driver modules.

FIG. 17 is a circuit diagram for various elements of a lighting device arranged to independently control five different groups of LEDs according to one embodiment of the disclosure, with the circuit diagram including a processing/communication module and five driver modules. Various magnified portions of FIG. 17 are shown in FIGS. 17A-17G.

Figure 17A:
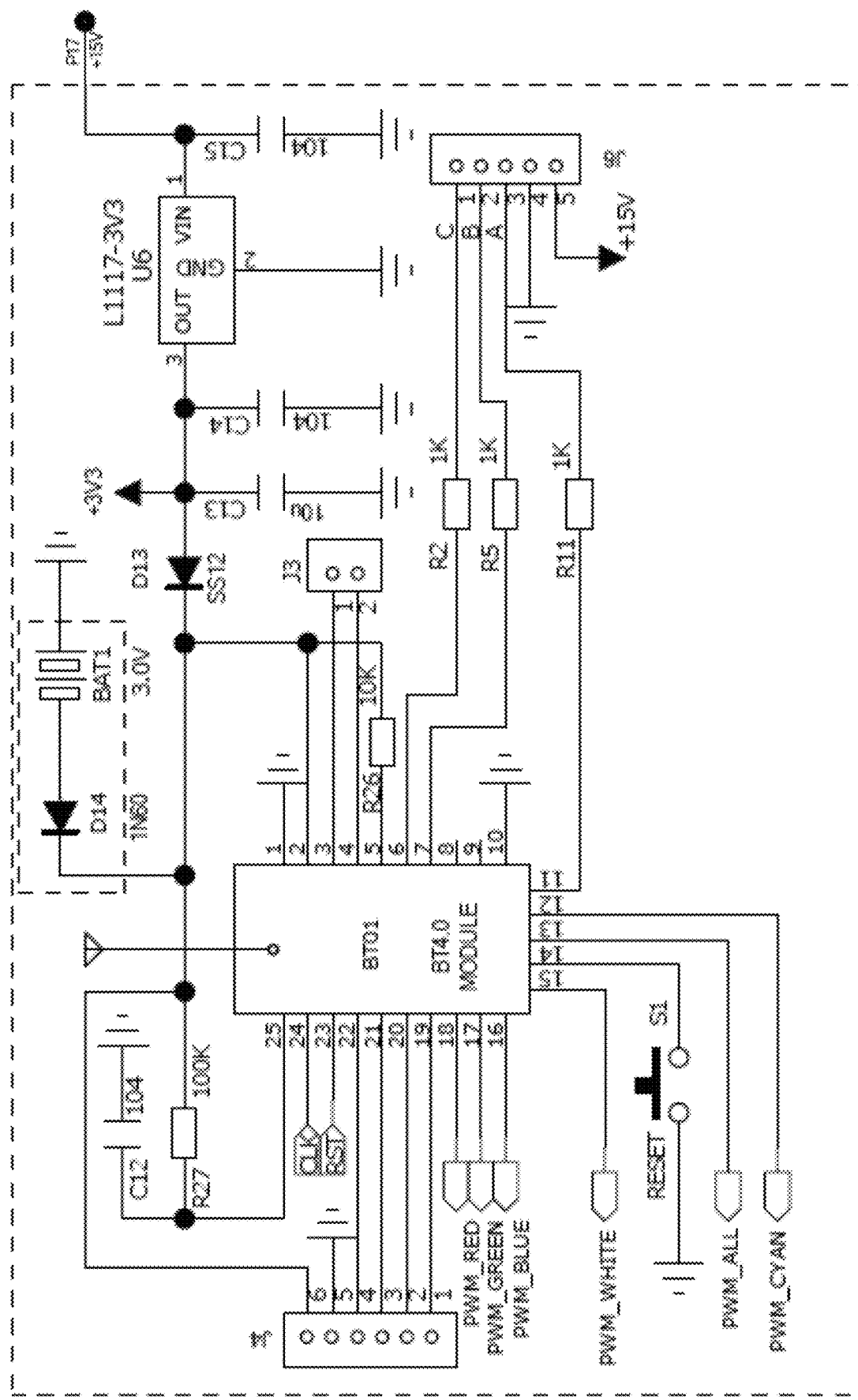
FIG. 17A is a magnified first portion of the circuit diagram of FIG. 17, including processing and communication module elements.
Figure 17C:
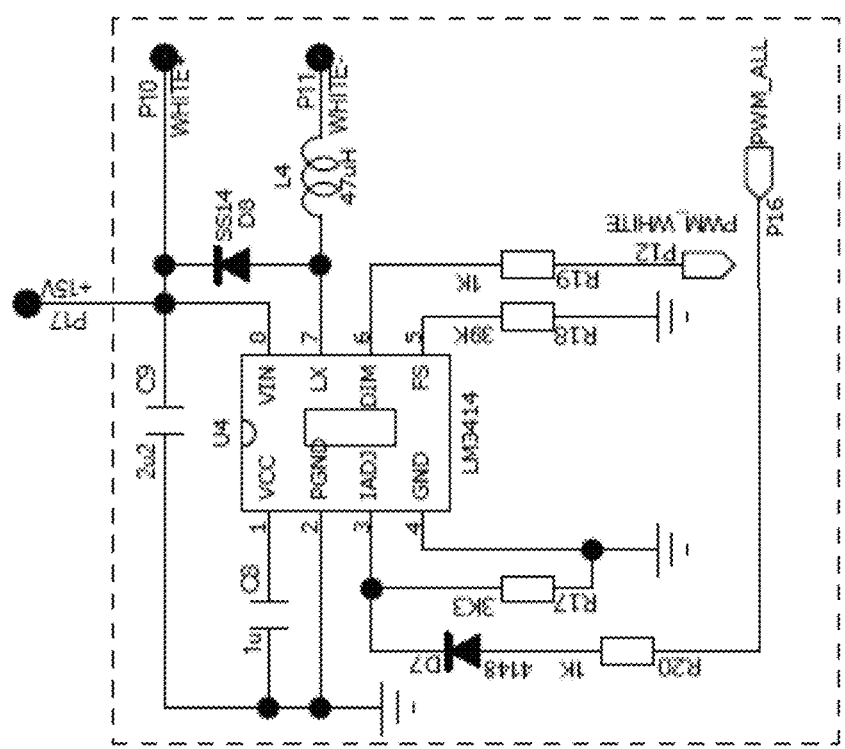
FIGS. 17B-17F include magnified second through sixth portions of the circuit diagram of FIG. 17, each including a driver module for driving a different group of LEDs.
Figure 17B:
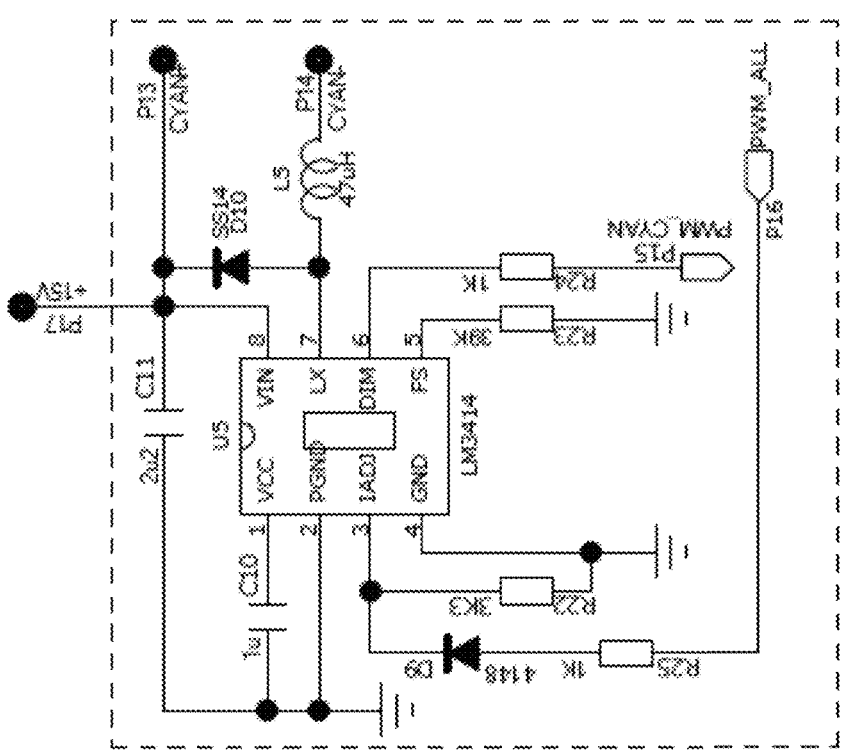
Figure 17E:
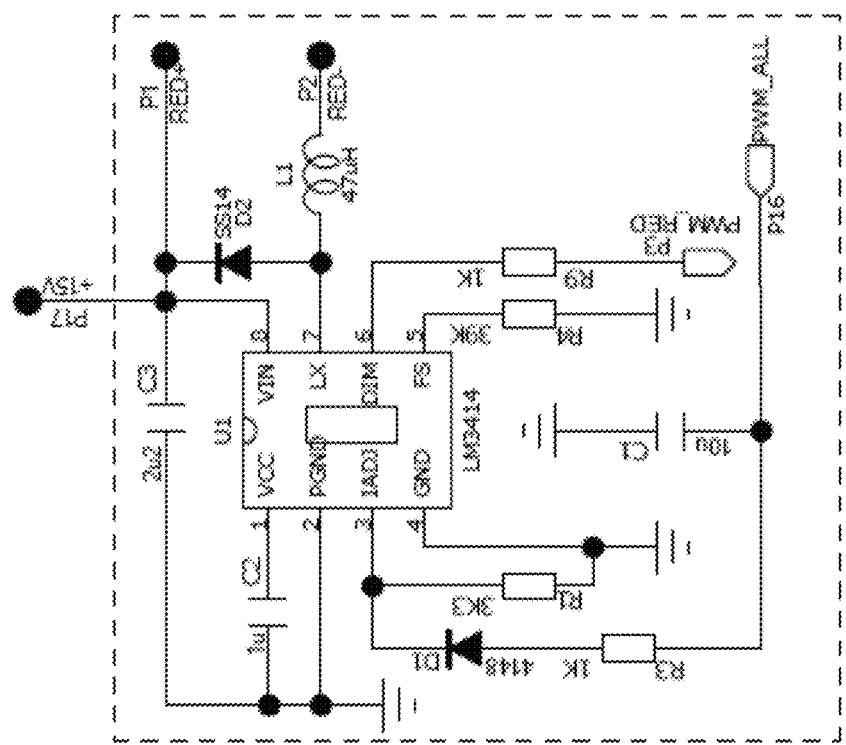
Figure 17D:
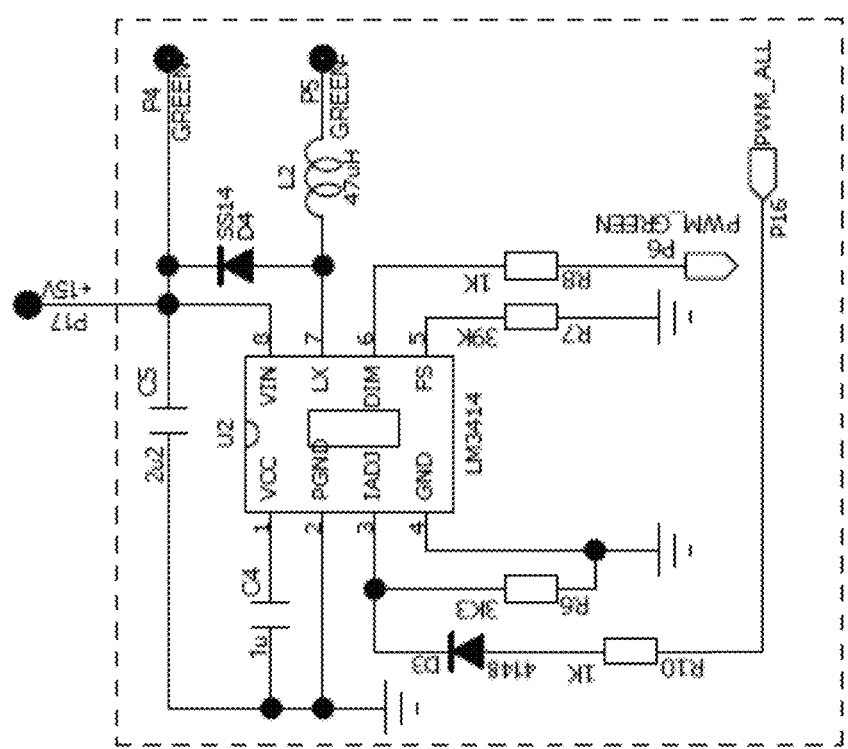

FIG. 17A is a magnified first portion of the circuit diagram of FIG. 17, including processing and communication module elements. As shown in FIG. 17A, a microcontroller BT01 having an integrated Bluetooth 4.0 module serves as a processor, and includes an integrated reprogrammable memory. The microcontroller BT01 is arranged to receive current from a voltage regulator U6 (at upper right). Terminal blocks J3, J4, J6 may be used for receiving serial communications from one or more sensors or detectors, and for serial communication with a programming or interrogation interface. The microcontroller BT01 provides pulse width modulated output signals to five driver modules via pins 12, 13, and 15-18.

Figure 17G:
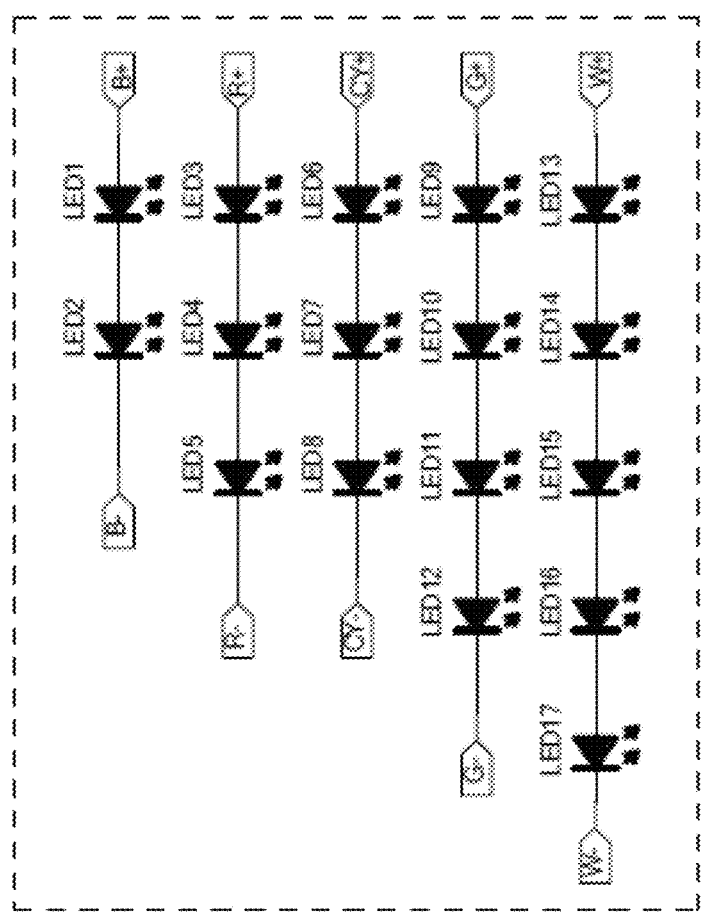
FIG. 17G is a magnified seventh portion of the circuit diagram of FIG. 17, including five different groups (strings) of LEDs.
Figure 17F:
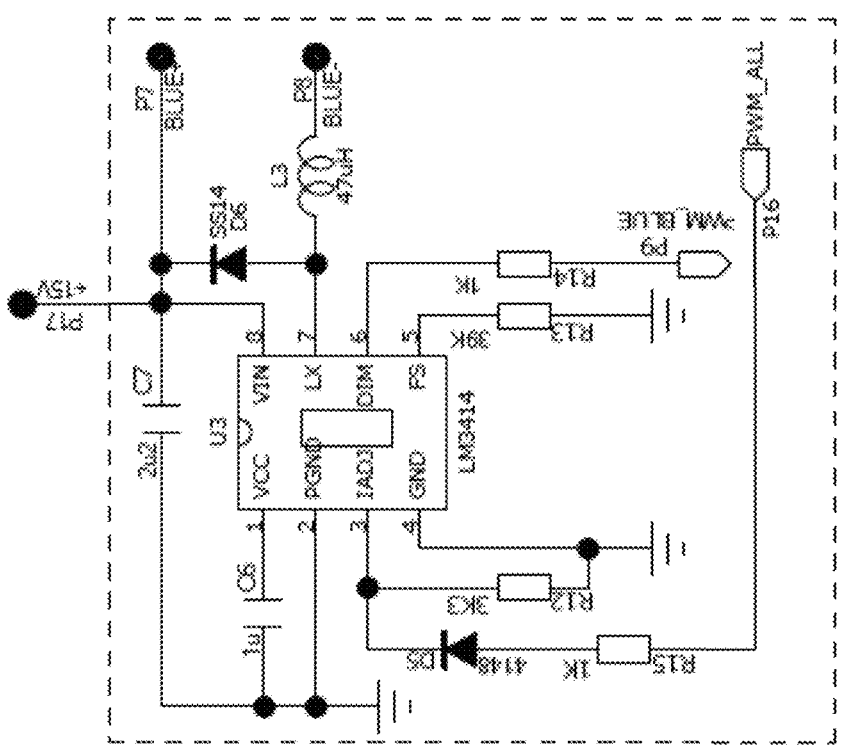

FIGS. 17B-17F include magnified second through sixth portions of the circuit diagram of FIG. 17, each including a driver module for driving a different group of LEDs shown in FIG. 17G. Each driver module receives 18 VDC and receives a pulse width modulated (PWM_signal from the microcontroller BT01 (shown in FIG. 17A) to permit control of the corresponding LED group, wherein FIG. 17G shows the five different groups (or strings) of LEDs—namely, short wavelength blue, red, cyan (or long wavelength blue), green, and white.

Figure 18A:
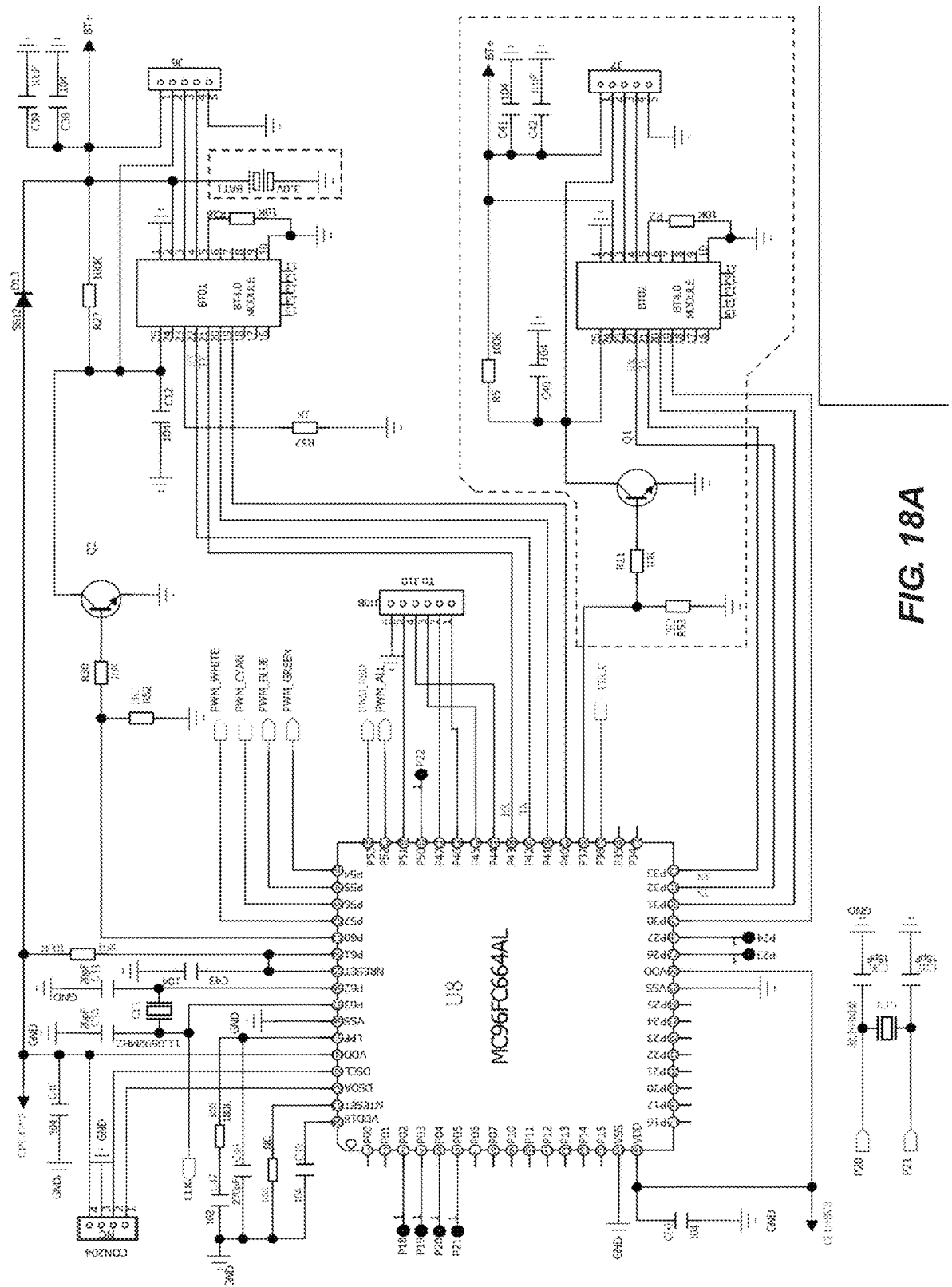
FIG. 18A is a first portion of a circuit diagram, including processing and communication elements, of a lighting device arranged to independently control five different groups of LEDs according to one embodiment of the disclosure.

FIG. 18A is a first portion of a circuit diagram, including processing and communication elements, of a lighting device arranged to independently control five different groups of LEDs according to one embodiment of the disclosure. A microcontroller U8 is in communication with a first Bluetooth wireless transceiver BT01 and a second Bluetooth wireless transceiver BT02. The microcontroller U8 is arranged to receive inputs from sensors (including a dimmer sensor arranged to communicate with microcontroller pin P34, and a passive infrared sensor arranged to communicate with microcontroller pin 36) via terminal block J3 (at lower center). The microcontroller U8 is further arranged to receive programming inputs via a programming jack J10B (at lower center). Each wireless transceiver BT01, BT02 shown in FIG. 18A includes a corresponding programming jack J6, J7.

Figure 18B:
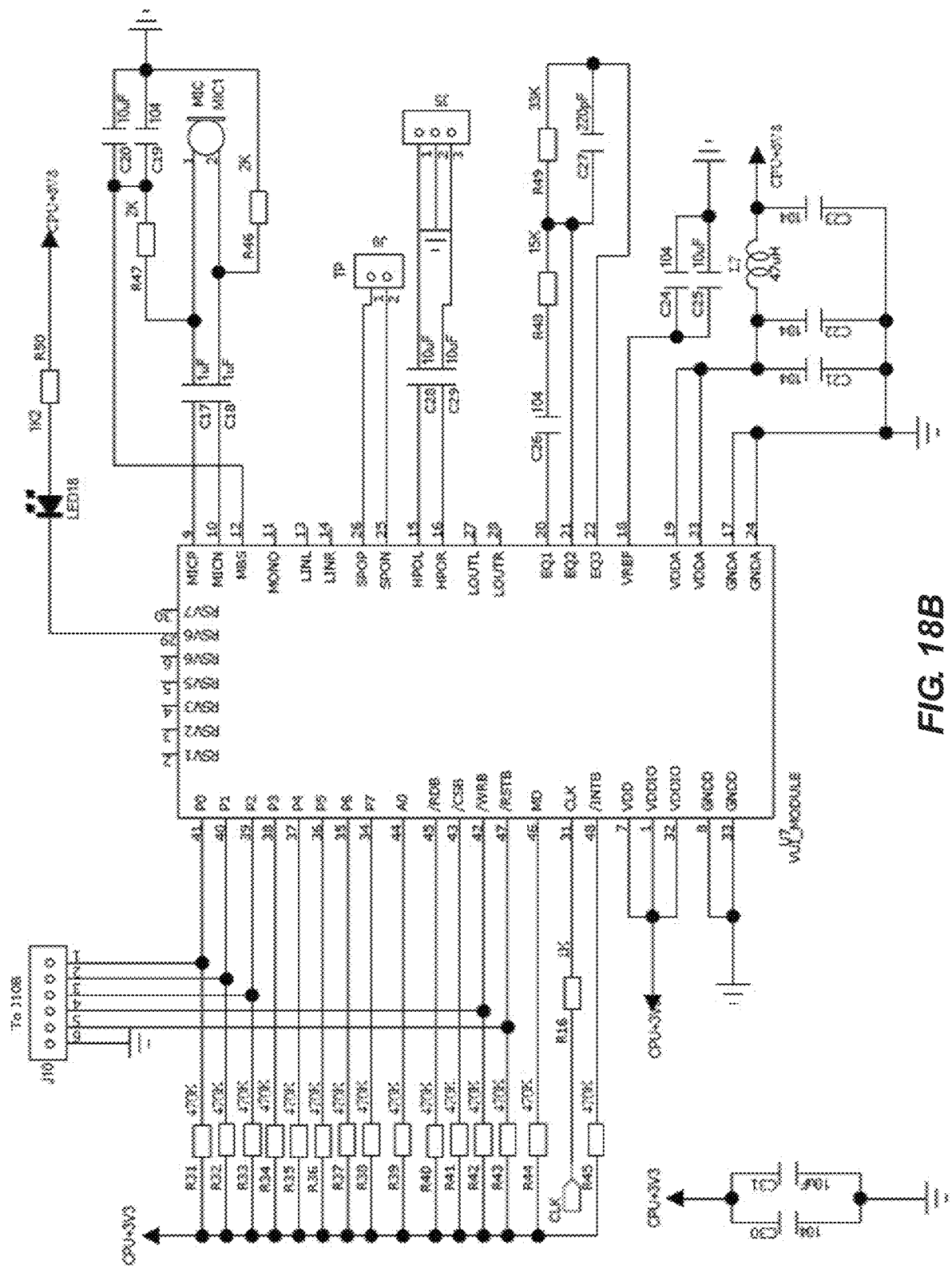
FIG. 18B is a second portion of a circuit diagram including voice recognition elements arranged to operate in conjunction with the circuit elements of FIG. 18A for control of the lighting device.
Figure 18C:
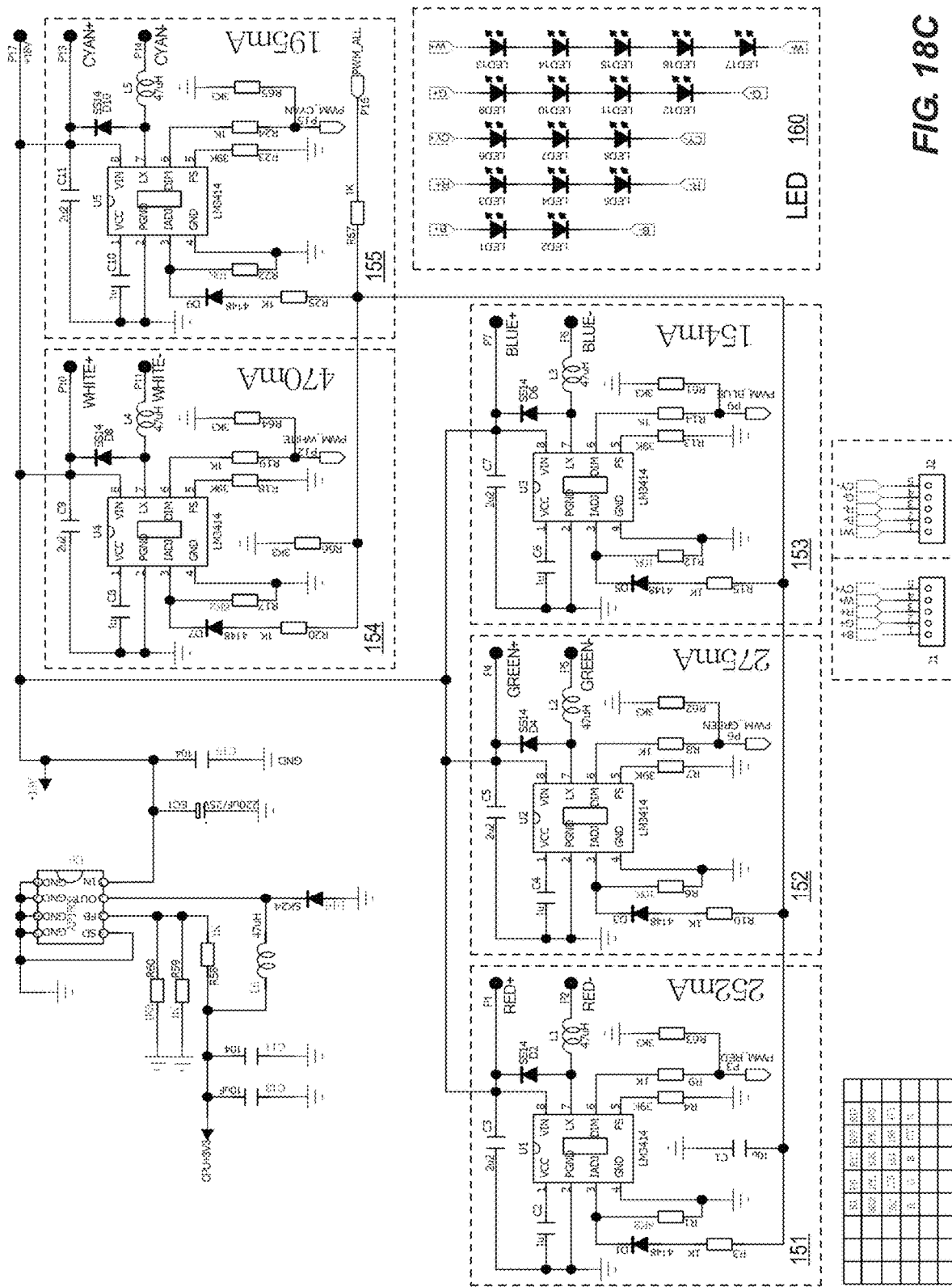
FIG. 18C is a third portion of a circuit diagram including multiple driver modules arranged to operate in conjunction with the circuit elements of FIGS. 18A-18B for control of the lighting device.

FIG. 18B is a second portion of a circuit diagram including voice recognition elements arranged to operate in conjunction with the circuit elements of FIG. 18A for control of the lighting device. FIG. 18B shows a voice recognition integrated circuit U7 (at center) arranged to receive an input signal from a microphone MIC 1 (at upper right). FIG. 18C is a third portion of a circuit diagram including multiple LED driver modules 151-155 arranged to operate in conjunction with the circuit elements of FIGS. 18A-18B for control of LEDs (forming a LED array 160) of the lighting device.

Figure 18D:
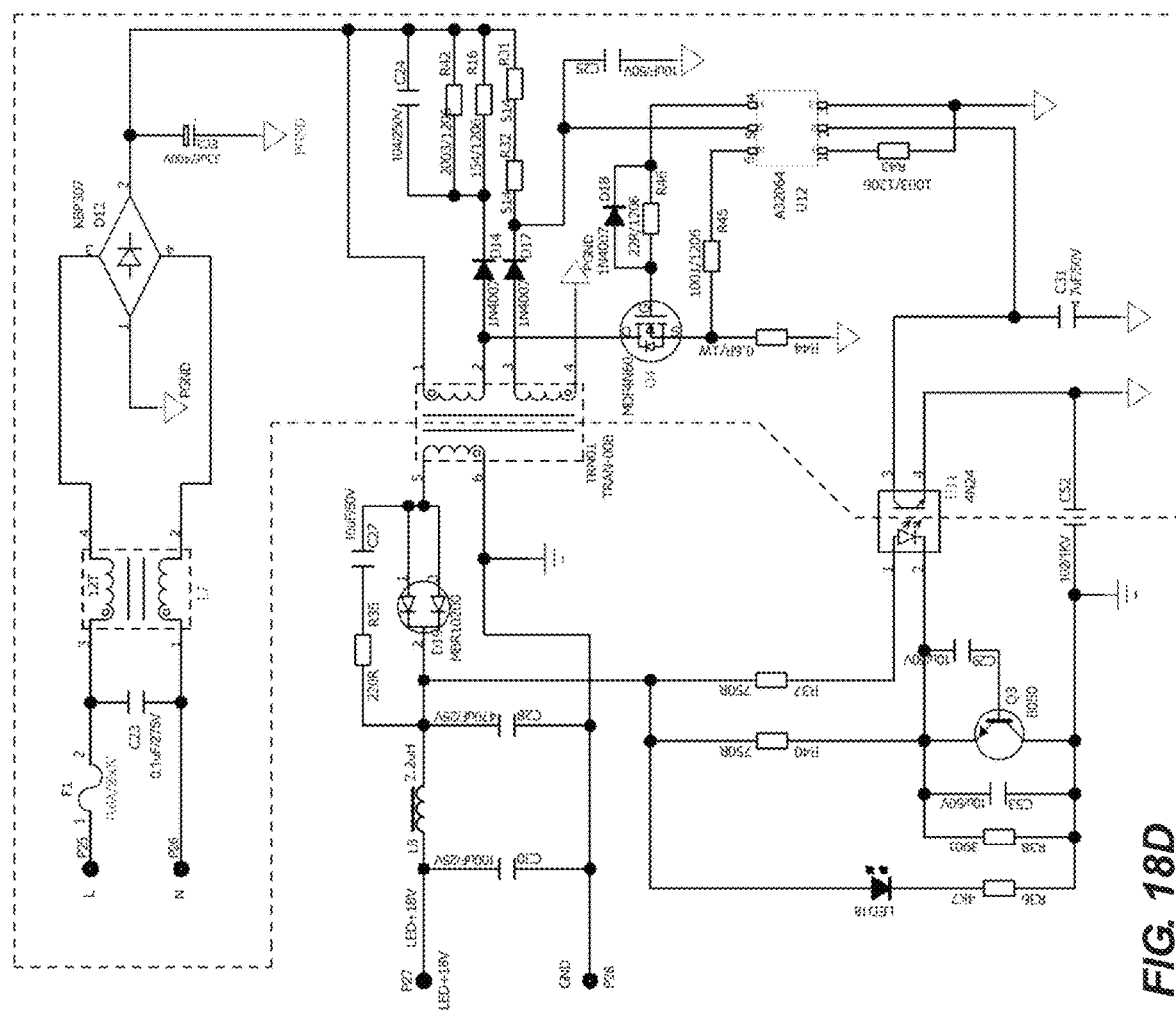
FIG. 18D is a fourth portion of a circuit diagram including AC-DC power conversion elements arranged to operate in conjunction with the circuit elements of FIGS. 18A-18C for control of the lighting device.

FIG. 18D is a fourth portion of a circuit diagram including AC-DC power conversion elements arranged to operate in conjunction with the circuit elements of FIGS. 18A-18C for control of the lighting device. A transformer TRN01 and other elements are configured to output an 18 VDC signal at terminals P27, P28 for use by groups of LEDs collectively forming the LED array 160 shown in FIG. 18C.

FIG. 19 is a table identifying emitter control step (within a range of from 0 to 255), aggregate lumens, color rendering index (CRI), color quality scale (CQS), relative gamut (Qg), gamut area index (GAI), luminous efficacy of radiation (LER), and CRI R9 for a lighting device according to one embodiment of the disclosure including five groups of LEDs (red, green, long wavelength blue, white (BSY), an short wavelength blue) operated at sixteen different CCT values according to an instruction set arranged to simultaneously achieve high CRI (at least 90) and high Qg (exceeding 100) for multiple CCT values spanning from 2300K to 9300K. Aggregate lumens in a range of from 650-700 lumens were obtained from 2700K to 9300K. Qg values of greater than 100 were also obtained for all CCT values in the range of from 1200K to 9300K. FIG. 19 shows that a lighting device including at least five groups of solid state light emitters as disclosed herein may produce aggregate emissions comprising one, two, three, or all four of the following characteristics (A) to (D): (A) a CRI value of at least 90 and a Qg value of at least 100 over a CCT range spanning at least from 2700K to 9000K; (B) a CRI R9 value of at least 80 over a CCT range spanning at least from 2700K to 9000K; (C) a luminous flux value of at least 600 over a CCT range spanning at least from 2700K to 9000K; and (D) a luminous efficacy of radiation value of at least 300 over a CCT range spanning at least from 2700K to 5700K.

Prototype

Figure 20A:
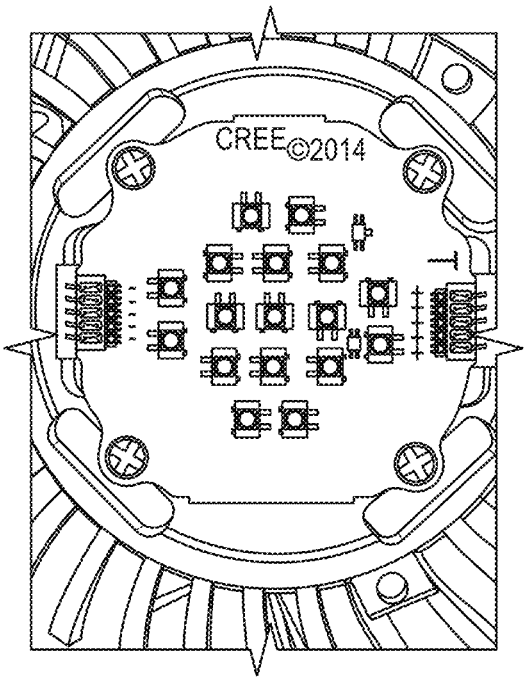
FIG. 20A illustrates a LED module including five groups of LEDs arranged in a two-dimensional array and mounted to a substrate coated with a light-reflective material, with the LED module being mounted along an outwardly-facing surface of a body portion of a lighting device embodied in a cylindrical downlight intended for in-ceiling mounting.

FIG. 20A illustrates a LED module including five groups of LEDs arranged in a two-dimensional array and mounted to a substrate coated with a light-reflective material, with the LED module being mounted along an outwardly-facing surface of a body portion of a lighting device embodied in a cylindrical downlight intended for in-ceiling mounting. The LED module is substantially similar to the layout shown in FIG. 4B, including groups of LEDs separately arranged to emit short wavelength blue, red, long wavelength blue (or cyan), green, and white (or blue-shifted yellow) light.

Figure 20B:
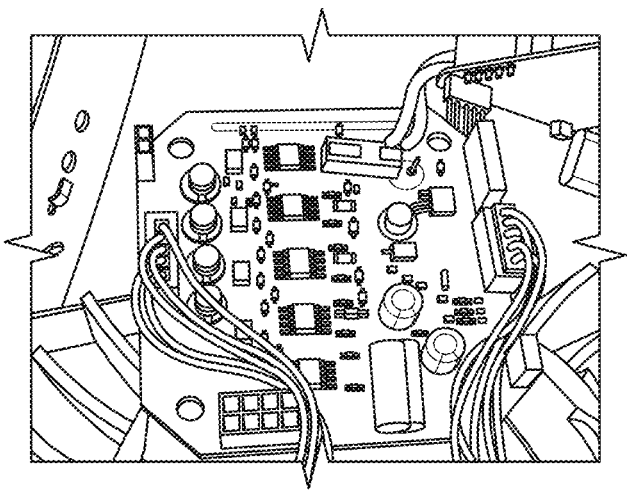
FIG. 20B illustrates a first circuit board including driver modules arranged for use with the LED module of the lighting device of FIG. 20A, with the first circuit board arranged to be mounted along an inwardly facing surface of a body portion of the lighting device.

FIG. 20B illustrates a first circuit board including driver modules arranged for use with the LED module of the lighting device of FIG. 20A, with the first circuit board arranged to be mounted along an inwardly facing surface of a body portion of the lighting device.

Figure 20D:
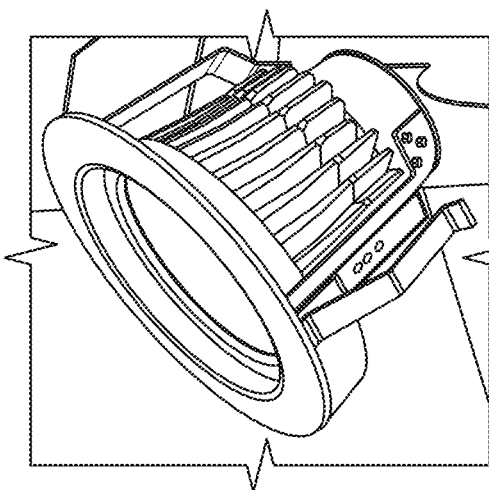
FIG. 20D illustrates a lighting device including the LED module, body portion, first circuit board, and second circuit board depicted in FIGS. 20A-20C, with the lighting device being in a state of operation and emitting light.
Figure 20C:
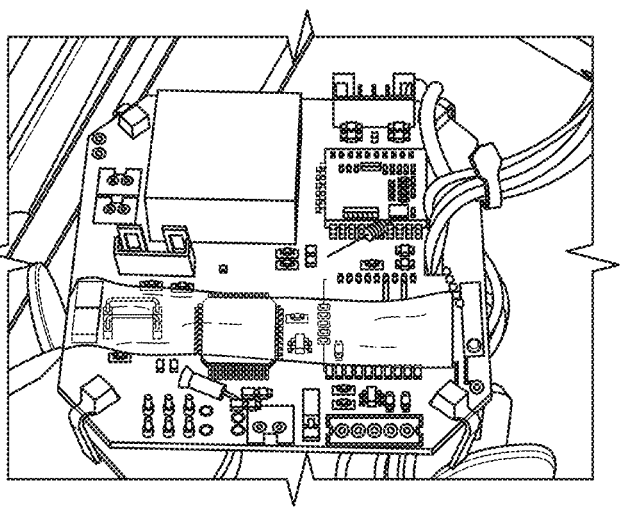
FIG. 20C illustrates a second circuit board including control elements arranged for use with the first circuit board and the LED module of FIGS. 20A-20B, with the second circuit board overlying the first circuit board.

FIG. 20C illustrates a second circuit board including control elements arranged for use with the first circuit board and the LED module of FIGS. 20A-20B, with the second circuit board overlying the first circuit board.

FIG. 20D illustrates a lighting device including the LED module, body portion, first circuit board, and second circuit board depicted in FIGS. 20A-20C, with the lighting device being in a state of operation and emitting light.

Figure 21B:
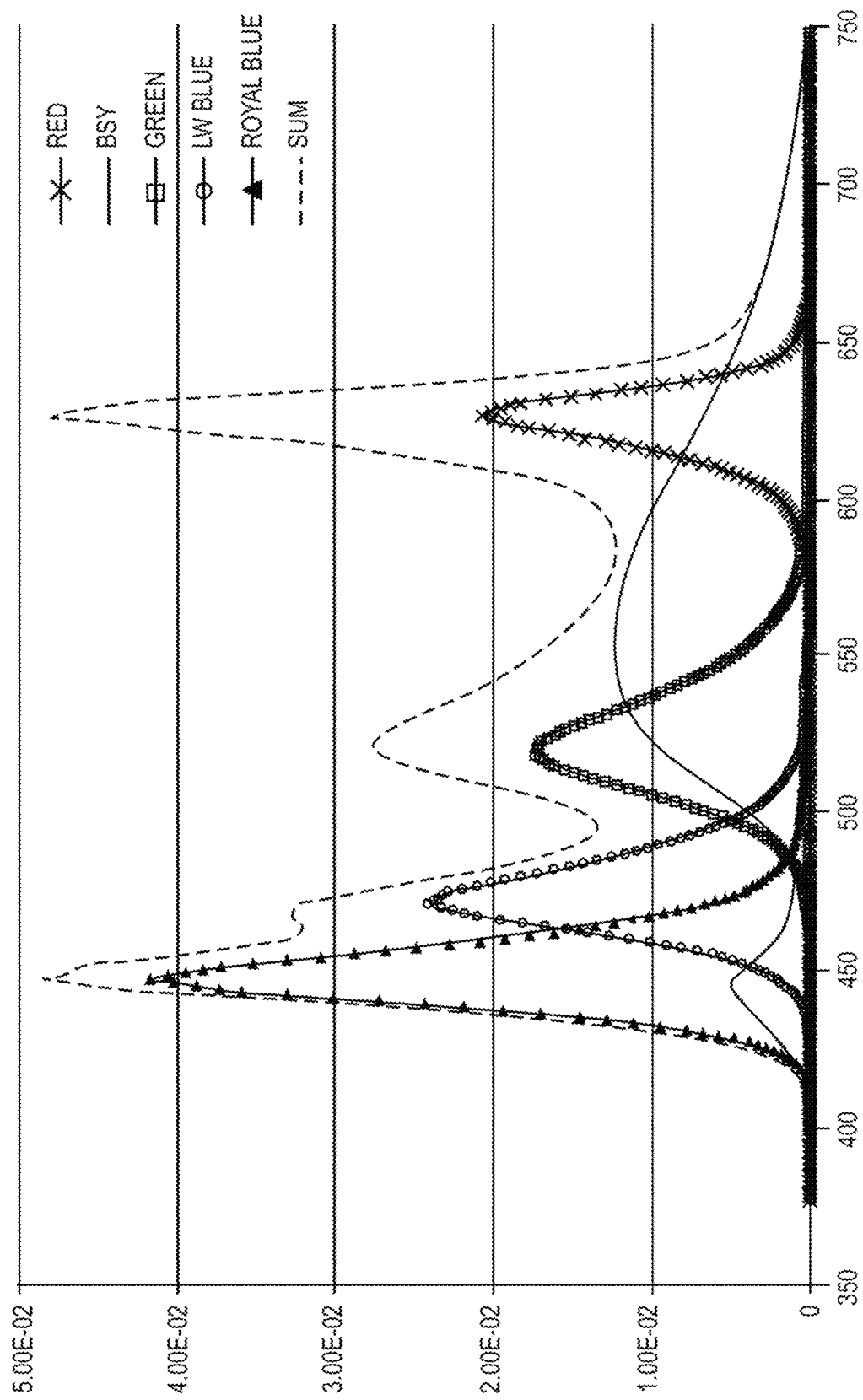
FIG. 21B is an overlay plot of spectral power distribution (intensity versus wavelength) for the five groups of LEDs of the lighting device of FIG. 21A when operated at maximum current, with a plot of spectral power distribution diagram for aggregate emissions of the lighting device.

FIG. 21A is a table providing control step (in a range of from 0-255), x color coordinate, y color coordinate, dominant wavelength, peak wavelength, center wavelength, CCT, full width-half maximum, radiant flux (Watts) per control step, lumens per control step, radiant flux (Watts), percent radiant flux, lumens, percent lumens, and luminous efficacy of radiation for a five groups of LEDs (red, blue-shifted yellow, green, long wavelength blue or cyan, and short wavelength blue) of a lighting device with each group operated at maximum current. Aggregate emissions have a CCT of 7516K near the blackbody locus, as indicated by the duv value of −0.0135. FIG. 21B is an overlay plot of spectral power distribution (intensity versus wavelength) for the five groups of LEDs of the lighting device of FIG. 21A when operated at maximum current, with a plot of spectral power distribution for aggregate emissions of the lighting device.

Figure 21C:
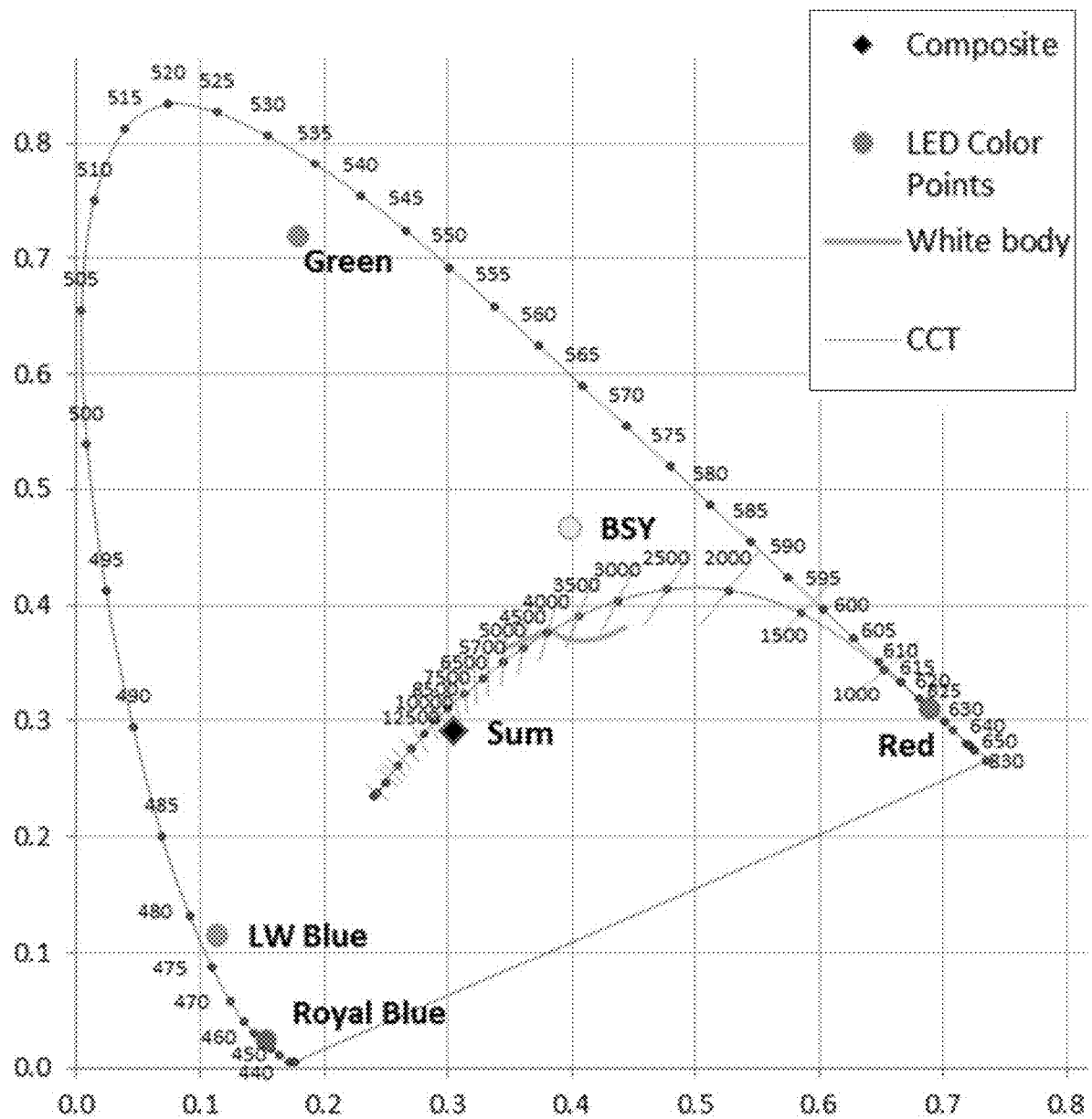
FIG. 21C is a CIE 1931 chromaticity diagram showing the blackbody locus, overlaid with a line of minimum tint (or "white body line"), with first through fifth color points corresponding to outputs of the five groups of LEDs of the lighting device of FIGS. 21A-21B, and with a composite color point for aggregate emissions of the five groups of LEDs.

FIG. 21C is a CIE 1931 chromaticity diagram showing the blackbody locus, overlaid with a line of minimum tint (or "white body line"), with first through fifth color points corresponding to outputs of the five groups of LEDs of the lighting device of FIGS. 21A-21B, and with a composite color point for aggregate emissions of the five groups of LEDs. As shown in FIG. 21C, the first through fifth color points are widely separated, thereby permitting a very large number (e.g., millions) of aggregate color points to be obtained. The aggregate color point is proximate to the BBL with a CCT of 7516K.

Figure 22:
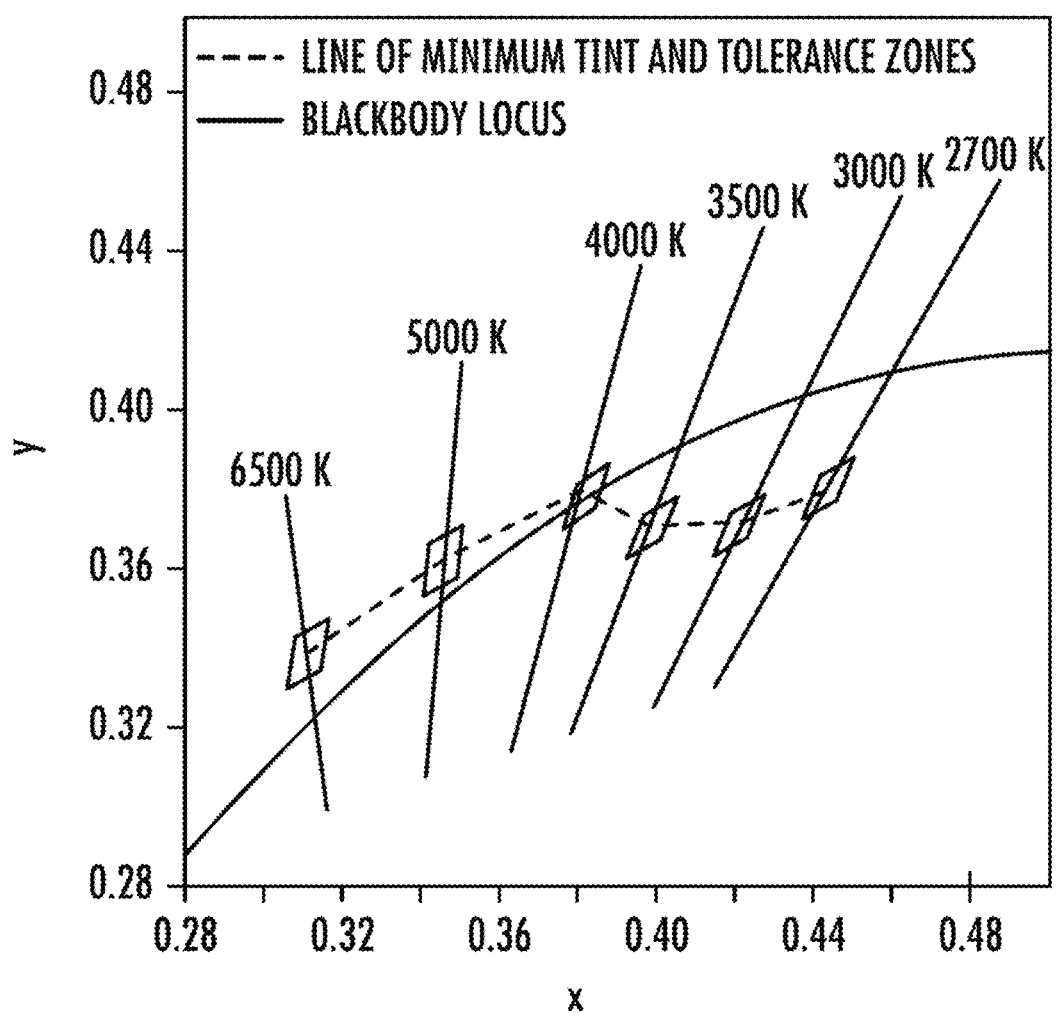
FIG. 22 is an excerpt of a CIE 1931 chromaticity diagram showing the blackbody locus and including a line of minimum tint (or "white body line") extending between CCT values of from 2700K to 6500K.
Figure 23B:
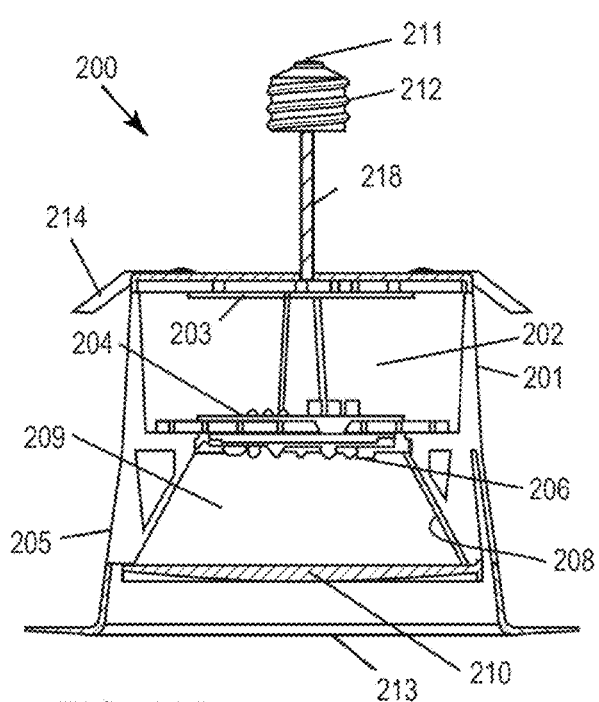
FIG. 23B is a cross-sectional view of the lighting device of FIG. 23A.
Figure 23A:
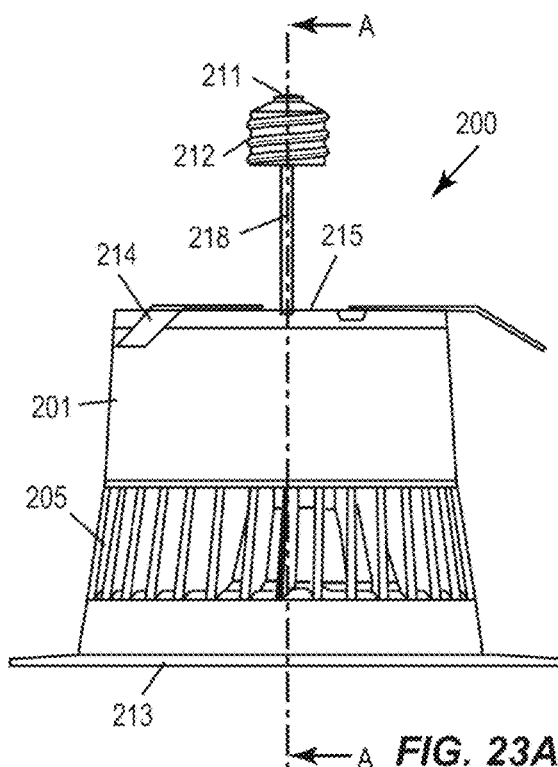
FIG. 23A is a side elevation view of a lighting device according to one embodiment of the disclosure embodied in a substantially cylindrical downlight intended for in-ceiling mounting and including multiple (e.g., five or more) separately controllable groups of LEDs.
Figure 23C:
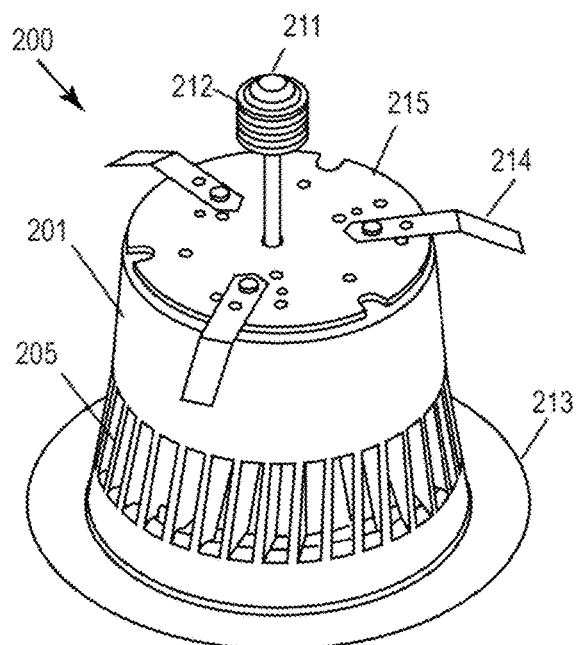
FIG. 23C is an upper perspective view of the lighting device of FIGS. 23A-23B.
Figure 23D:
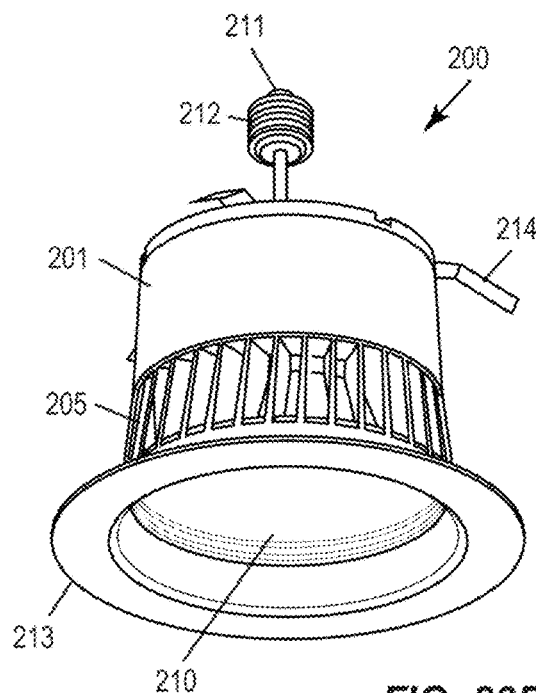
FIG. 23D is a lower perspective view of the lighting device of FIGS. 23A-23C.
Figure 25A:
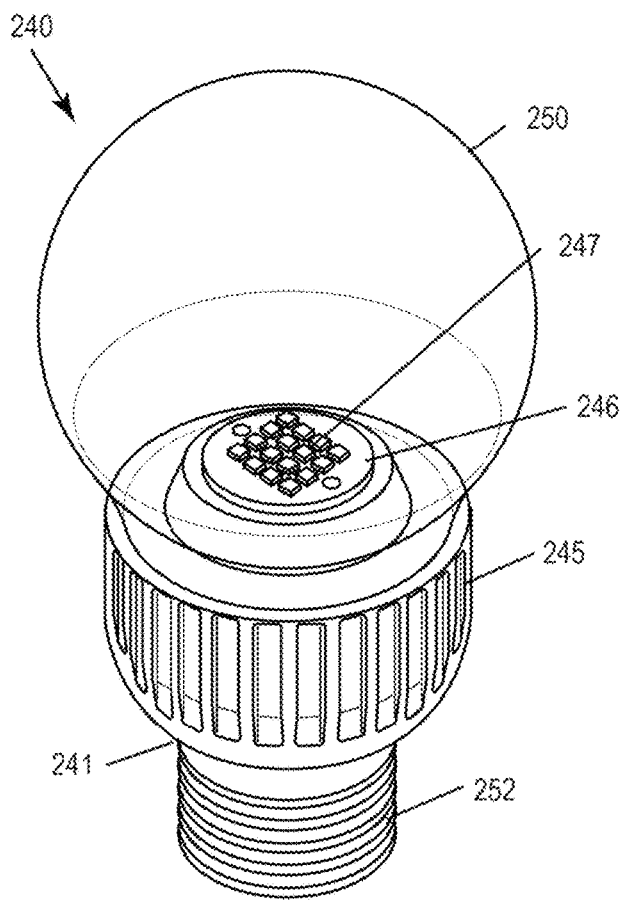
FIG. 25A is an upper perspective view of a light bulb including multiple (e.g., five or more) separately controllable groups of LEDs arranged in a two-dimensional array according to one embodiment of the disclosure.
Figure 25B:
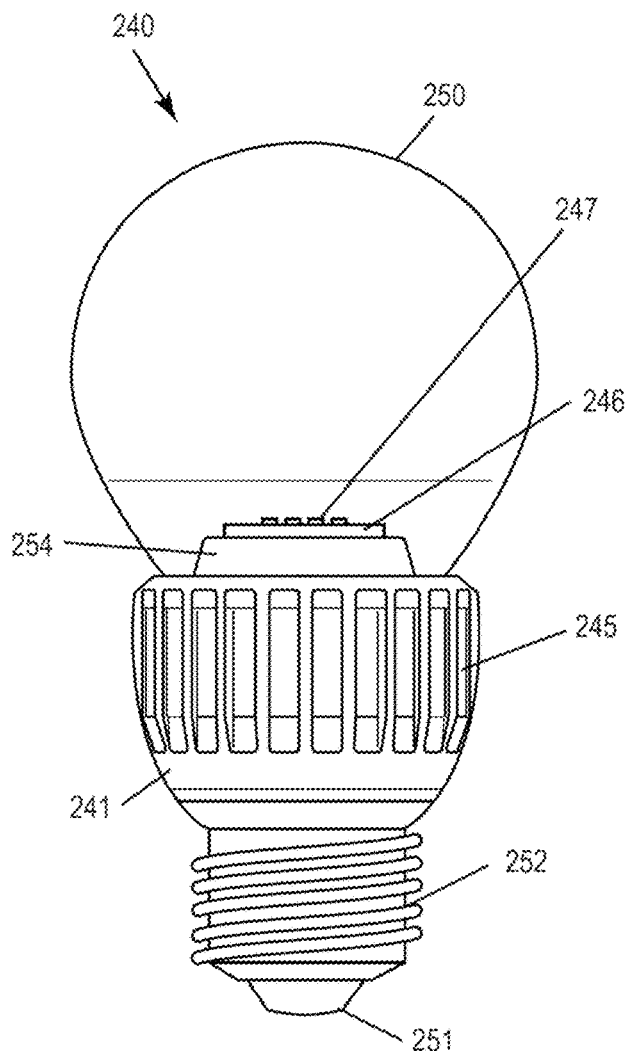
FIG. 25B is a side elevation view of the light bulb of FIG. 25A.
Figure 25C:
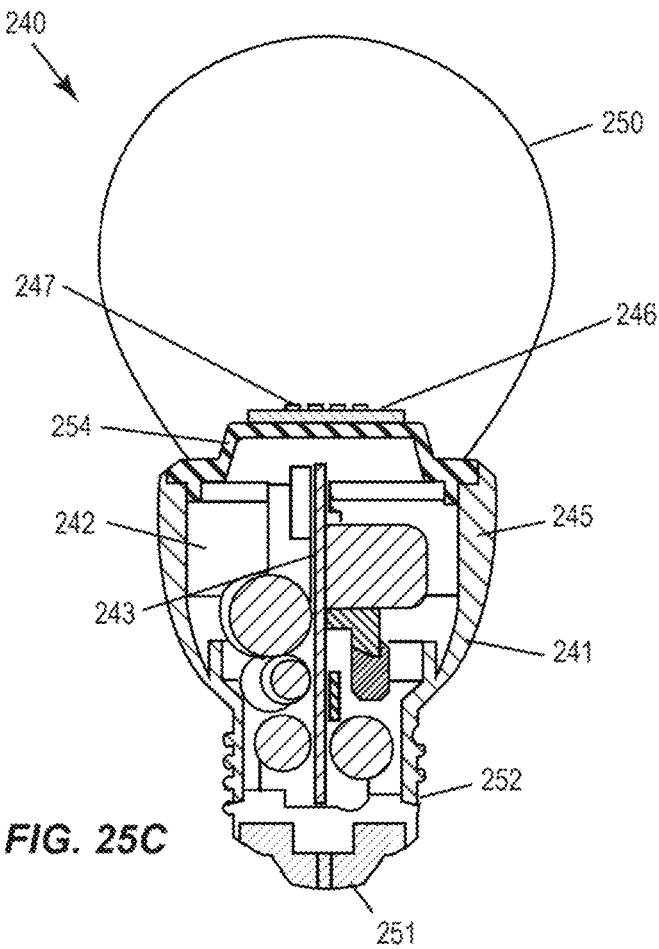
FIG. 25C is a first side cross-sectional view of the light bulb of FIGS. 25A-25B.
Figure 25D:
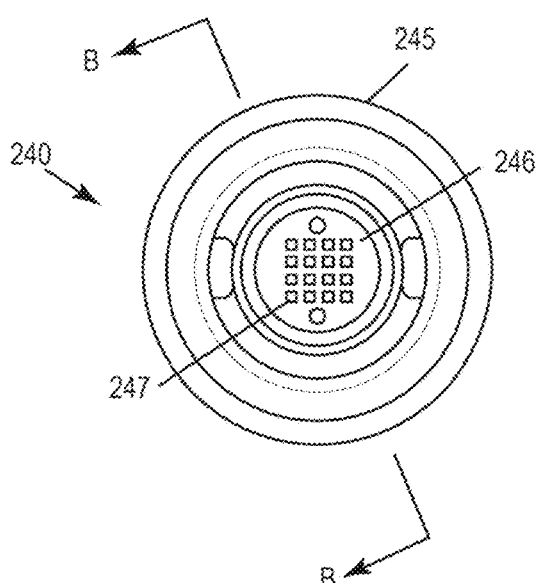
FIG. 25D is a top plan view of the light bulb of FIGS. 25A-25C.
Figure 25E:
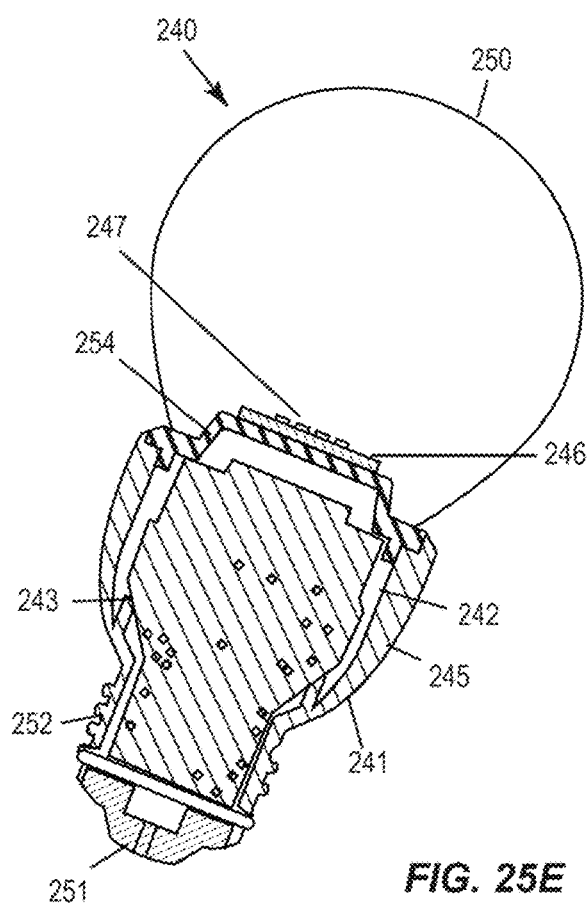
FIG. 25E is a second cross-sectional view of the light bulb of FIGS. 25A-25D.
Figure 26A:
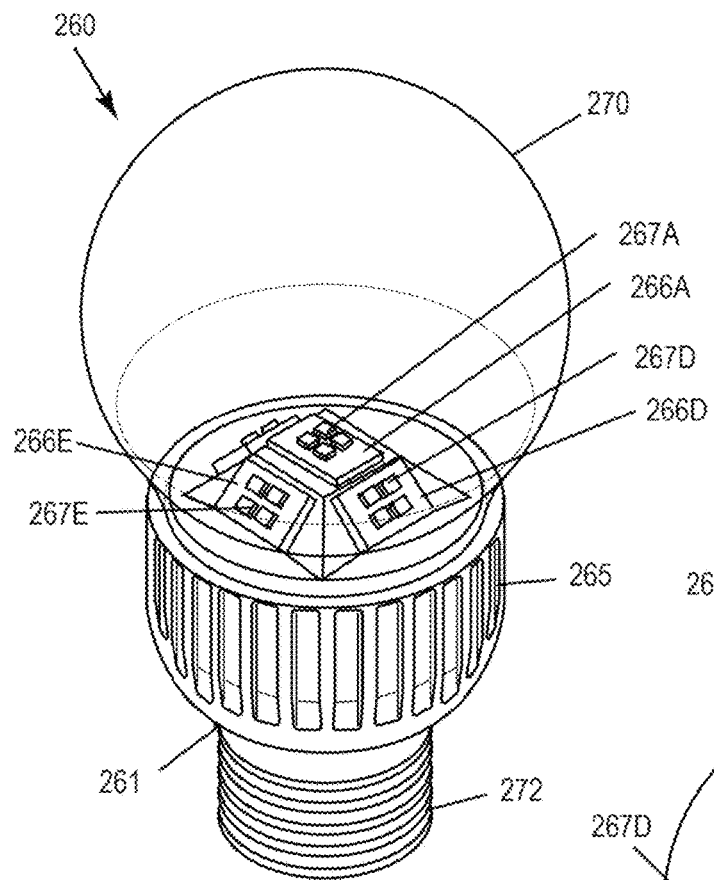
FIG. 26A is an upper perspective view of a light bulb including multiple (e.g., five or more) separately controllable groups of LEDs arranged on five non-coplanar emitter support surfaces according to one embodiment of the disclosure.
Figure 26B:
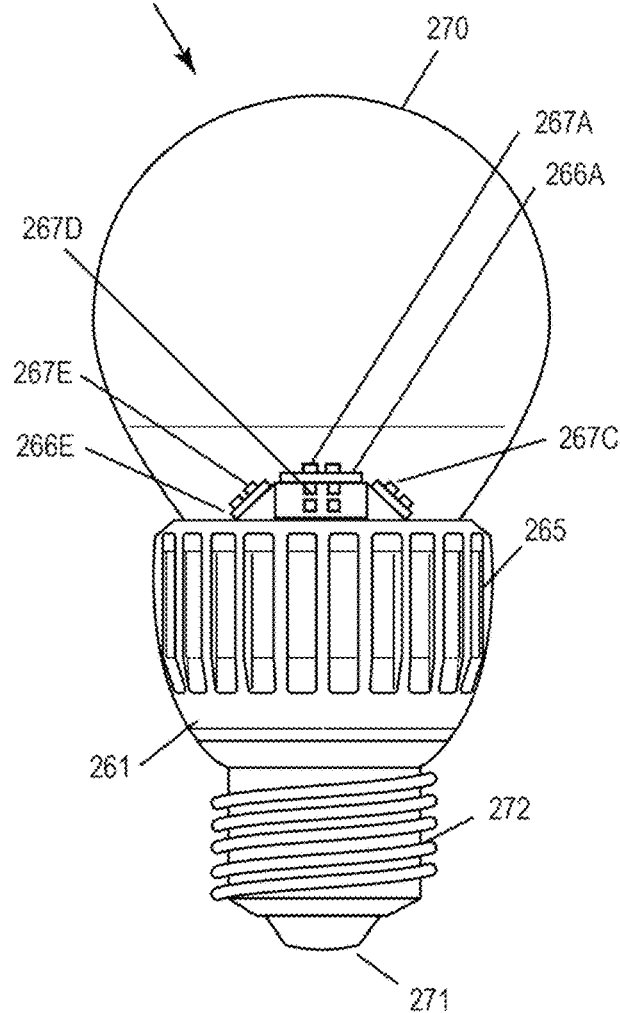
FIG. 26B is a side elevation view of the light bulb of FIG. 26A.
Figure 26C:
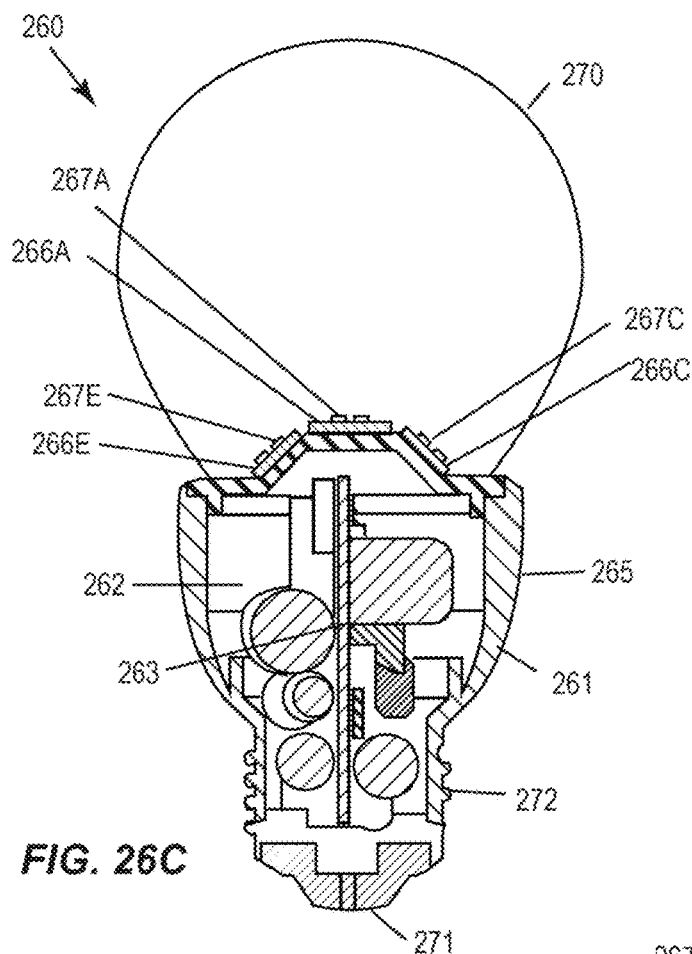
FIG. 26C is a first side cross-sectional view of the light bulb of FIGS. 26A-26B.
Figure 26D:
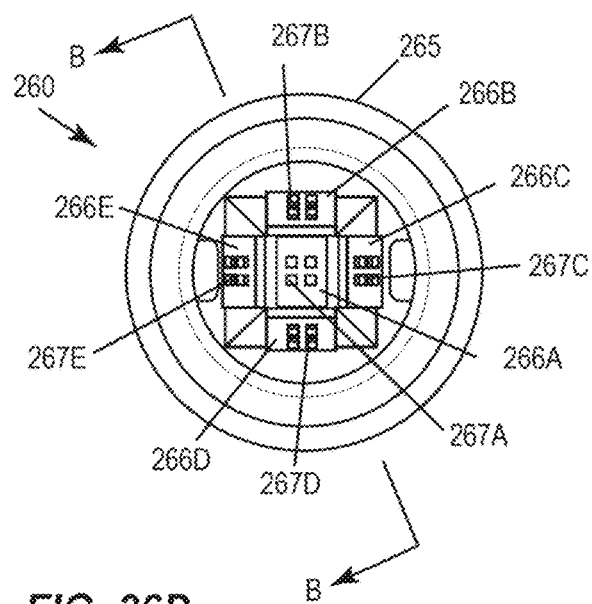
FIG. 26D is a top plan view of the light bulb of FIGS. 26A-26C.
Figure 26E:
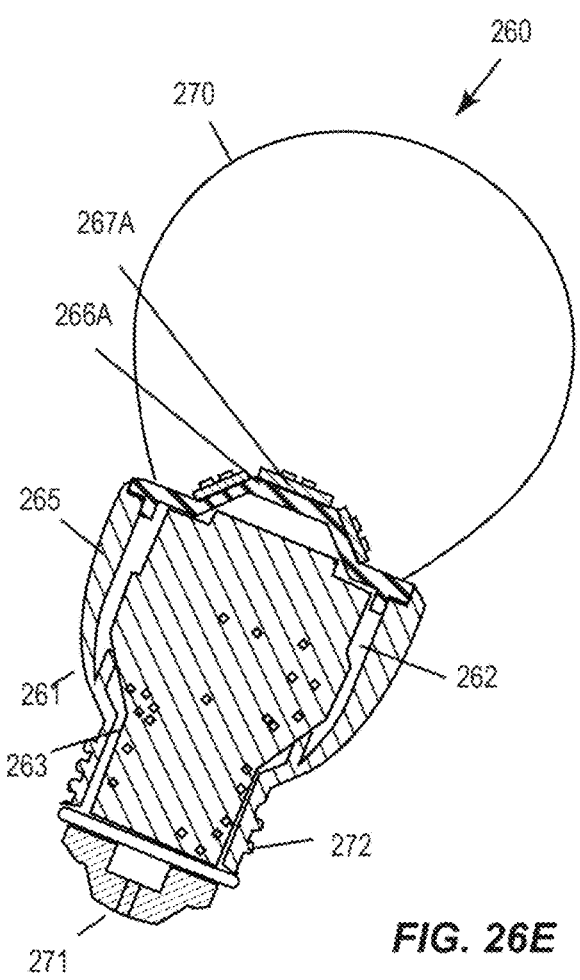
FIG. 26E is a second side cross-sectional view of the light bulb of FIGS. 26A-26D.
Figure 27A:
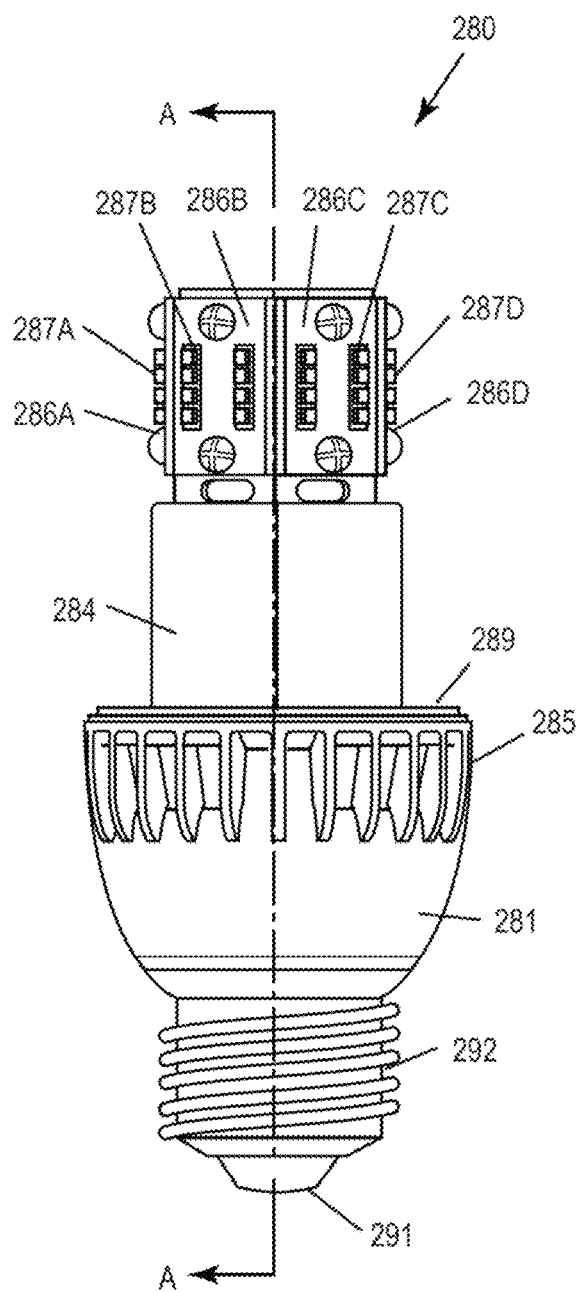
FIG. 27A is a first side elevation view of a light bulb including multiple (e.g., five or more) separately controllable groups of LEDs arranged on six non-coplanar support surfaces each arranged generally parallel to a longitudinal axis of the light bulb according to one embodiment.
Figure 27B:
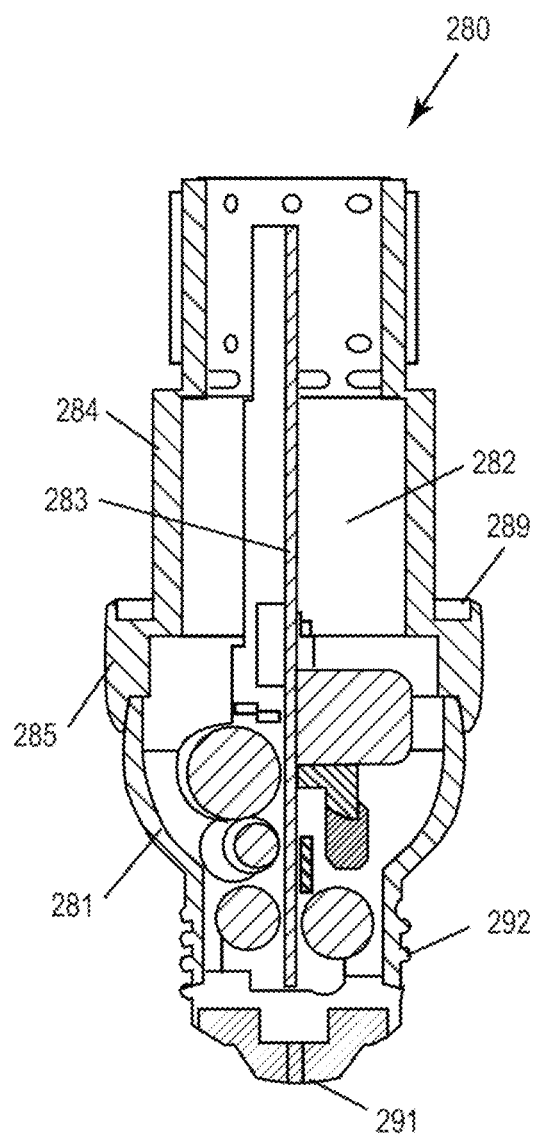
FIG. 27B is a first side cross-sectional view of the light bulb of FIG. 27A.
Figure 27C:
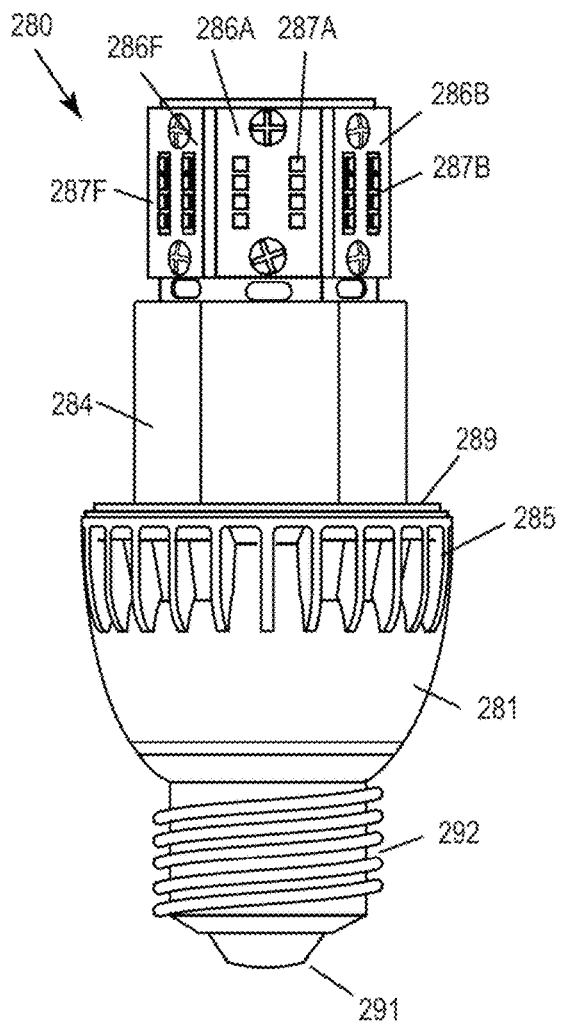
FIG. 27C is a second side elevation view of the light bulb of FIGS. 27A and 27B.
Figure 27D:
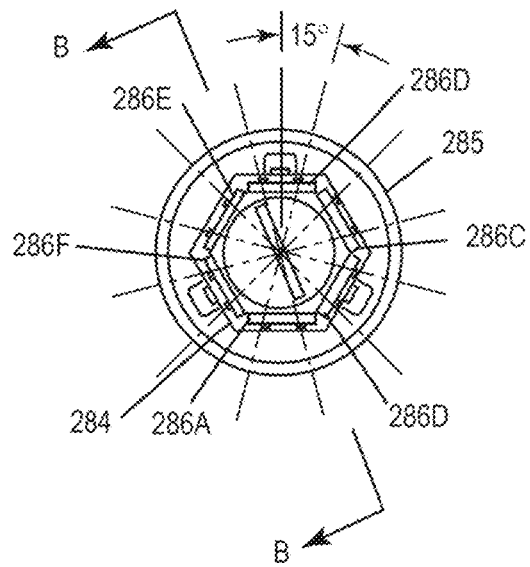
FIG. 27D is a top plan view of the light bulb of FIGS. 27A-27C.
Figure 27E:
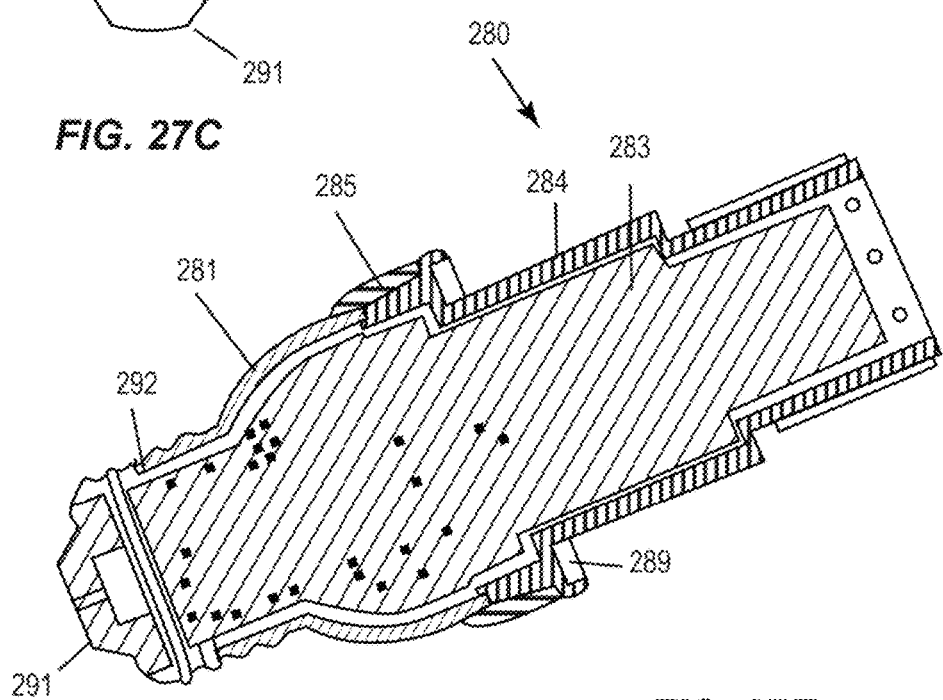
FIG. 27E is a second side cross-sectional view of the light bulb of FIGS. 27A-27D.

FIG. 22 is an excerpt of a CIE 1931 chromaticity diagram showing the blackbody locus and including a line of minimum tint (or "white body line") extending between CCT values of from 2700K to 6500K. Researchers have determined that a majority of people prefer sources of illumination on "white body line" (WBL) more than those of the same CCT line of blackbody radiation. (See, e.g., Rea, M. S. and Freyssinier, J. P.: White lighting for residential applications, Light Res. Tech., 45(3), pp. 331-344 (2013).) As shown in FIG. 2, at CCT values below about 4000K, the WBL is below the blackbody curve, whereas at higher CCT values, the WBL is above the blackbody curve. In certain embodiments, a lighting device as disclosed herein is configured to adjust aggregated light emissions of the solid state lighting device to move between at least two color points, wherein at least a first color point of the at least two color points embodies a combination of light exiting the lighting device that was emitted by the first electrically activated solid state light emitter and the second electrically activated solid state light emitter that produces, in the absence of any additional light, aggregated light emissions having (x, y) coordinates on a 1931 CIE Chromaticity Diagram that define a point on or within 7 MacAdam ellipses of a white body locus embodying a line including segments defined by the following x, y coordinates on a 1931 CIE Chromaticity Diagram: (0.3114, 0.3386) to (0.3462, 0.3631), (0.3462, 0.3631) to (0.3777, 0.3790), (0.3777, 0.3790) to (0.3977, 0.3707), (0.3977, 0.3707) to (0.4211, 0.3713), and (0.4211, 0.3713) to (0.4437, 0.3808). In this manner, color point may be adjusted (preferably on an automatic basis) along the WBL. Preferably, aggregated light emissions at the first and the second color point additionally have a luminous efficacy of at least 60 lumens per watt.

Lighting Device Configurations with Control Elements and Multiple Emitter Groups Various types of lighting devices and systems are contemplated according to embodiments of the disclosure. Certain embodiments may be directed to lighting fixtures (including in-ceiling, recessed, pendant, track light, and surface mount varieties), light bulbs, street lamps, indoor lamps, outdoor lamps, desk lamps, floor-standing lamps, and so on.

In certain embodiments, multiple groups of solid state light emitters are arranged to produce aggregate emissions of a lighting device. In certain embodiments, a solid state lighting device includes at least one or multiple of the following features: a single reflector arranged to reflect at least a portion of emissions generated by each group of the plurality of groups of solid state light emitters; a single lens arranged to transmit at least a portion of emissions generated by each group of the plurality of groups of solid state light emitters; a single diffuser arranged to diffuse at least a portion of emissions generated by each group of the plurality of groups of solid state light emitters; a single leadframe arranged to conduct electrical power to each group of the plurality of groups of solid state light emitters; a single circuit board or mounting element supporting each group of the plurality of groups of solid state light emitters; a single heatsink arranged to dissipate heat generated by each group of the plurality of groups of solid state light emitters; and a single optical cavity containing each group of the plurality of groups of solid state light emitters.

FIGS. 23A-23D illustrate a lighting device according to one embodiment of the disclosure, embodied in a substantially cylindrical downlight 200 intended for in-ceiling mounting and including multiple (e.g., five or more) separately controllable groups of LEDs as part of a LED module 206 (such as the module shown in FIG. 20A). The downlight 200 includes a generally cylindrical base housing 201 and a heatsink housing 205 that in combination form a body structure. Mounting elements 214 such as rotatable spring tabs are arranged along an upper surface 215 of the housing 201. A cable 218 extends between the base housing 201 and an Edison (screw-type) male connector forming a threaded lateral contact 212 and a foot contact 211. The base housing 201 defines an interior volume 202 containing printed circuit boards 203, 204 that include operative elements such a power converter, a controller module (e.g., including at least one processor and a memory), one or more transceivers (e.g., wireless transceivers), LED driver modules, sensor modules, detectors, voice recognition circuitry, and the like. The heatsink housing 205 defines an inner cavity 209 that includes a reflective surface 201 and is further bounded by a light transmissive optical element 201 such as a lens and/or a diffuser. A trim bezel 213 is arranged proximate to an open end of the heatsink housing. The downlight 200 may include any suitable features disclosed herein, and is preferably arranged to execute any one or more functions and/or method steps described herein.

FIGS. 24A-24C illustrate a lighting device according to one embodiment of the disclosure embodied in a substantially cylindrical track light fixture 220 intended to be supported by a wall- or ceiling-mounted track (not shown) and including multiple (e.g., five or more) separately controllable groups of LEDs, which may be arranged in a LED module 226. The fixture track light fixture 220 includes a body structure 221, a light emitting end 223, a base end 235, a mounting bracket 236, wires 238, a track connector 237, and electrical terminals 231. A base housing portion 222 preferably contains one or more circuit boards including operative elements such a power converter, a controller module (e.g., including at least one processor and a memory), one or more transceivers, LED driver modules, sensor modules, detectors, voice recognition circuitry, and the like. The body structure 221 may include a heatsink portion 225 and contain a cavity 229 bounded by a reflective surface 228 that may be faceted. A light mixing chamber 224 may be arranged between a LED module 226 and a light transmissive optical element 230 (e.g., diffuser and/or lens) arranged between the mixing chamber 224 and the cavity 229. The track light 220 may include any suitable features disclosed herein, and is preferably arranged to execute any one or more functions and/or method steps described herein.

FIGS. 25A-25E illustrate a light bulb 240 including multiple (e.g., five or more) separately controllable groups of LEDs 247 arranged in a two-dimensional array within a cavity bounded by a light transmissive globe or lens 250 according to one embodiment of the disclosure. The LEDs 247 are arranged on a single substantially planar emitter support surface 246, which may be elevated by a pedestal 254. The light bulb 240 includes a body structure 241 having an associated external heatsink 245. An Edison (screw-type) connector including a threaded lateral contact 252 and a foot contact 251 extend from one end of the body structure 241 opposing the globe 250. The body structure 241 defines an interior volume 242 containing at least one printed circuit board 243 that includes operative elements such a power converter, a controller module (e.g., including at least one processor and a memory), one or more transceivers (e.g., wireless transceivers), LED driver modules, sensor modules, detectors, voice recognition circuitry, and the like. The light bulb 240 may include any suitable features disclosed herein, and is preferably arranged to execute any one or more functions and/or method steps described herein.

FIGS. 26A-26E illustrate a light bulb including multiple (e.g., five or more) separately controllable groups of LEDs arranged on five non-coplanar emitter support surfaces according to one embodiment of the disclosure. The LEDs 267A-267E are arranged on a five non-coplanar emitter support surface 266A-266E, which may be elevated relative to a heatsink 265 of the light bulb 260. Each emitter support surface 266A-266E includes multiple LEDs 267A-267E. The light bulb 260 includes a body structure 261 having an associated external heatsink 265. A light-transmissive globe or lens 270 is arranged to cover the LEDs 267A-267E. An Edison (screw-type) connector including a threaded lateral contact 272 and a foot contact 271 extend from one end of the body structure 261 opposing the globe 270. The body structure 261 defines an interior volume 262 containing at least one printed circuit board 263 that includes operative elements such a power converter, a controller module (e.g., including at least one processor and a memory), one or more transceivers (e.g., wireless transceivers), LED driver modules, sensor modules, detectors, voice recognition circuitry, and the like. The light bulb 260 may include any suitable features disclosed herein, and is preferably arranged to execute any one or more functions and/or method steps described herein.

FIGS. 27A-27E illustrate a light bulb 280 including multiple (e.g., five or more) separately controllable groups of LEDs 287A-287F arranged on six non-coplanar support surfaces 286A-286F each arranged generally parallel to a longitudinal axis of the light bulb according to one embodiment. The six non-coplanar emitter support surfaces 286A-286F extend upward from a pedestal 284 and are elevated relative to a heatsink 285 of the light bulb 280. Each emitter support surface 286A-286F includes multiple LEDs 287A-287F. The light bulb 280 includes a body structure 281 having an associated external heatsink 285. Although not shown, a light-transmissive globe or lens may be joined to a shoulder portion 289 of the heatsink 285 and arranged to cover the LEDs 287A-287F and emitter support surfaces 286A-286F. An Edison (screw-type) connector including a threaded lateral contact 292 and a foot contact 291 extend from one end of the body structure 281. The body structure 281 defines an interior volume 282 containing at least one printed circuit board 283 that includes operative elements such a power converter, a controller module (e.g., including at least one processor and a memory), one or more transceivers (e.g., wireless transceivers), LED driver modules, sensor modules, detectors, voice recognition circuitry, and the like. The light bulb 280 may include any suitable features disclosed herein, and is preferably arranged to execute any one or more functions and/or method steps described herein.

Figure 28A:
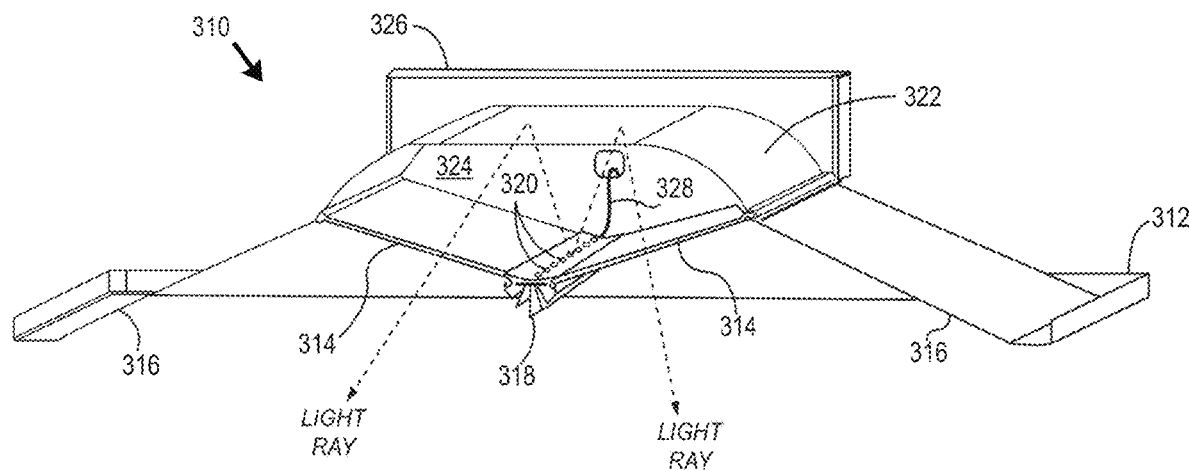
FIG. 28A is a cross-sectional perspective view of a troffer-based lighting fixture according to one embodiment of the disclosure, illustrating how light emanates from emitters of the light fixture and is reflected to be transmitted through lenses of the lighting fixture.

FIG. 28A provides a cross-sectional perspective view of a lighting device in the form of a troffer-based lighting fixture 310 according to one embodiment of the disclosure. This particular lighting fixture is substantially similar to the CR and CS series of troffer-type lighting fixtures that are manufactured by Cree, Inc. of Durham, N.C. While the disclosed lighting fixture 310 employs an indirect lighting configuration wherein light is initially emitted upward from a light source and then reflected downward, lighting devices including direct lighting configurations are within the scope of the present disclosure.

In general, troffer-type lighting fixtures, such as the lighting fixture 310, are designed to mount in, on, or from a ceiling, such as a drop ceiling (not shown) of a commercial, educational, or governmental facility. As illustrated in FIG. 28A, the lighting fixture 310 includes a square or rectangular outer frame 312. A central portion of the lighting fixture 310 includes two rectangular lenses 314, which are generally transparent, translucent, or opaque. Reflectors 316 extend from the outer frame 312 to outer edges of the lenses 314. The lenses 314 effectively extend between the innermost portions of the reflectors 316 to an elongated heatsink 318, which abuts inside edges of the lenses 314. An upwardly facing portion of the heatsink 318 provides a mounting structure for an LED array 320, which supports one or more rows of LEDs oriented to primarily emit light upwards toward a concave cover 322. The volume bounded by the cover 322, the lenses 314, and the heatsink 318 provides a mixing chamber 324. Light emanates upward from the LED array 320 toward the cover 322 and is reflected downward through the respective lenses 314, as illustrated in FIG. 28A. Some light rays will reflect multiple times within the mixing chamber 324 and effectively mix with other light rays, such that a desirably uniform light is emitted through the respective lenses 314.

Figure 28B:
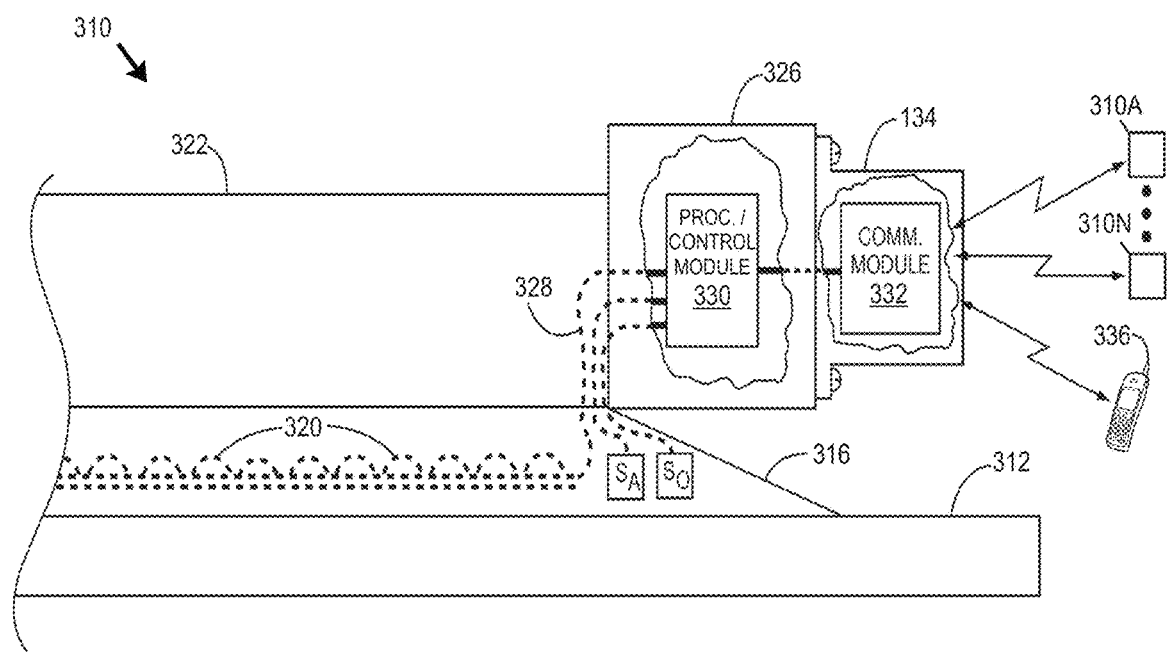
FIG. 28B illustrates a processing/control module provided in an electronics housing of the lighting fixture of FIG. 28A and a communication module in an associated housing coupled to the exterior of the electronics housing according to one embodiment of the disclosure.

As shown in FIG. 28B, an electronics housing 326 may be mounted at one end of the lighting fixture 310 to house some or all electronics used to power and control the LED array 320. These electronics are coupled to the LED array 320 through appropriate cabling 328. The electronics provided in the electronics housing 326 may be divided into a driver module 330 and a communication module 332. The communication module 332 may communicate with one or more external devices such as a user input element 336 (which may optionally be embodied in a smartphone, tablet computer, a wireless remote controller, or the like), and one or more other lighting devices (e.g., fixtures) 310A-310N. The communication module 332 may be arranged in a secondary housing 334 that is mechanically coupleable to the electronics housing 326 to promote modularity, upgradeability, and/or serviceability. The lighting fixture 310 further includes a sensor module including one or more sensors, such as occupancy sensors $S_O$, ambient light sensors $S_A$, temperature sensors, sound sensors (microphones), image (still or video) sensors, and the like. In certain embodiments, one or more sensors may be arranged external to or remote from the lighting device 310. Additionally, one or more wired user input elements (not shown) may optionally be arranged in communication with the communication module 332 and/or the driver module 330.

Figure 29D:
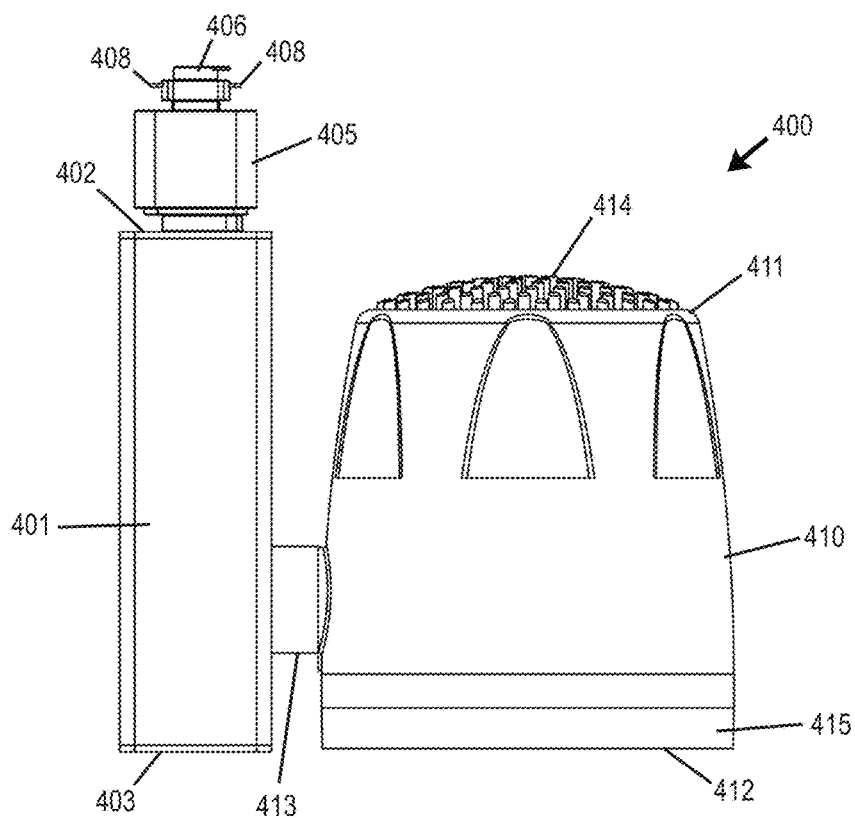
FIG. 29D is a side elevation view of the lighting device of FIGS. 29A-29C in the first position.
Figure 29E:
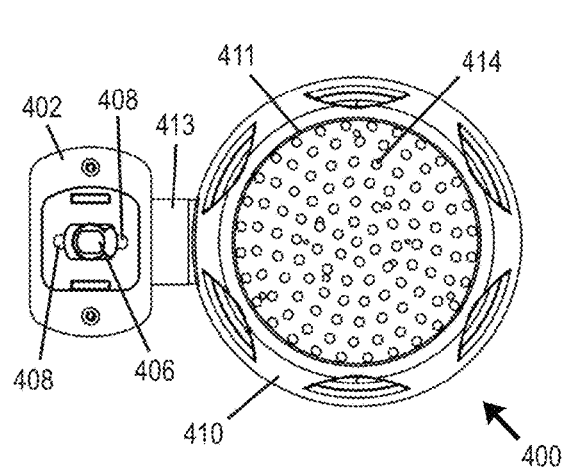
FIG. 29E is a top plan view of the lighting device of FIGS. 29A-29D in the first position.
Figure 29F:
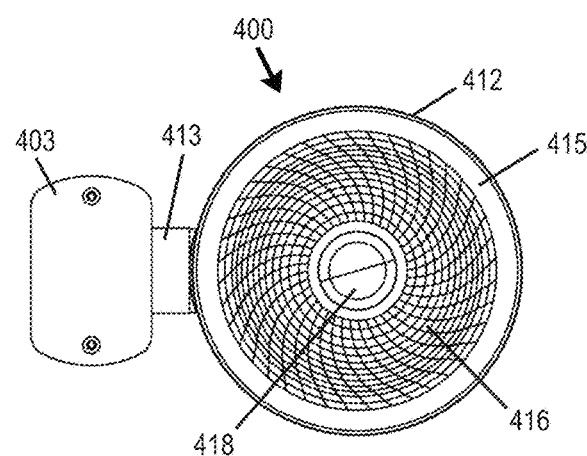
FIG. 29F is a bottom plan view of the lighting device of FIGS. 29A-29E in the first position.
Figure 29G:
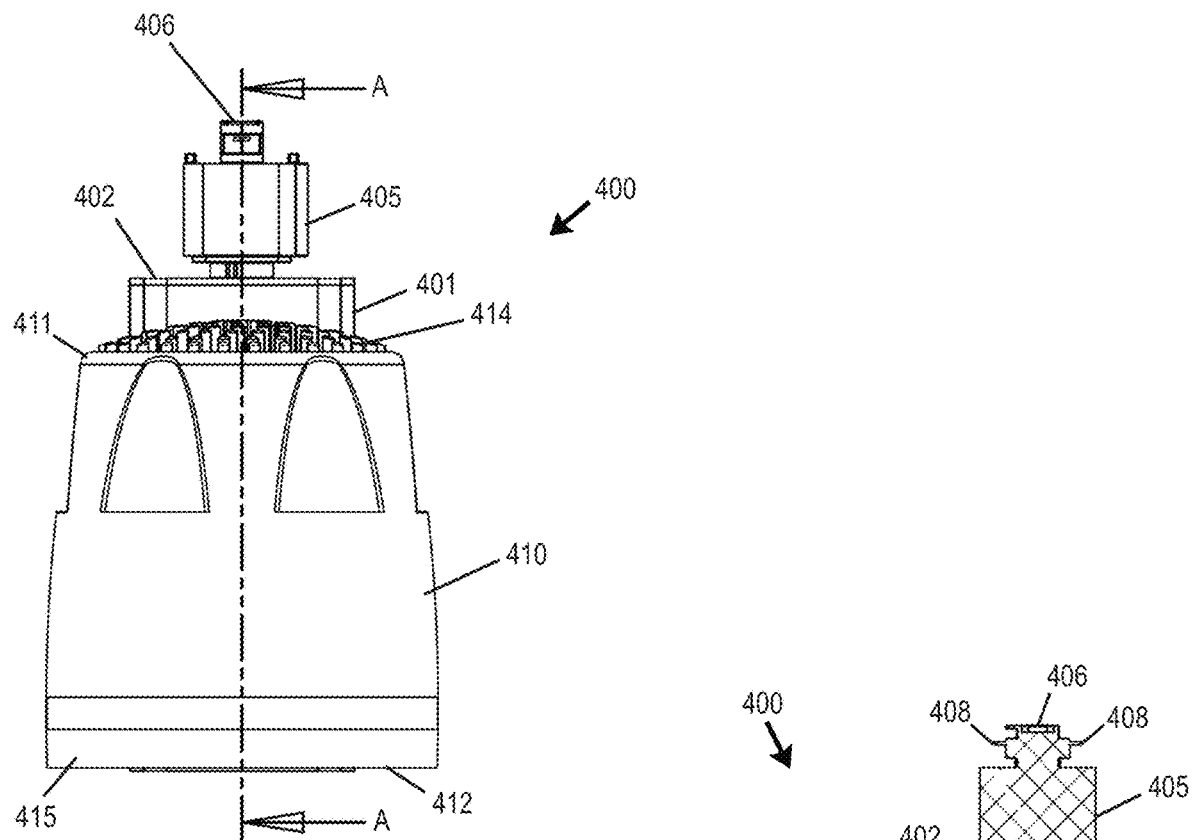
FIG. 29G is a front elevation view of the lighting device of FIGS. 29A-29F in the first position.
Figure 29H:
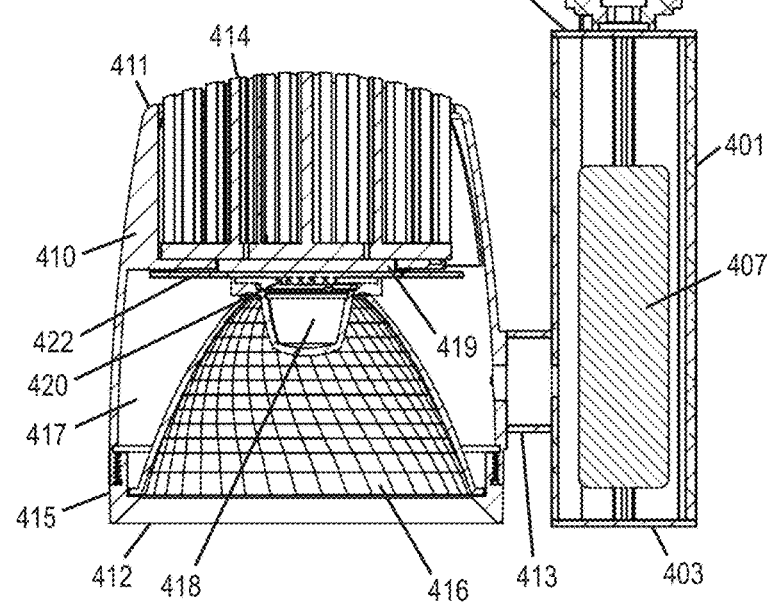
FIG. 29H is a side cross-sectional view of the lighting device of FIGS. 29A-29G in the first position, taken along section line A-A shown in FIG. 29G.

FIGS. 29A-29H illustrate a lighting device according to one embodiment of the disclosure, embodied in a track light fixture 400 intended to be supported by a wall- or ceiling-mounted track (not shown). The track light fixture 400 includes a light housing 410 coupled to a driver box 401 via a pivot joint 413. A track adapter 405, which may be arranged to pivot relative to the driver box 401, is positioned above the driver box 401 and includes a protruding portion 406 with electrical contacts or terminals 408 configured to interface with, and receive electric current from, a conventional wall- or ceiling-mounted track. The driver box 401 may be formed of extruded metal or another suitable material, and is closed with upper and lower end caps 402, 403, respectively. The driver box 401 may contain one or more LED driver components 407 (as shown in FIG. 29H) such as circuit boards including operative elements such as a power converter, a controller module (e.g., including at least one processor and a memory), one or more transceivers (e.g., wireless transceivers), LED driver modules, sensor modules, detectors, voice recognition circuitry, and the like. The pivot joint 413 extends between a side wall of the driver box 401 and a lateral portion of the light housing 410. The light housing 410 may be generally cylindrical in shape (e.g., with a slight reduction in diameter proximate to the upper edge 411 thereof) with multiple longitudinally extending pin fins 414 arranged proximate to an upper edge 411, and with a substantially conical reflector 416 and a bezel 415 arranged proximate to a lower edge 412. In certain embodiments, the reflector 416 may be configured to output light emissions having a beam angle of less than 45 degrees. In certain embodiments, the light housing 410 may be formed of metal (e.g., aluminum) by die casting or another process known in the art.

As shown in FIGS. 29F and 29H, the reflector 416 and a diffuser lens 418 are arranged within the light housing 410 to direct light to exit the housing past the bezel 415 and the lower edge 412 of the light housing 410. The diffuser lens 418 preferably eliminates presence of any visible color bands in emissions output by the track light fixture 400, and promotes emissions that are highly uniform in character. The reflector 416 may be faceted and/or include any desirable surface features or patterns to shape light emissions of the track light fixture 400. As shown in FIG. 29H, the diffuser lens 418 is arranged to receive light emissions from LEDs 420 supported by a control board 422 in conductive thermal communication with the pin fins 414, optionally by way of one or more intermediately arranged heat spreading elements 419. The pin fins 414 may be embodied in any suitable shape, such as cylinders, cones, elongated trapezoids, or the like, and optionally may be tapered in character. The LEDs 420 preferably include multiple groups (or strings) of LEDs of different output characteristics or colors (e.g., short wavelength blue, red, cyan (or long wavelength blue), green, and white)). The control board 422 and the reflector 416 may both be arranged within a cavity 417 defined by an inner surface of the light housing 410. One or more LED driver components (not shown) may be optionally arranged on the control board 422, and may cooperate with LED driver components 407 arranged in the driver box 401. As shown in FIG. 29H, the pin fins 414 may be arranged within a central cavity defined in an upper portion of the light housing 410, such that heat can escape between and above the pin fins 414, but only an uppermost portion of each pin fin 414 is visible from a side view of the light housing 410 (as shown in FIGS. 29D and 29G). The track light fixture 400 may include any suitable features disclosed herein, and is preferably arranged to execute any one or more functions and/or method steps described herein.

Figure 30:
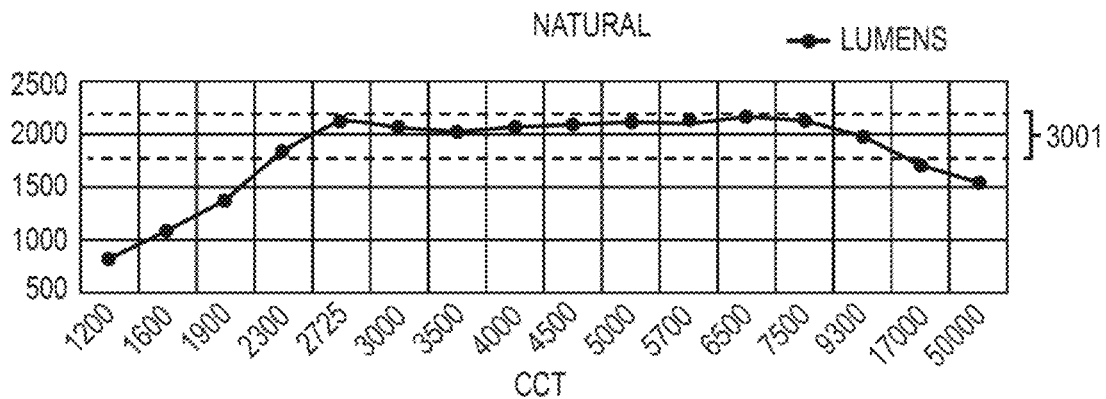
FIG. 30 is a line chart of lumens versus correlated color temperature (CCT) for emissions of a lighting device embodied in a track light fixture according to FIGS. 29A-29H, including five different groups (or strings) of LEDs (namely, short wavelength blue, red, cyan (or long wavelength blue), green, and white) when operated in a first (e.g., "natural") operating mode intended to promote high average Color Rendering Index (CRI Ra) values.

FIG. 30 is a line chart of lumens versus correlated color temperature (CCT) for emissions of a lighting device embodied in a track light fixture according to FIGS. 29A-29H, including five different groups (or strings) of LEDs (namely, short wavelength blue, red, cyan (or long wavelength blue), green, and white) when operated in a first (e.g., "natural") operating mode intended to promote high average Color Rendering Index (CRI Ra) values. A desirable minimum range of lumen values (e.g., from about 1800 to about 2200 lumens) is depicted by a range 3101 bounded by dashed horizontal lines. As shown in FIG. 30, lumen values are relatively constant for CCT values between about 2800K and about 8500K, and lumen values within the desirable minimum range 3101 are attained for CCT values of from about 2500K to at least about 10,000K.

Figure 31:
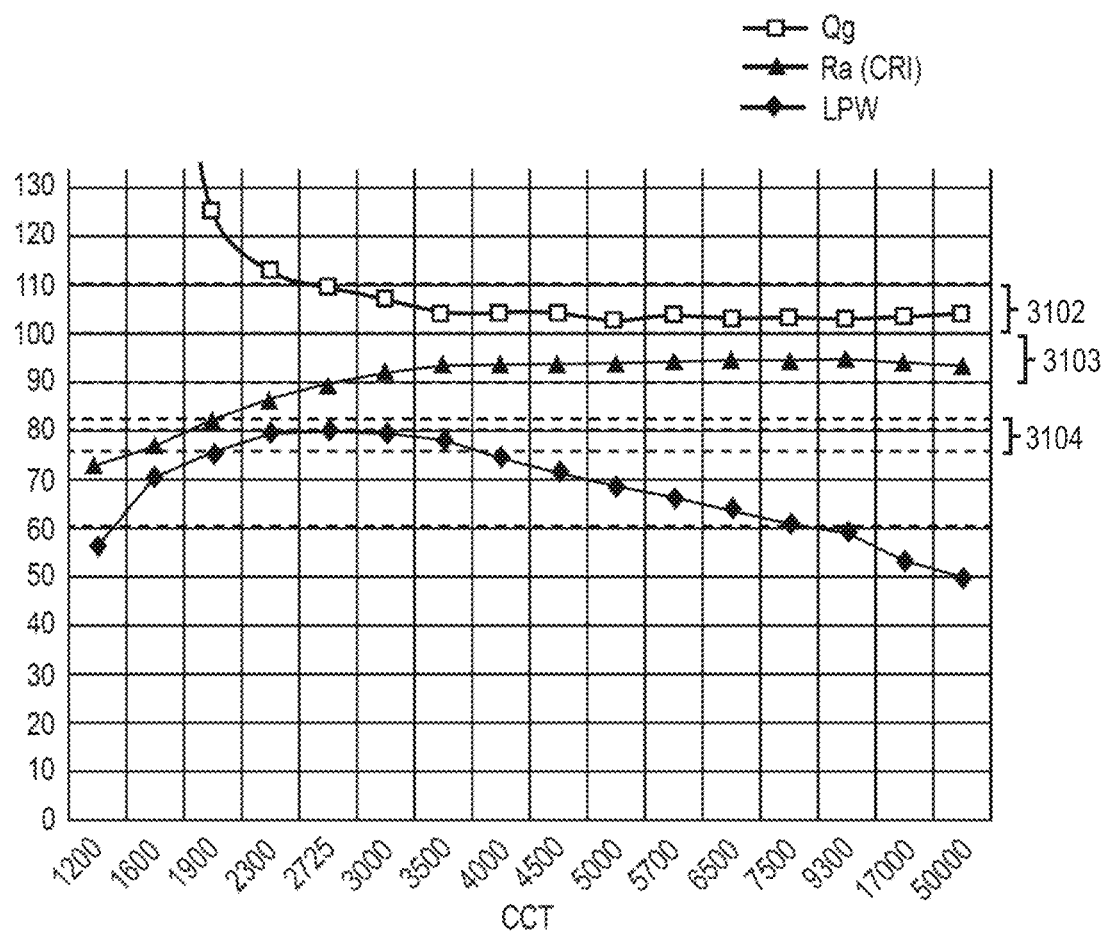
FIG. 31 is a line chart plotting each of relative gamut area (Qg), average Color Rendering Index (CRI Ra), and luminous efficacy (lumens per watt or LPW) versus correlated color temperature (CCT) for emissions of a lighting device embodied in a track light fixture according to FIGS. 29A-29H, including five different groups (or strings) of LEDs (namely, short wavelength blue, red, cyan (or long wavelength blue), green, and white) when operated in the first operating mode intended to promote high color rendering (CRI Ra) values.

FIG. 31 is a line chart plotting each of relative gamut area (Qg), average Color Rendering Index (CRI Ra), and luminous efficacy (lumens per watt or LPW) versus correlated color temperature (CCT) for emissions of a lighting device embodied in a track light fixture according to FIGS. 29A-29H, including five different groups (or strings) of LEDs (namely, short wavelength blue, red, cyan (or long wavelength blue), green, and white) when operated in the first (e.g., high average Color Rendering Index) operating mode described in connection with FIG. 30. A desirable minimum range of Qg values (e.g., from about 100 to about 110) is depicted by a range 3202 bounded by a first pair of dashed horizontal lines, a desirable minimum range of CRI Ra values (e.g., from about 90 to 100) is depicted by a range 3203 bounded by a second pair of dashed horizontal lines, and a desirable minimum range of lumens per watt values (e.g., from about 75 to about 83) is depicted by a range 3204 bounded by a third pair of dashed horizontal lines. As shown in FIG. 31, high Qg values are obtained from low CCT light emissions and decline (e.g., in an asymptotic manner) to a relatively constant value of between 100 and 110 for higher CCT light emissions. As further shown in FIG. 31, lower CRI Ra values are obtained at low CCT light emissions, and rise (e.g., in an asymptotic manner) to a relatively constant value of between 90 and 100 for higher CCT light emissions. As additionally shown in FIG. 31, luminous flux (lumens per watt or LPW) values peak (at a value of about 80 LPW) for light emissions with CCT values between about 2400K and about 3300K, with lower LPW values obtained for light emissions with CCT values below and above the foregoing CCT range.

Figure 32:
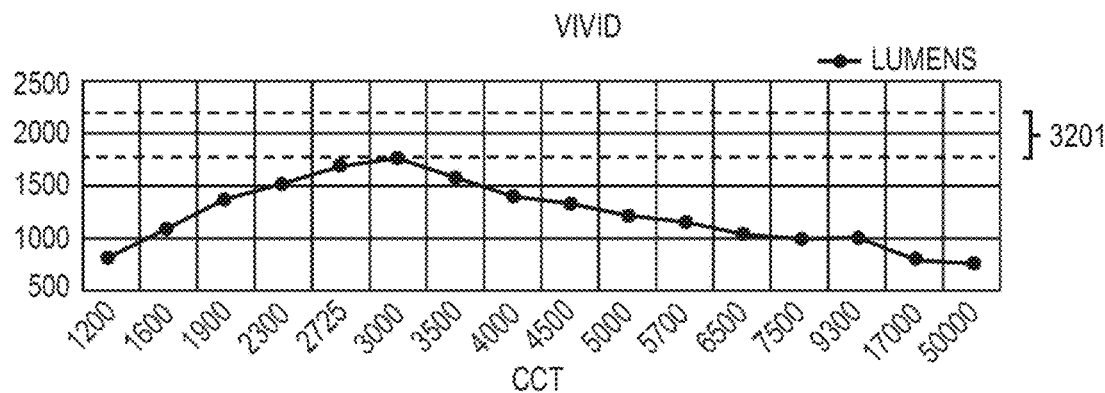
FIG. 32 is a line chart plotting lumens versus correlated color temperature (CCT) for emissions of a lighting device embodied in a track light fixture according to FIGS. 29A-29H, including five different groups (or strings) of LEDs (namely, short wavelength blue, red, cyan (or long wavelength blue), green, and white) when operated in a second (e.g., "vivid") operating mode intended to promote enhanced Qg values.

FIG. 32 is a line chart plotting lumens versus correlated color temperature (CCT) for emissions of a lighting device embodied in a track light fixture according to FIGS. 29A-29H, including five different groups (or strings) of LEDs (namely, short wavelength blue, red, cyan (or long wavelength blue), green, and white) when operated in a second (e.g., "vivid") operating mode intended to promote enhanced Qg values. A desirable minimum range of lumen values (e.g., from about 1800 to about 2200 lumens) is depicted by a range 3301 bounded by dashed horizontal lines. As shown in FIG. 32, lumen values peak for light emissions having a CCT value of about 3200K, with lower lumen values obtained for light emissions with CCT values below and above the foregoing CCT range.

Figure 33:
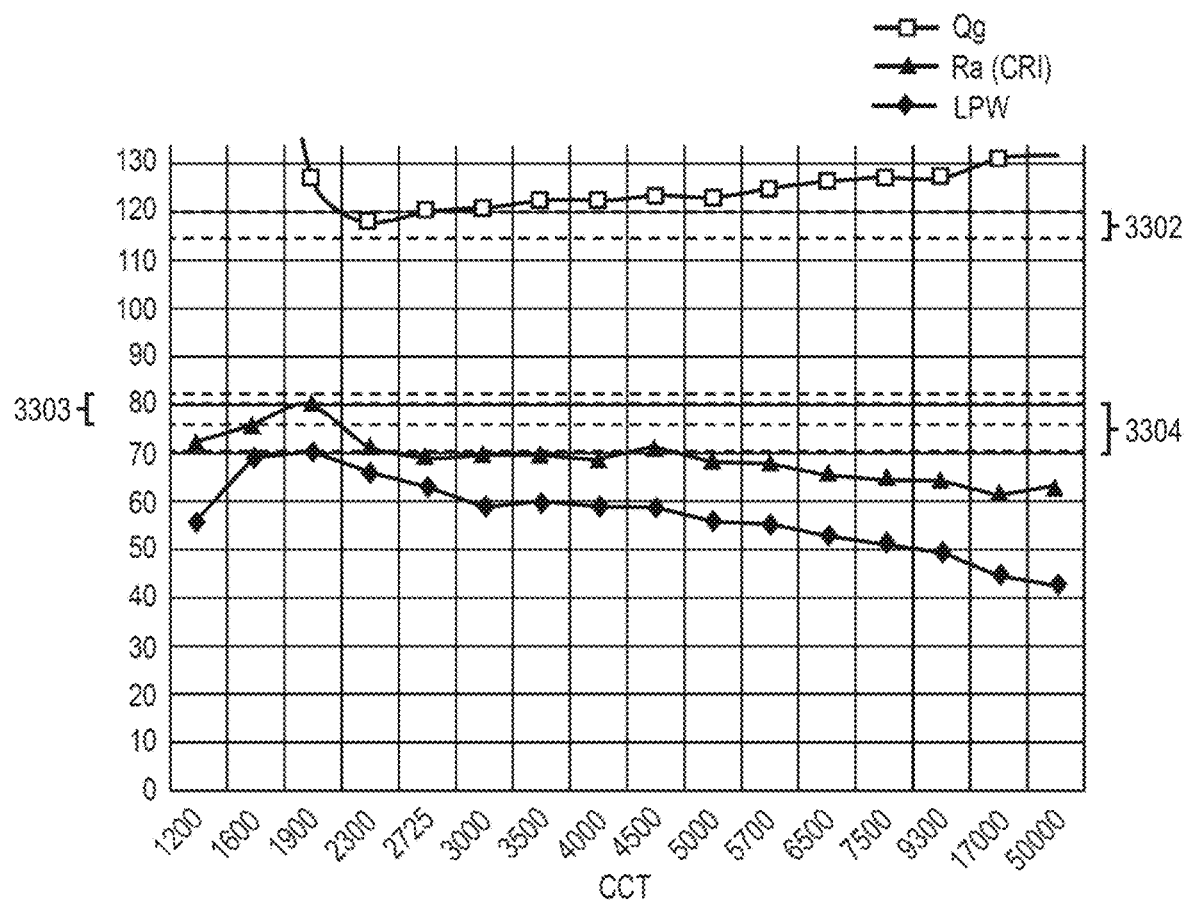
FIG. 33 is a line chart plotting each of relative gamut area (Qg), average Color Rendering Index (CRI Ra), and luminous efficacy (lumens per watt or LPW) versus correlated color temperature (CCT) for emissions of a lighting device embodied in a track light fixture according to FIGS. 29A-29H, including five different groups (or strings) of LEDs (namely, short wavelength blue, red, cyan (or long wavelength blue), green, and white) when operated in the second operating mode intended to promote enhanced Qg values.

FIG. 33 is a line chart plotting each of relative gamut area (Qg), average Color Rendering Index (CRI Ra), and luminous efficacy (lumens per watt) versus correlated color temperature for emissions of a lighting device embodied in a track light fixture according to FIGS. 29A-29H, including five different groups (or strings) of LEDs (namely, short wavelength blue, red, cyan (or long wavelength blue), green, and white) when operated in the second (enhanced Qg) operating mode described in conjunction with FIG. 32. A desirable minimum range of enhanced Qg values (e.g., from about 115 to about 120) is depicted by a range 3402 bounded by a first pair of dashed horizontal lines, a desirable minimum range of CRI Ra values (e.g., from about 75 to about 83) is depicted by a range 3403 bounded by a second pair of dashed horizontal lines, and a desirable minimum range of lumens per watt values (e.g., from about 70 to about 80) is depicted by a range 3404 bounded by a third pair of dashed horizontal lines. As shown in FIG. 33, higher Qg values are obtained for light emissions having CCT values above and below about 2500K. As further shown in FIG. 33, CRI Ra values peak (at a value of about 80) for light emissions having a CCT value of about 2100K and are lower for light emissions having CCT values above and below about 2100K. As additionally shown in FIG. 33, luminous flux (lumens per watt or LPW) values peak (at a value of about 70 LPW) for light emissions having a CCT value of about 2100K and are lower for light emissions having CCT values above and below about 2100K.

Figure 34:
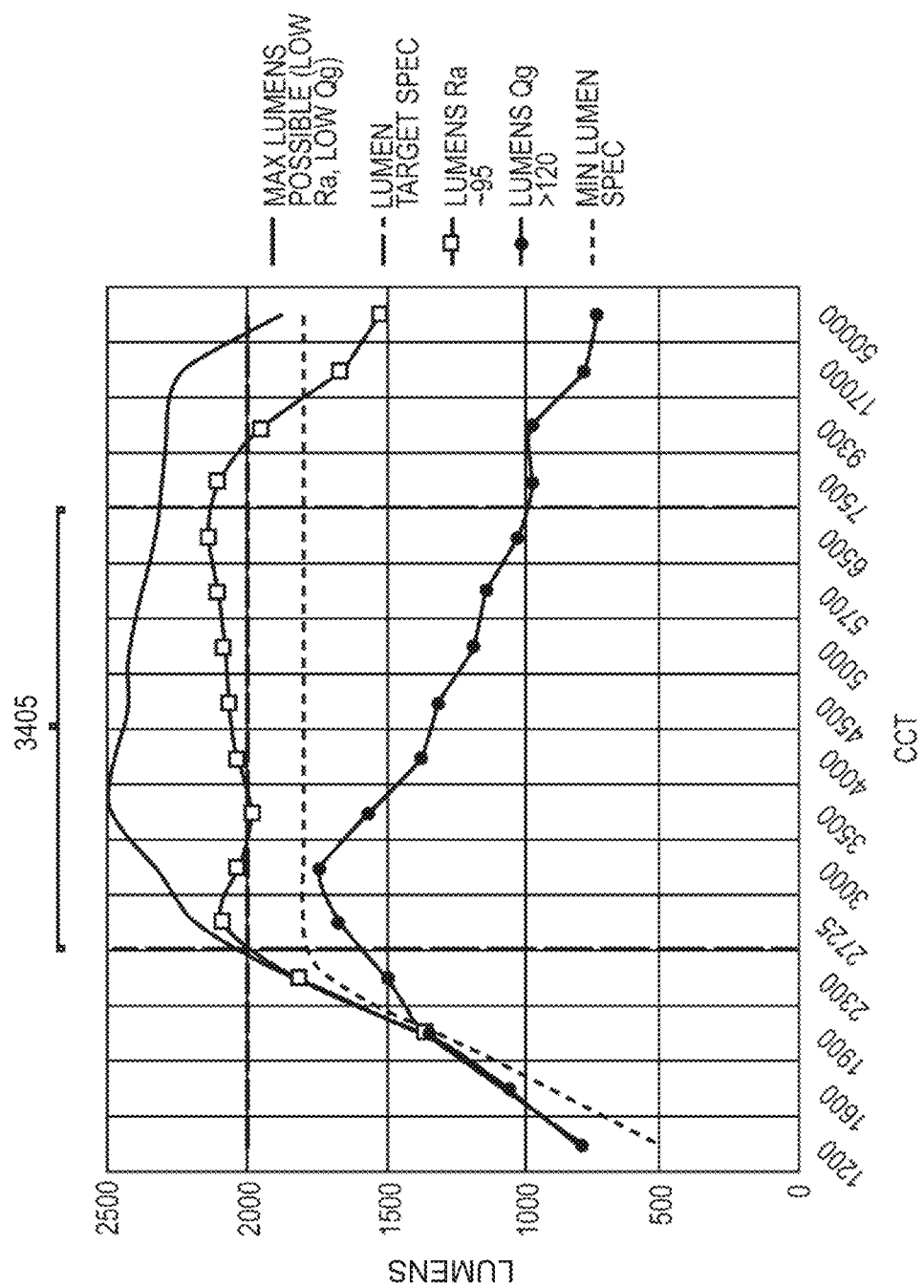
FIG. 34 is a line chart plotting lumens versus correlated color temperature (CCT) for a lighting device embodied in a track light fixture according to FIGS. 29A-29H according to three different operating modes, including a maximum possible brightness mode, a high average CRI Ra mode, and a high Qg mode, with comparison of a lumen target specification and a minimum lumen specification.

FIG. 34 is a line chart plotting lumens versus correlated color temperature for a lighting device embodied in a track light fixture according to FIGS. 29A-29H according to three different operating modes, including a maximum possible brightness mode, a high average CRI Ra mode (with CRI Ra values of at least 95), and a high Qg mode (with Qg values of at least 120), with comparison of a lumen target specification and a minimum lumen specification. As shown in FIG. 34, maximum possible lumens are obtained for light emissions with a CCT value of about 3800K. As between the high CRI Ra and high Qg operating modes, higher lumens are obtained for the high CRI Ra operating mode, with a local peak value attained for light emissions having a CCT value of about 2800K, and another slightly higher peak value attained for light emissions having a CCT value of about 8500K, with lumens declining for CCT values below about 2800K and above about 8500K. For the high Qg operating mode, maximum lumens are obtained for light emissions having a CCT value of about 3200K, with lower lumen values being obtained for light emissions having CCT values above or below 3200K. Desirable CCT values (e.g., from about 2725K to about 7500K) are depicted by a range 3505 bounded by a pair of dashed vertical lines.

Figure 35:
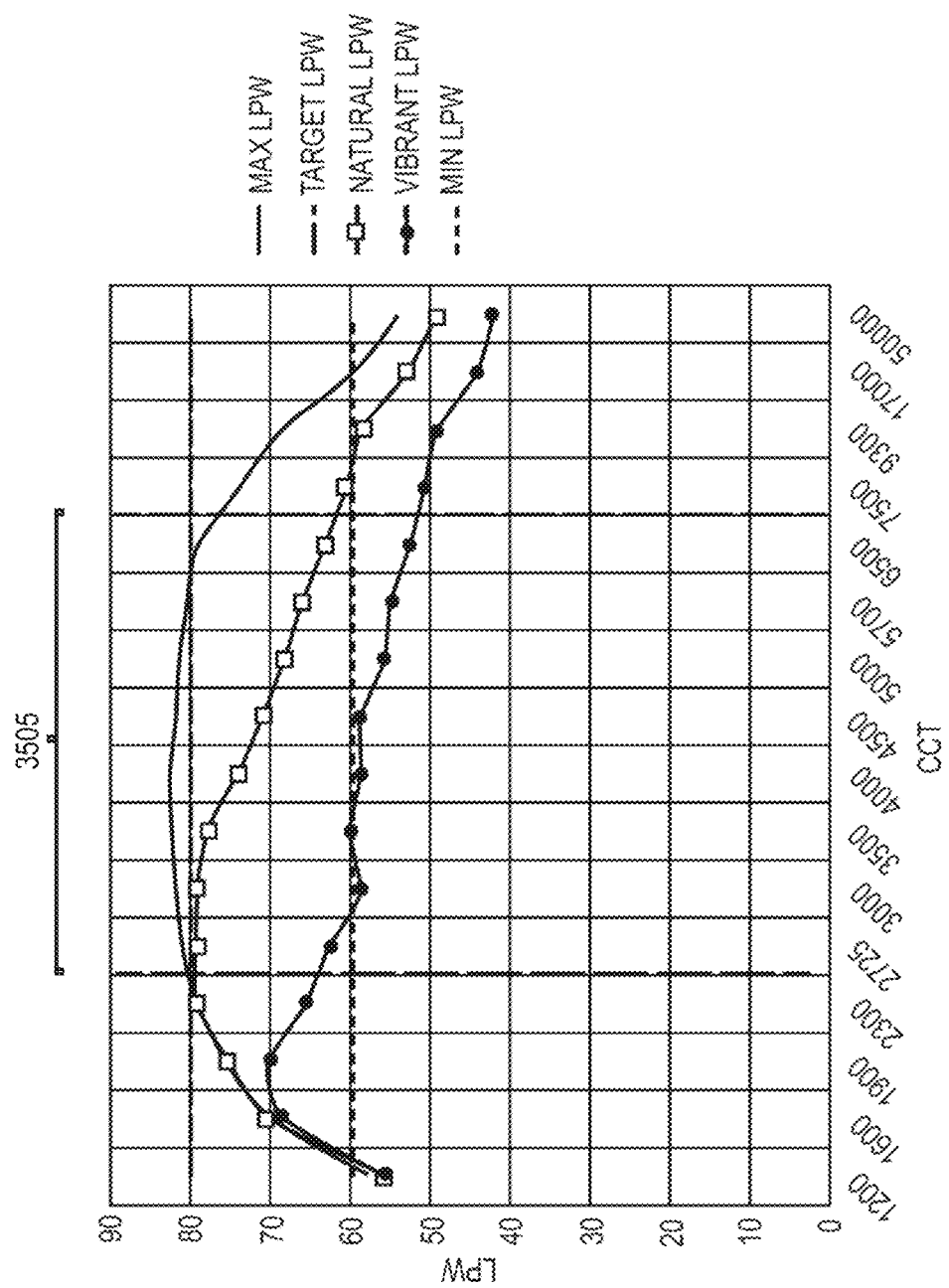
FIG. 35 is line chart plotting luminous efficacy (lumens per watt or LPW) versus correlated color temperature (CCT) for a lighting device embodied in a track light fixture according to FIGS. 29A-29H according to three different operating modes, including a maximum possible brightness mode, a high average CRI Ra mode, and a high Qg mode, with comparison of a lumen per watt target specification and a minimum lumen per watt specification.

FIG. 35 is line chart plotting luminous efficacy (lumens per watt) versus correlated color temperature for a lighting device embodied in a track light fixture according to FIGS. 29A-29H according to three different operating modes, including a maximum possible brightness mode, a high average CRI Ra mode, and a high Qg mode, with comparison of a lumen per watt target specification and a minimum lumen per watt specification. As shown in FIG. 35, maximum possible luminous efficacy is obtained for light emissions with a CCT value of about 4200K, but maximum possible lumen values are relatively constant for light emissions having CCT values of from about 3500K to about 4500K. As between the high CRI Ra and high Qg operating modes, higher luminous efficacy is obtained for the high CRI Ra operating mode, with maximum values attained for light emissions having CCT values in a range of from about 2500K to about 3200K, and lower luminous efficacy values attained for CCT values outside the foregoing range. For the high Qg operating mode, maximum luminous efficacy is obtained for light emissions having a CCT value of about 2100K, with lower lumen values being obtained for light emissions having CCT values above or below 2100K. Desirable CCT values (e.g., from about 2725K to about 7500K) are depicted by a range 3605 bounded by a pair of dashed vertical lines. A desirable minimum luminous efficacy of about 60 lumens per watt is depicted by a dashed horizontal line, with all high CRI Ra operating mode luminous efficacy values being above this threshold for the range of desirable CCT values, but only two high Qg operating mode values being at or above the 60 lumen per watt threshold.

Figure 36:
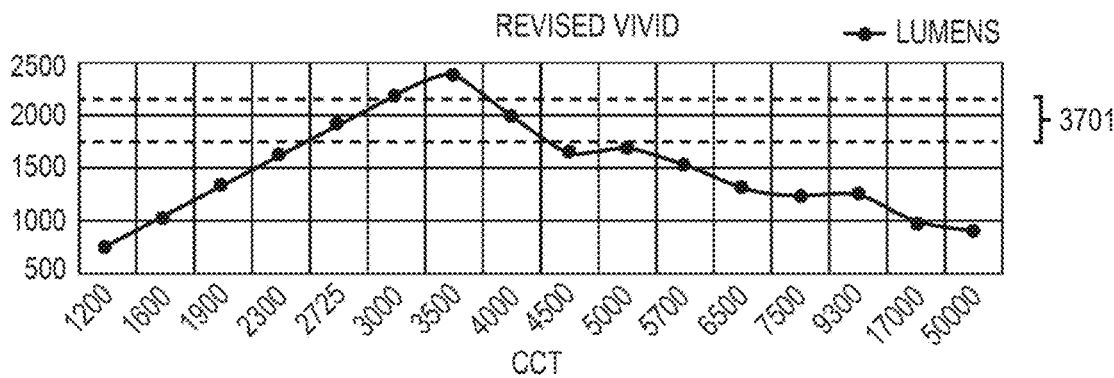
FIG. 36 is a line chart plotting lumens versus correlated color temperature (CCT) for emissions of a lighting device embodied in a track light fixture according to FIGS. 29A-29H, including five different groups (or strings) of LEDs (namely, short wavelength blue, red, cyan (or long wavelength blue), green, and white) when operated in a third (e.g., "highly vivid") operating mode intended to promote further enhanced Qg values.

FIG. 36 is a line chart plotting lumens versus correlated color temperature for emissions of a lighting device embodied in a track light fixture according to FIGS. 29A-29H, including five different groups (or strings) of LEDs (namely, short wavelength blue, red, cyan (or long wavelength blue), green, and white) when operated in a third (e.g., "highly vivid") operating mode intended to promote further enhanced Qg values. A desirable minimum range of lumen values (e.g., from about 1800 to about 2200 lumens) is depicted by a range 3301 bounded by dashed horizontal lines. As shown in FIG. 36, lumen values are highest for light emissions having a CCT value of about 3700K and decline for light emissions with CCT values above and below the foregoing CCT value.

Figure 37:
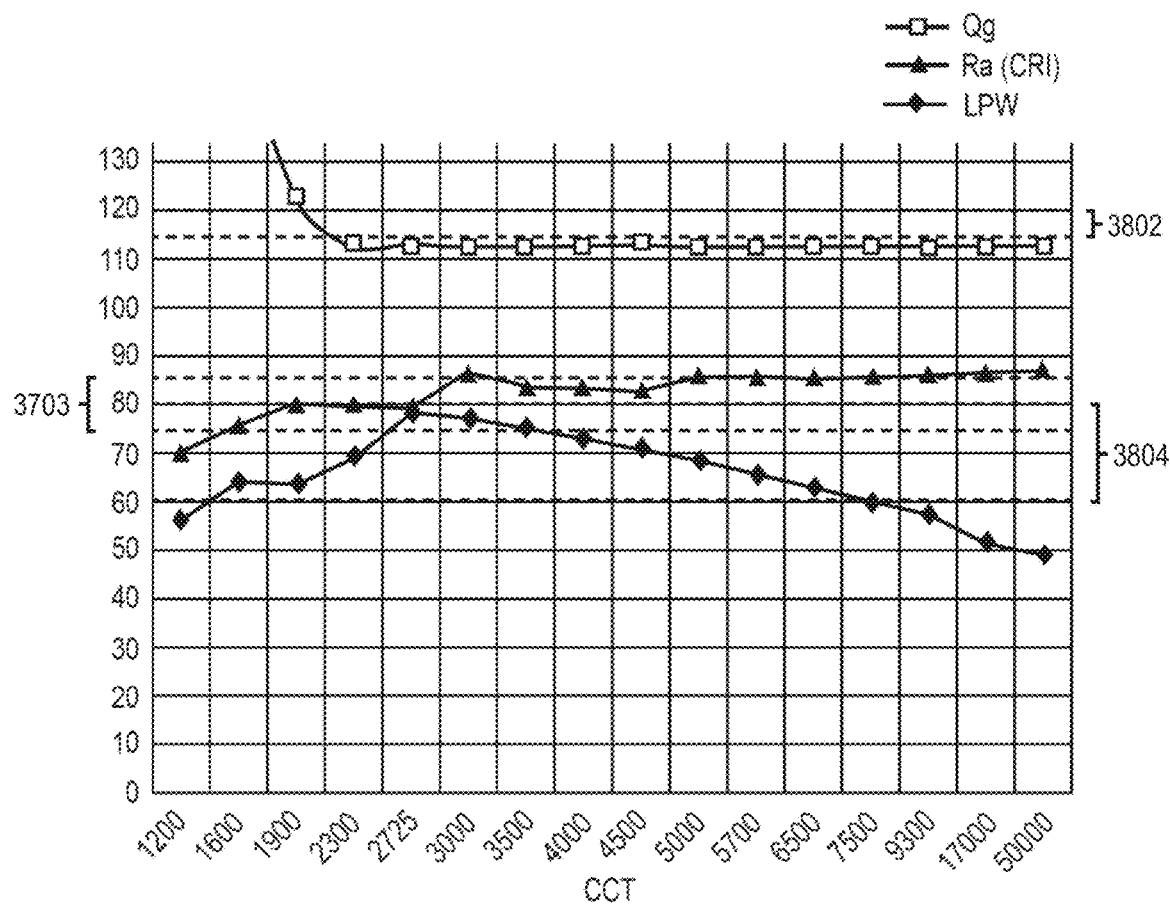
FIG. 37 is a line chart plotting each of relative gamut area (Qg), average Color Rendering Index (CRI Ra), and luminous efficacy (lumens per watt or LPW) versus correlated color temperature (CCT) for emissions of a lighting device embodied in a track light fixture according to FIGS. 29A-29H, including five different groups (or strings) of LEDs (namely, short wavelength blue, red, cyan (or long wavelength blue), green, and white) when operated in the third operating mode intended to promote further enhanced Qg values.

FIG. 37 is a line chart plotting each of relative gamut area (Qg), average Color Rendering Index (CRI Ra), and luminous efficacy (lumens per watt) versus correlated color temperature for emissions of a lighting device embodied in a track light fixture according to FIGS. 29A-29H, including five different groups (or strings) of LEDs (namely, short wavelength blue, red, cyan (or long wavelength blue), green, and white) when operated in the third (highly vivid or further enhanced Qg) operating mode described in connection with FIG. 36. A desirable minimum range of enhanced Qg values (e.g., from about 115 to about 120) is depicted by a range 3802 bounded by a first pair of dashed horizontal lines, a desirable minimum range of CRI Ra values (e.g., from about 75 to about 85) is depicted by a range 3803 bounded by a second pair of dashed horizontal lines, and a desirable minimum range of lumens per watt values (e.g., from about 60 to about 80) is depicted by a range 3804 bounded by a third pair of dashed horizontal lines. As shown in FIG. 37, Qg values are relatively constant for light emissions having CCT values of from about 2500K to above 10,000K. As further shown in FIG. 37, CRI Ra values rise to a local peak (at a value of about 86) for light emissions having a CCT value of about 3200K, then dip slightly (while remaining at or above about 82) and generally exhibit a slight increase with increased CCT for light emissions having CCT values higher than 3200K. As additionally shown in FIG. 33, luminous flux (lumens per watt or LPW) values peak (at a value of about 76 LPW) for light emissions having a CCT value of about 2100K, and are lower for light emissions having CCT values above and below about 2100K.

The preceding line charts demonstrate that a lighting device with multiple (e.g., five) LED groups or strings may be operated in a first operating mode providing emissions having high average color rendering index values in combination with relatively high luminous flux values. The same lighting device may be operated in a second ("vivid") operating mode providing emissions with enhanced Qg values with reduced color rendering, lumen output, and luminous efficacy values, and may be operated in a third ("highly vivid") operating mode providing emissions with further enhanced Qg values with further reduced color rendering and luminous efficacy values. In certain lighting environments, these reduced color rendering, lumen output, and luminous efficacy values may be considered acceptable tradeoffs to obtain emissions with enhanced vividness. In certain embodiments, a combination of emitters may generate emissions with CRI Ra or Qg values that exceed minimum thresholds, and an operating mode may be adjusted to reduce or eliminate "excess" CRI Ra or Qg values to increase lumens and luminous efficacy.

In certain embodiments, a lighting device as disclosed herein may include multiple preset and/or user-defined operating modes that may be selected by a user. In certain embodiments, multiple user-selected operating modes may provide aggregate emissions with similar or substantially the same brightness (e.g., total lumens).

Wireless Interfaces

Figure 38B:
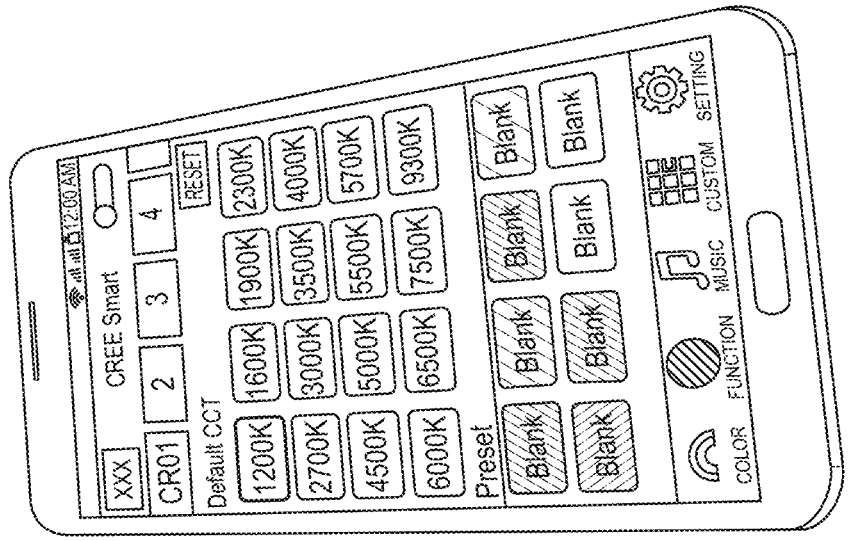
FIG. 38B illustrates a portable digital communication device displaying another screen of a "CREE Smart" user interface application arranged to control a lighting device as described herein according to one embodiment of the disclosure.
Figure 38A:
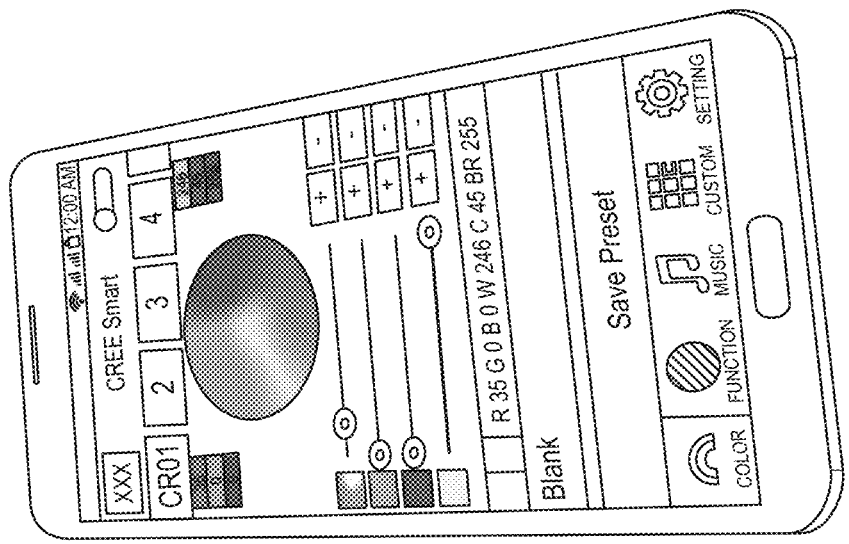
FIG. 38A illustrates a portable digital communication device displaying one screen of a "CREE Smart" user interface application arranged to control a lighting device as described herein according to one embodiment of the disclosure.

FIG. 38A illustrates a portable digital communication device displaying one screen of a "CREE Smart" user interface application arranged to control a lighting device as described herein according to one embodiment of the disclosure. As shown in FIG. 38A, different groups of solid state light emitters may be separately controlled by a user (e.g., via a slider bar, a dial, or other means) to permit adjustment of various light output parameters. In certain embodiments, color coordinates for aggregate color point and/or individual source groups may be displayed to a user and/or logged.

FIG. 38B illustrates a portable digital communication device displaying another screen of a "CREE Smart" user interface application arranged to control a lighting device as described herein according to one embodiment of the disclosure. As shown in FIG. 38B, a user interface may include multiple predefined operating modes or operating instruction sets available for selection by a user. Additionally, a user may modify or create various presets (e.g., algorithms, operating modes, or operating instruction sets) and store such presets locally in a digital computing or digital communication device, and/or store such presets in a memory associated with a lighting device. In certain embodiments, a user may retrieve one or more algorithms via a communication network, and communicate one or more algorithms to a memory of a lighting device to supplement or supplant one or more algorithms already stored in memory.

Automatic Adjustment of Light Output Parameters Based on Geospatial Position

In certain embodiments, lighting devices and/or lighting systems may be arranged to receive or determine information indicative of geospatial or geographic location (and optionally additional information such as time, time zone, and/or date) and automatically adjust one or more light output parameters based at least in part on such information to operate one or more electrically activated emitters differently on different days of a year. Light output parameters that may be adjusted according to certain embodiments include color point of emissions, color temperature of emissions, spectral content of emissions, luminous flux of emissions, and operating time. Spectral content of emissions that may be adjusted include one or more of color rendering index (e.g., CRI Ra, CRI R9, or another value), vividness (e.g., relative gamut or gamut area index), and melatonin suppression characteristics for a selected color point or CCT of aggregate emissions. In certain embodiments, a lighting system may include multiple lighting devices. In certain embodiments, a lighting device may provide light of a brightness level and spectral content (e.g., color point and/or color temperature) appropriate for the location (and preferably also appropriate for the time of day, day of week, and season). In certain embodiments, a lighting device or lighting system may further be adjusted to compensate for presence, absence, intensity, and/or color point of natural ambient light.

In certain embodiments, adjustment of one or more light output parameters based at least in part on geospatial position on different days of the year includes scheduled variation from week to week, variation from month to month, and/or variation from season to season. In certain embodiments, variation of light output parameters other than mere variation between weekday and weekend operating states, and variation of light output parameters other than semi-annual variation in daylight savings time, are contemplated. When the lighting device remains located at a given geospatial position, a base schedule for operation of emitters of the lighting device may be reestablished or automatically altered from day to day, from week to week, from month to month, or from season to season such that one or more electrically activated emitters are operated differently on different days of a year.

Various methods may be used for one or more lighting devices as disclosed herein to determine geospatial position, date, and/or time. In certain embodiments, a signal used by a lighting device or lighting system, and indicative of, or permitting derivation of, geospatial position, is provided by at least one of a user input element, a signal receiver, and one or more sensors. In certain embodiments, any one or more of a user input element, a signal receiver, and one or more sensors may be arranged in, arranged on, or supported by a body structure of a lighting device. In certain embodiments, any one or more of a user input element, a signal receiver, and one or more sensors may be physically separated from a body structure containing emitters of a lighting device, but may be arranged in communication with a driver module of a lighting device via wireless or wired communication.

In certain embodiments, a lighting device or lighting system includes, or is arranged in at least intermittent communication with, a global positioning system (GPS) receiver that is arranged to receive global positioning coordinates (e.g., latitude and/or longitude coordinates) or other information as indicative of geospatial position. A GPS receiver may also provide accurate time and date information useable by the lighting device or lighting system. In certain embodiments, a lighting device may be arranged to communicate with an electronic device that includes location sensing capability, and the lighting device may obtain location information (and/or date and time information) from the electronic device. In certain embodiments, such an electronic device may embody a smartphone or other portable digital device having integrated GPS, WiFi, and/or cellular communication capabilities that provide the portable digital device with location information, and such location information may be communicated to a lighting device by either wireless or wired means. In certain embodiments, a lighting device or lighting system includes, or is arranged in at least intermittent communication with, a signal receiver arranged to receive a signal and extract at least one Internet Protocol (IP) address from one or more proximate IP-enabled servers, routers, or other devices in order to at least approximately determine geospatial position and/or time and date information. In certain embodiments, a lighting device or lighting system may receive information indicative of, or permitting derivation of, geospatial position, as well as date and/or time information, by reception of broadcast radio and/or broadcast television signals. In certain embodiments, a lighting device or lighting system may receive information indicative of, or permitting derivation of, geospatial position, as well as date and/or time information, via signals encoded on a power line. In certain embodiments, a lighting device or lighting system includes, or is arranged in at least intermittent communication with, a light sensor arranged to receive ambient light (e.g., daylight) in order to permit determination of geospatial position. In certain embodiments, a lighting device may receive and store an ambient light signal, and analyze such information gathered over time to determine (at least approximate) geospatial position. In certain embodiments, an ambient light (or daylight) sensor may enable calculation or estimation of geospatial position based on when natural light first appears, duration of presence of natural light, and how the light varies over time (e.g., both intraday and in longer time scales such as from day to day and from month to month).

In certain embodiments, a lighting device or lighting system includes at least one signal transmitter and/or receiver, such as may be optionally embodied in at least one transceiver. In certain embodiments, a transmitter and/or receiver may be arranged to transmit and/or receive radio frequency signals.

In certain embodiments, a lighting device may communicate with one or more other lighting devices such that the devices can share information. This may be useful when a first lighting device lacks a clear connection to a desired GPS signal, user input, other external signal, or other sensory input, but when a second lighting device has a clear connection to a GPS signal. In such an instance, the second lighting device may receive a signal from a GPS satellite, a user input device, a RF receiver, or one or more sensors, and the second lighting device may transmit the received information to the first lighting device to permit the first lighting device to take appropriate action (e.g., update geospatial position, update time/date, adjust base schedule, and/or adjust operating state). In certain embodiments, lighting devices may communicate with one another via signals encoded on a power line. Thus, via either wired or wireless communication, one lighting device may propagate information to one or more other lighting devices, and the shared information may be used to automatically adjust one or more light output parameters to cause the lighting devices to operate one or more electrically activated emitters differently on different days of a year.

As noted previously, one or more light output parameters of a lighting device may be adjusted at least in part based on information indicative of geospatial or geographic location, and optionally additional information such as time, time zone, and/or date. Examples of light output parameters that may be adjusted include color point of emissions, color temperature of emissions, spectral content of emissions, intensity or luminous flux of emissions, and operating time. In certain embodiments, a lighting device includes multiple independently controllable emitters (or groups of emitters) having different color points. By altering proportion of current to different emitters having different color points, a lighting device may be adjusted to produce aggregate emissions of a range of different colors and/or color temperatures. In certain embodiments, a base schedule for a lighting device may be configured to promote wellness by providing output that promotes alertness in morning to afternoon hours, that promotes alertness and relaxation in mid-afternoon to evening hours, that promotes relaxation and sleepiness in late evening to bedtime hours, and that does not interfere with sleeping and/or does not interfere with night vision from midnight to dawn hours.

In certain embodiments, a base schedule for operation of a lighting device or lighting system may be altered or programmed by a user, such as by using one or more user input elements. For example, a user that is required to work during evening hours and to sleep during daytime hours may program a lighting device to output emissions having a high intensity and a high color temperature during evening hours to promote alertness while the user is working, with a transition to lower intensity and lower color temperature to a time allotted for the user to sleep. In certain embodiments, a user may simply shift a base schedule by a selected number of hours, based on a selected wake-up time, a selected bedtime, and/or a selected period for work or other activity requiring alertness.

In certain embodiments, a lighting device may be configured to accept user inputs to initiate actions, to accept user inputs to adjust response of a lighting device to time of day, and/or accept user inputs to adjust response to an ambient lighting condition.

In certain embodiments, color temperature of a lighting device may be synchronized to local variation of ambient light color temperature with respect to geographic location or geospatial position, time of day, and day of year. For example, a lighting device may emulate natural outdoor light levels and color spectral content when it is dawn, dusk, and midday, with such emulation matched to the geospatial position or geographic location of the lighting device.

In other embodiments, a base schedule of a lighting device may be modified, or an alternate base schedule may be selected, to mitigate symptoms of seasonal affective disorder by providing increased intensity and/or color temperature of light during at least certain times of day. In certain embodiments, a lighting device may detect that it is located in a geographic location or geospatial position consistent with increased incidence of seasonal affective disorder, and either prompt a user to select, or automatically initiate operation of, a base schedule suitable to mitigate symptoms of seasonal affective disorder.

Further Devices and Methods

In certain embodiments, a solid state lighting device disclosed herein may include a reprogrammable memory arranged to store multiple selectable algorithms each including different instructions useable by at least one processor for controlling operation of multiple solid state light emitters of the lighting device, wherein a communication interface is arranged to receive an additional algorithm for storage by the memory to permit the at least one processor to execute steps of the additional algorithm for controlling operation of the lighting device. In one embodiment, a user may obtain a new algorithm (e.g., retrieval via the Internet or other network), and then upload the new algorithm to a lighting device.

In certain embodiments, the communication interface comprises a wireless receiver or transceiver, and the wireless receiver or transceiver is arranged to receive the additional algorithm wirelessly from a digital communication device or a digital computing device. In certain embodiments, the lighting device comprises at least one transceiver arranged to communicate with at least one other solid state lighting device. In certain embodiments, a plurality of groups of solid state light emitters are provided, wherein each group of solid state light emitters is arranged to generate emissions comprising a dominant wavelength that differs from a dominant wavelength of emissions generated by each other group of solid state light emitters, wherein each group of solid state light emitters is independently controllable, and wherein emissions generated by each group of solid state light emitters are arranged to be combined to produce aggregate emissions of the lighting device.

In certain embodiments, at least one processor is arranged to utilize at least one instruction set and/or to execute steps of at least one algorithm of a plurality of selectable algorithms (or an additional algorithm) to automatically adjust at different hours of a calendar day (a) luminous flux of the aggregate emissions and (b) at least one of CCT and color point of the aggregate emissions. In certain embodiments, at least one sensor is arranged to receive or provide at least one signal indicative of an environmental condition, wherein the at least one processor is arranged to execute steps of at least one algorithm of a plurality of selectable algorithms or the additional algorithm to automatically adjust at different hours of a calendar day (a) luminous flux of the aggregate emissions and (b) at least one of CCT and color point of the aggregate emissions, responsive to at least one of (i) time and (ii) the at least one signal indicative of an environmental condition. In certain embodiments, at least one sensor is arranged to receive or provide at least one signal indicative of an environmental condition comprises one or more of: an ambient light sensor, an image sensor, a temperature sensor, a barometric pressure sensor, a humidity sensor, a weather information receiver, a gas detector, and a particulate detector. In certain embodiments, at least one processor is arranged to execute steps of at least one algorithm of a plurality of selectable algorithms or the additional algorithm to automatically adjust at different hours of a calendar day at least one of (c) melatonin suppressing milliwatts per hundred lumens of the aggregate emissions and (d) relative gamut of the aggregate emissions, for a selected color point or CCT of the aggregated emissions. In certain embodiments, the plurality of groups of solid state light emitters comprises at least five groups of solid state light emitters. In certain embodiments, at least one detector is arranged to detect one or more of (i) multiple different user-generated sound patterns indicative of user commands, (ii) multiple different user-generated gesture patterns indicative of user commands, and (iii) at least one user-initiated (e.g., wired or wireless) signal, and produce at least one detector output signal responsive to such detection; wherein the at least one processor is further arranged to suspend or alter automatic adjustment of (a) luminous flux of the aggregate emissions and (b) at least one of CCT and color point of the aggregate emissions, responsive to the at least one detector output signal.

In certain embodiments, methods facilitating control of a lighting device involve automatic analysis of stored information regarding detected usage of a lighting device, automatically analyzing the stored information to identify temporal patterns of usage, and generating a modified set of operating instructions to be used by a processor for operating a lighting device.

In certain embodiments, a method facilitates control of a lighting device that comprises a memory and a plurality of groups of solid state light emitters, wherein each group of solid state light emitters is arranged to generate emissions comprising a dominant wavelength that differs from a dominant wavelength of emissions generated by each other group of solid state light emitters, each group of solid state light emitters is independently controllable, and emissions generated by each group of solid state light emitters are arranged to be combined to produce aggregate emissions of the lighting device. The method comprises: detecting usage of the lighting device; storing, in the memory of the lighting device, information regarding detected usage of the lighting device, wherein the stored information includes information indicative of color point and luminous flux of aggregate emissions with respect to time; analyzing the stored information to identify one or more temporal patterns of usage of the lighting device; generating a proposed operating instruction set responsive to the identification of one or more temporal patterns of usage; and adjusting operation of the plurality of groups of solid state light emitters utilizing the proposed operating instruction set. In certain embodiments, the analyzing, generating, and adjusting steps are performed by at least one processor of the lighting device. In certain embodiments, the lighting device comprises at least one sensor arranged to receive or provide at least one signal indicative of an environmental condition. In certain embodiments, a method further comprises storing, in the memory of the lighting device, environmental condition information incorporating or derived from the at least one signal for time periods corresponding to the detected usage of the lighting device. In certain embodiments, the analyzing of the stored information to identify one or more temporal patterns of usage of the lighting device includes analyzing information regarding (i) detected usage of the lighting device and (ii) environmental condition information, wherein the one or more temporal patterns of usage are correlated to the environmental condition information. In certain embodiments, a proposed operating instruction set is arranged to operate the plurality of groups of solid state light emitters responsive to at least one signal received or provided by the at least one sensor. In certain embodiments, a method further comprises eliciting approval by a user of the proposed operating instruction set prior to adjusting operation of the plurality of groups of solid state light emitters utilizing the proposed operating instruction set. In certain embodiments, at least one processor is arranged to adjust, responsive to the at least one detector output signal and for a selected color point or CCT of the aggregated emissions, at least one of (c) melatonin suppressing milliwatts per hundred lumens of the aggregate emissions and (d) relative gamut of the aggregate emissions.

In one embodiment, a method facilitates control of a lighting device that comprises a body structure, a memory, a processor, and a plurality of solid state light emitters, wherein the memory, the processor, and the plurality of solid state light emitters are arranged in or on the body structure;

the memory is arranged to store a plurality of selectable algorithms arranged to enable different control of operation the plurality of solid state light emitters; the processor is arranged to execute steps of at least one algorithm of the plurality of selectable algorithms; and emissions generated by the solid state light emitters are arranged to be combined to produce aggregate emissions of the lighting device. The method facilitating control of the lighting device comprises: downloading or retrieving from a communication network an additional selectable algorithm arranged to enable control of operation of the plurality of solid state light emitters; and saving the additional selectable algorithm in the memory of the lighting device while maintaining in the memory at least one other selectable algorithm. In certain embodiments, the method further comprises utilizing at least one detector associated with the lighting device to detect one or more of (i) a user-generated sound pattern indicative of a user command, (ii) a user-generated gesture pattern indicative of a user command, and (iii) at least one user-initiated (e.g., wired or wireless) signal, and selecting the additional selectable algorithm saved in the memory of the lighting device responsive to said detection to initiate execution by the processor of steps of the additionally selectable algorithm for control of the lighting device.

Embodiments as disclosed herein may provide one or more of the following beneficial technical effects: enhancing controllability of emissions of lighting devices; enhancing vividness of colors represented by lighting devices; enhancing control of melatonin suppression characteristics; enhancing flexibility in operating lighting devices; and simplifying the ability to update operating instructions for lighting devices.

Those skilled in the art will recognize improvements and modifications to the preferred embodiments of the present disclosure. All such improvements and modifications are considered within the scope of the concepts disclosed herein and the claims that follow. Various combinations and sub-combinations of the structures described herein are contemplated and will be apparent to a skilled person having knowledge of this disclosure. Any of the various features and elements as disclosed herein may be combined with one or more other disclosed features and elements unless indicated to the contrary herein. Correspondingly, the invention as hereinafter claimed is intended to be broadly construed and interpreted, as including all such variations, modifications and alternative embodiments, within its scope and including equivalents of the claims.

What is claimed is:

1. A solid state lighting device comprising:
   a plurality of groups of solid state light emitters, wherein emissions generated by each group of solid state light emitters are arranged to be combined to produce aggregate emissions of the solid state lighting device;
   a controller module to utilize the at least one operating instruction set to automatically adjust (a) luminous flux of the aggregate emissions and (b) at least one of correlated color temperature or color point of the aggregate emissions; and
   a first wireless transceiver arranged to receive at least one first signal from a digital communication device or a digital computing device;
   wherein the controller module is arranged to adjust, responsive to the received at least one first signal and for a selected color point or correlated color temperature of the aggregate emissions, at least one of (c) melatonin suppressing milliwatts per hundred lumens of the aggregate emissions or (d) relative gamut of the aggregate emissions.

2. The solid state lighting device of claim 1, wherein the controller module is arranged to perform at least one of the following adjustments (i) or (ii) while maintaining at least one of the following conditions (iii) or (iv):
   (i) adjust melatonin suppressing milliwatts per hundred lumens of the aggregate emissions by at least 10%,
   (ii) adjust relative gamut of the aggregate emissions by at least 8%,
   (iii) maintain aggregate emissions of the solid state lighting device within four MacAdam ellipses of a target correlated color temperature value, and
   (iv) maintain aggregate emissions of the solid state lighting device at or above a color rendering index (CRI) value of at least 70.

3. The solid state lighting device of claim 1, further comprising at least one detector arranged to detect one or more of (i) multiple different user-generated sound patterns indicative of user commands, (ii) multiple different user-generated gesture patterns indicative of user commands, or (iii) at least one user-initiated signal, and to produce at least one detector output signal responsive to such detection;
   wherein the controller module is further arranged to suspend or alter automatic adjustment of (a) luminous flux of the aggregate emissions and (b) at least one of correlated color temperature or color point of the aggregate emissions, responsive to the at least one detector output signal.

4. The solid state lighting device of claim 1, wherein each group of solid state light emitters within the plurality of groups of solid state light emitters is independently controllable.

5. The solid state lighting device of claim 1, wherein the plurality of groups of solid state light emitters, the controller module, and the first wireless transceiver are arranged in or on a single body structure.

6. The solid state lighting device of claim 1, wherein the aggregate emissions generated by the solid state lighting device comprise at least one of the following characteristics (A) to (D):
   (A) a color rendering index (CRI) value of at least 90 and a relative gamut ($Q_g$) value of at least 100 within a correlated color temperature range spanning at least from 2700K to 9000K;
   (B) a color rendering index R9 value of at least 80 within a correlated color temperature range spanning at least from 2700K to 9000K;
   (C) a luminous flux value of at least 600 within a correlated color temperature range spanning at least from 2700K to 9000K; or
   (D) a luminous efficacy of radiation value of at least 300 within a correlated color temperature range spanning at least from 2700K to 5700K.

7. The solid state lighting device of claim 1, further comprising a second wireless transceiver arranged to transmit at least one second signal to at least one other solid state lighting device, wherein the at least one second signal is indicative of or includes a signal produced by the control module responsive to receipt of the at least one first signal.

8. A lighting device comprising a controller module and a plurality of groups of solid state light emitters, wherein emissions generated by each group of solid state light emitters are arranged to be combined to produce aggregate emissions of the lighting device, wherein the controller module is configured to:

store information regarding detected usage of the lighting device, wherein the stored information includes information indicative of color point and luminous flux of aggregate emissions with respect to time;

analyze the stored information to identify one or more temporal patterns of usage of the lighting device;

generate a proposed operating instruction set responsive to the identification of one or more temporal patterns of usage; and adjust operation of the plurality of groups of solid state light emitters utilizing the proposed operating instruction set.

9. The lighting device of claim 8, further comprising at least one sensor arranged to receive or provide at least one signal indicative of an environmental condition, wherein the controller module is further configured to:

store, in a memory of the lighting device, environmental condition information incorporating or derived from the at least one signal for time periods corresponding to the detected usage of the lighting device; and analyze information regarding (i) detected usage of the lighting device and (ii) the stored environmental condition information, to identify the one or more temporal patterns of usage of the lighting device;

wherein the one or more temporal patterns of usage are correlated to the environmental condition information; and wherein the proposed operating instruction set is arranged to operate the plurality of groups of solid state light emitters responsive to at least one signal received or provided by the at least one sensor.

10. The solid state lighting device of claim 9, wherein the at least one sensor arranged to receive or provide at least one signal indicative of an environmental condition comprises one or more of: an ambient light sensor, an image sensor, a temperature sensor, a barometric pressure sensor, a humidity sensor, a weather information receiver, a gas detector, and a particulate detector.

11. The solid state lighting device of claim 9, wherein the plurality of groups of solid state light emitters, the controller module, and the at least one sensor are arranged in or on a single body structure.

12. The solid state lighting device of claim 8, wherein the controller module is further configured to elicit approval by a user of the proposed operating instruction set prior to adjusting operation of the plurality of groups of solid state light emitters utilizing the proposed operating instruction set.

13. The solid state lighting device of claim 8, wherein each group of solid state light emitters within the plurality of groups of solid state light emitters is independently controllable.

14. The solid state lighting device of claim 8, wherein the aggregate emissions generated by the solid state lighting device comprise at least one of the following characteristics (A) to (D):

(A) a color rendering index (CRI) value of at least 90 and a relative gamut ($Q_g$) value of at least 100 within a correlated color temperature range spanning at least from 2700K to 9000K;

(B) a color rendering index R9 value of at least 80 within a correlated color temperature range spanning at least from 2700K to 9000K;

(C) a luminous flux value of at least 600 within a correlated color temperature range spanning at least from 2700K to 9000K; or (D) a luminous efficacy of radiation value of at least 300 within a correlated color temperature range spanning at least from 2700K to 5700K.

15. The solid state lighting device of claim 8, further comprising at least one detector arranged to detect one or more of (i) multiple different user-generated sound patterns indicative of user commands, (ii) multiple different user-generated gesture patterns indicative of user commands, and (iii) at least one user-initiated signal, and produce at least one detector output signal responsive to such detection.

16. A solid state lighting device comprising:

a plurality of groups of solid state light emitters, wherein emissions generated by each group of solid state light emitters are arranged to be combined to produce aggregate emissions of the solid state lighting device;

a controller module configured to utilize at least one stored operating instruction set to automatically adjust at different hours of a calendar day (a) luminous flux of the aggregate emissions and (b) at least one of correlated color temperature or color point of the aggregate emissions, responsive to at least one of (i) time or (ii) at least one signal indicative of an environmental condition;

wherein the aggregate emissions generated by the solid state lighting device comprise a color rendering index (CRI) value of at least 90 and a relative gamut ($Q_g$) value of at least 100 within a correlated color temperature range spanning at least from 2700K to 9000K in combination with at least one of the following features (A) or (B):

(A) a luminous flux value of at least 600 within a correlated color temperature range spanning at least from 2700K to 9000K; or (B) a luminous efficacy of radiation value of at least 300 within a correlated color temperature range spanning at least from 2700K to 5700K.

17. The solid state lighting device of claim 16, wherein the controller module is arranged to utilize the at least one operating instruction set to automatically adjust at different hours of a calendar day at least one of (c) melatonin suppressing milliwatts per hundred lumens of the aggregate emissions or (d) relative gamut of the aggregate emissions, for a selected color point or correlated color temperature of the aggregate emissions.

18. The solid state lighting device of claim 16, further comprising at least one detector arranged to detect one or more of (i) multiple different user-generated sound patterns indicative of user commands, (ii) multiple different user-generated gesture patterns indicative of user commands, or (iii) at least one user-initiated signal, and to produce at least one detector output signal responsive to such detection;

wherein the controller module is further arranged to suspend or alter automatic adjustment of (a) luminous flux of the aggregate emissions and (b) at least one of correlated color temperature or color point of the aggregate emissions, responsive to the at least one detector output signal.

19. The solid state lighting device of claim 16, wherein each group of solid state light emitters within the plurality of groups of solid state light emitters is independently controllable.

20. The solid state lighting device of claim 16, wherein the plurality of groups of solid state light emitters and the controller module are arranged in or on a single body structure.

* * * * *